US012178722B2

(12) United States Patent
Dalton et al.

(10) Patent No.: US 12,178,722 B2
(45) Date of Patent: Dec. 31, 2024

(54) TRIAL INSERT ASSEMBLY

(71) Applicant: Paragon 28, Inc., Englewood, CO (US)

(72) Inventors: Mark Ray Dalton, Austin, TX (US); Randy Allard, Golden, CO (US)

(73) Assignee: Paragon 28, Inc., Englewood, CO (US)

( * ) Notice: Subject to any disclaimer, the term of this patent is extended or adjusted under 35 U.S.C. 154(b) by 768 days.

(21) Appl. No.: 17/304,058

(22) Filed: Jun. 14, 2021

(65) Prior Publication Data

US 2021/0298920 A1 Sep. 30, 2021

Related U.S. Application Data

(63) Continuation of application No. PCT/US2019/065025, filed on Dec. 6, 2019.

(60) Provisional application No. 62/899,646, filed on Sep. 12, 2019, provisional application No. 62/779,092, filed on Dec. 13, 2018, provisional application No. 62/779,436, filed on Dec. 13, 2018.

(51) Int. Cl.
*A61F 2/46* (2006.01)
*A61F 2/42* (2006.01)
*A61F 2/30* (2006.01)

(52) U.S. Cl.
CPC .......... *A61F 2/4684* (2013.01); *A61F 2/4202* (2013.01); *A61F 2002/30553* (2013.01); *A61F 2002/30617* (2013.01); *A61F 2002/4627* (2013.01)

(58) Field of Classification Search
CPC .............................. A61F 2/4202; A61F 2/4684
See application file for complete search history.

(56) References Cited

U.S. PATENT DOCUMENTS

| 4,470,158 | A | * | 9/1984 | Pappas | A61F 2/4202 623/20.2 |
| 5,702,464 | A | | 12/1997 | Lackey | |
| 6,033,440 | A | | 3/2000 | Schall | |
| 7,011,687 | B2 | * | 3/2006 | Deffenbaugh | A61F 2/4202 623/21.18 |

(Continued)

FOREIGN PATENT DOCUMENTS

| CN | 107361883 | 11/2017 |
| CN | 108969162 | 12/2018 |

(Continued)

OTHER PUBLICATIONS

Extended European Search Report for European Application No. 19896548.5, Sep. 28, 2022, 7 pages.

(Continued)

*Primary Examiner* — Zade Coley
(74) *Attorney, Agent, or Firm* — Heslin Rothenberg Farley & Mesiti P.C.; Jacquelyn A. Graff, Esq.

(57) ABSTRACT

A trial insert having a first member having an engagement channel extending from a bottom surface towards a top surface and along a first direction that extends from a first end to a second end. The trial insert has a second member having an engagement member extending away from a top surface and along a second direction that extends from a first end to a second end, where the engagement member is received within the engagement channel, and where the first member is translatable relative to the second member along a longitudinal axis of the trial insert.

12 Claims, 46 Drawing Sheets

(56) References Cited

U.S. PATENT DOCUMENTS

| | | | |
|---|---|---|---|
| 7,547,327 B2 | 6/2009 | Collazo | |
| 8,114,091 B2 | 2/2012 | Ratron | |
| 8,147,557 B2 | 4/2012 | Lee | |
| 9,597,090 B2* | 3/2017 | Claypool | A61F 2/4657 |
| 2003/0204265 A1 | 10/2003 | Short | |
| 2005/0267600 A1 | 12/2005 | Haberman | |
| 2005/0288792 A1* | 12/2005 | Landes | A61B 17/1682 623/21.18 |
| 2006/0142870 A1* | 6/2006 | Robinson | A61B 17/142 606/87 |
| 2006/0229730 A1 | 10/2006 | Railey | |
| 2008/0103603 A1 | 5/2008 | Hintermann | |
| 2010/0161077 A1* | 6/2010 | Boone | A61F 2/80 623/53 |
| 2010/0298941 A1 | 11/2010 | Hes | |
| 2012/0158152 A1 | 6/2012 | Claypool | |
| 2013/0116797 A1* | 5/2013 | Coulange | A61B 17/15 623/21.18 |
| 2013/0261504 A1* | 10/2013 | Claypool | A61B 5/1036 600/587 |
| 2014/0188236 A1* | 7/2014 | McGinley | A61F 2/4684 623/21.18 |
| 2014/0371865 A1 | 12/2014 | Firestone | |
| 2015/0313727 A1 | 11/2015 | Waite, II | |
| 2015/0320567 A1* | 11/2015 | Terrill | A61F 2/4202 623/21.18 |
| 2015/0359642 A1 | 12/2015 | Claypool et al. | |
| 2016/0287400 A1 | 10/2016 | Muir et al. | |
| 2016/0367269 A9 | 12/2016 | McGinley et al. | |
| 2018/0125663 A1* | 5/2018 | Huxel | A61F 2/46 |
| 2018/0263639 A1 | 9/2018 | McGinley et al. | |

FOREIGN PATENT DOCUMENTS

| | | |
|---|---|---|
| JP | 5379966 | 12/2013 |
| KR | 1020180108949 | 10/2018 |

OTHER PUBLICATIONS

Cs&E PCT Collaborative Search and Examination Pilot Upload Peer Contribution in International Patent Application No. PCT/US2019/065025, Peer ISA—China National Intellectual Property Administration (CNIPA), Feb. 20, 2020, 10 pages.

Cs&E PCT Collaborative Search and Examination Pilot Upload Peer Contribution in International Patent Application No. PCT/US2019/065025, Peer ISA—Japan Patent Office (JPO), Feb. 17, 2020, 14 pages.

Cs&E PCT Collaborative Search and Examination Pilot Upload Peer Contribution in International Patent Application No. PCT/US2019/065025, Peer ISA—Korean Intellectual Property Office (KIPO), Feb. 25, 2020, 19 pages.

Cs&E PCT Collaborative Search and Examination Pilot Upload Peer Contribution in International Patent Application No. PCT/US2019/065025, Peer ISA—European Patent Office (EPO), Feb. 19, 2020, 13 pages.

International Search Report and Written Opinion of the International Searching Authority for PCT/US2019/065025, Mar. 20, 2020, 13 pages.

* cited by examiner

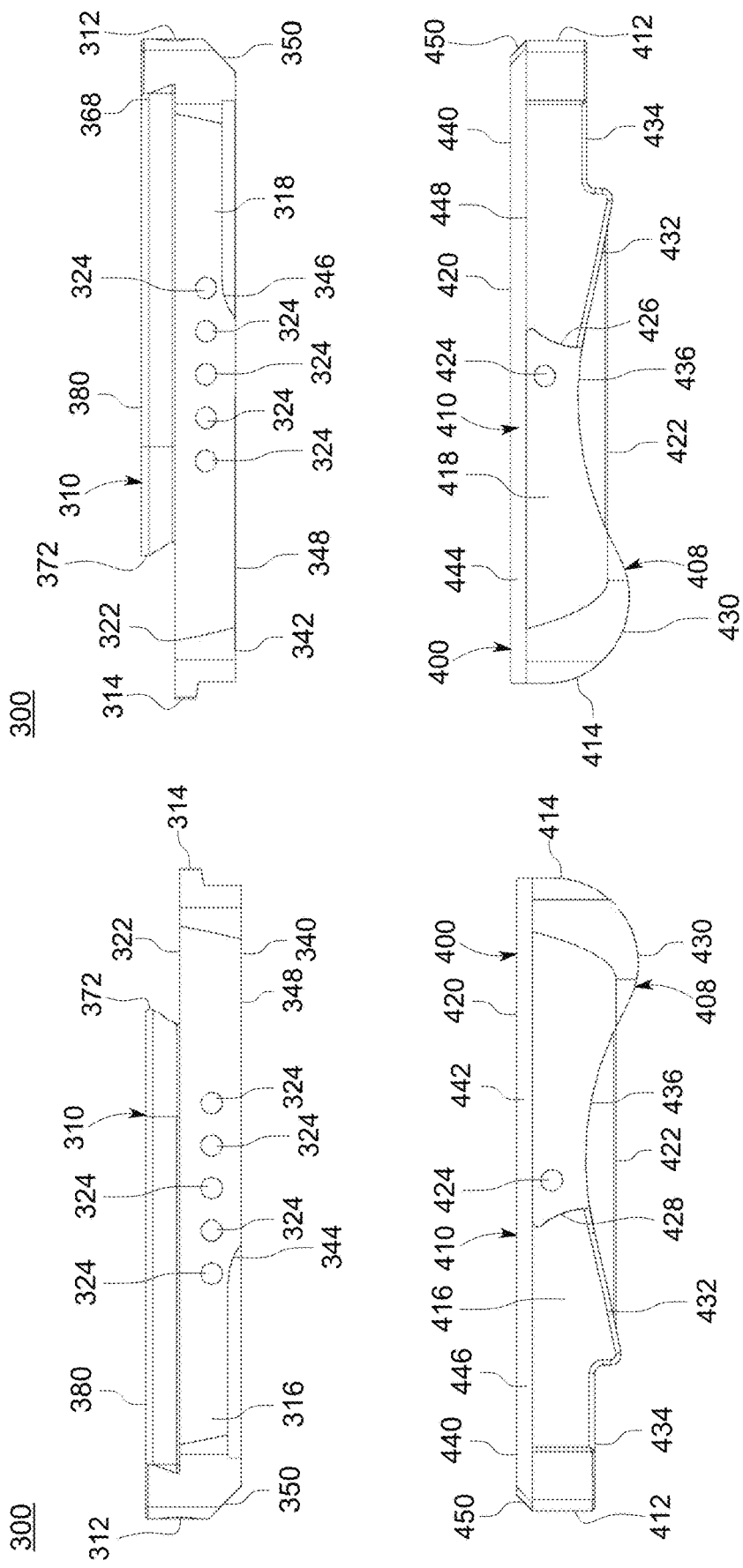

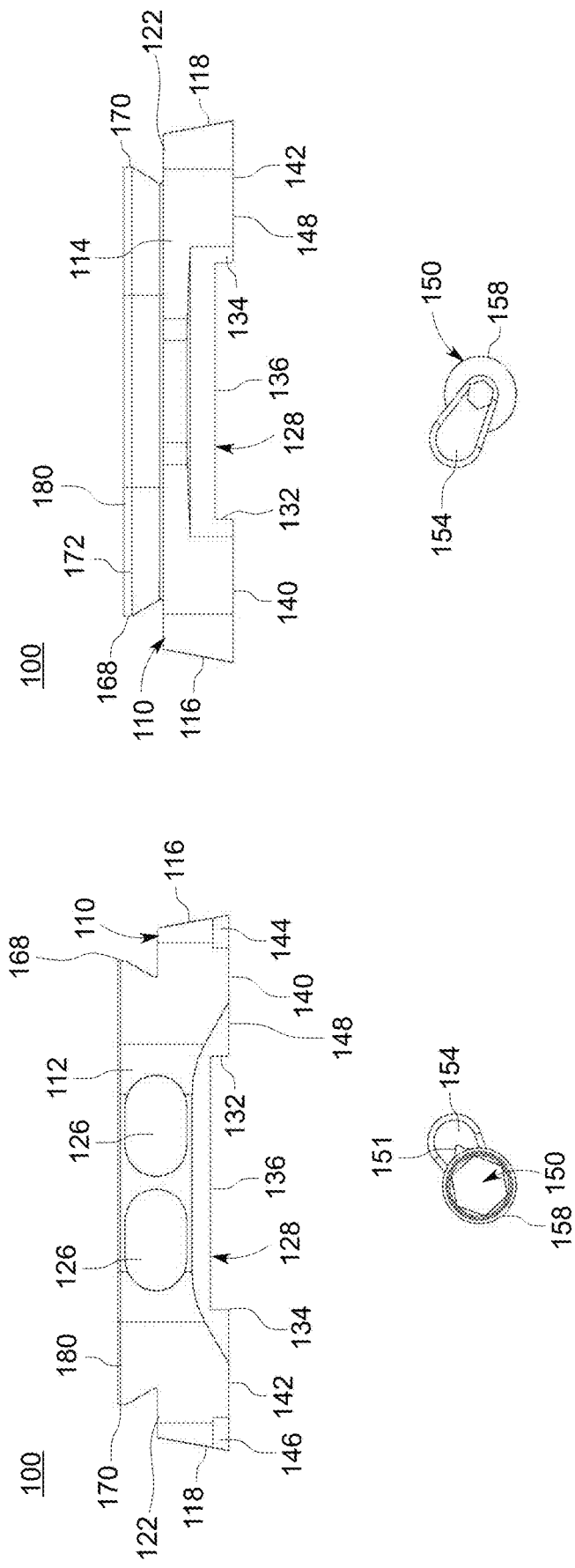

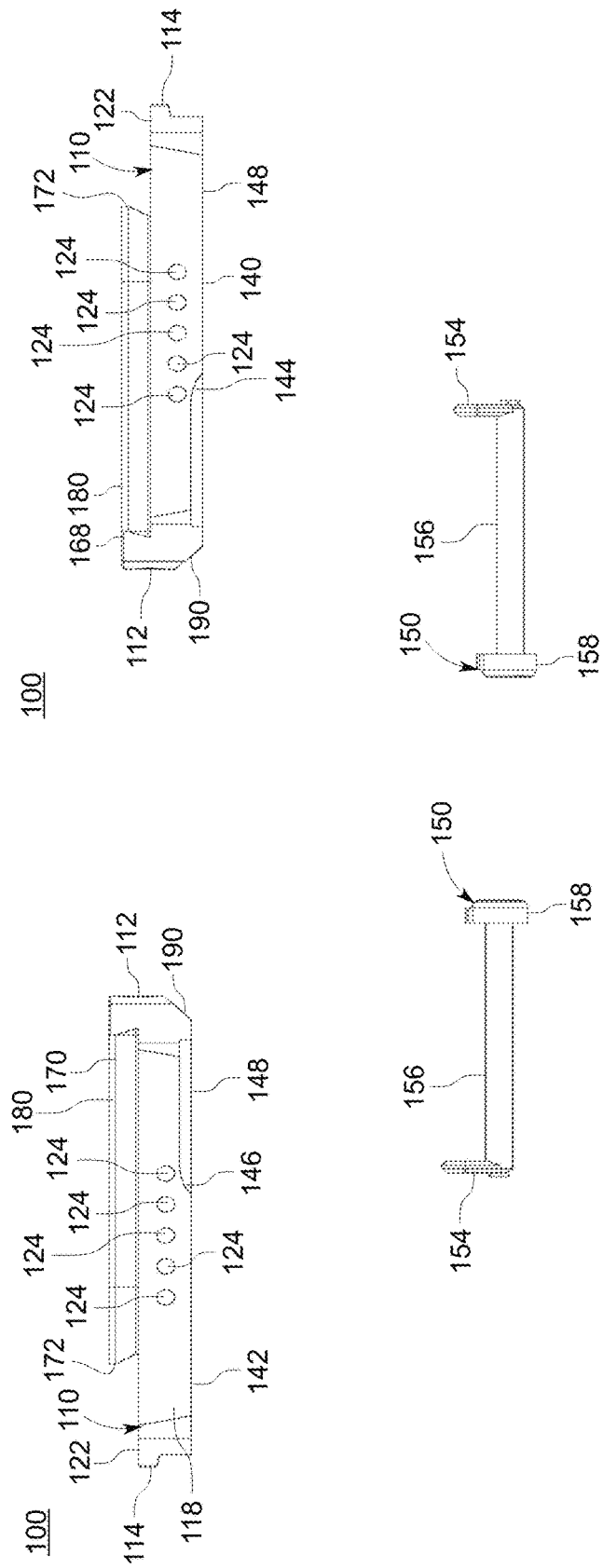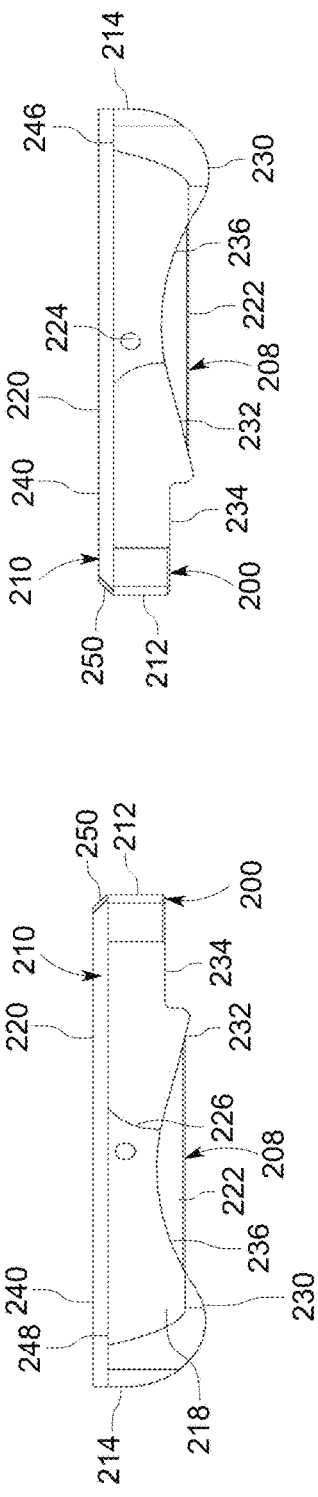
FIG. 30
FIG. 29

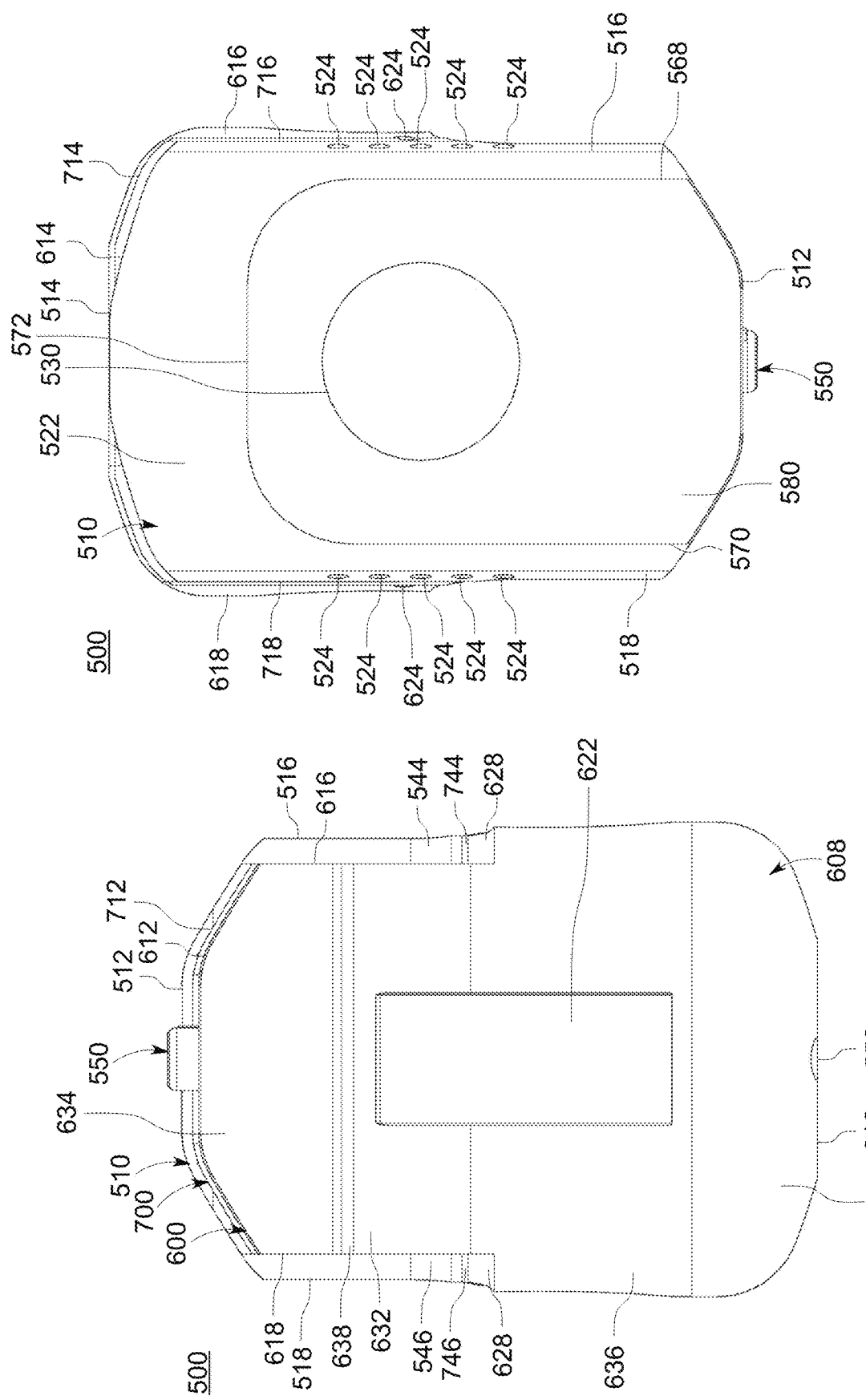

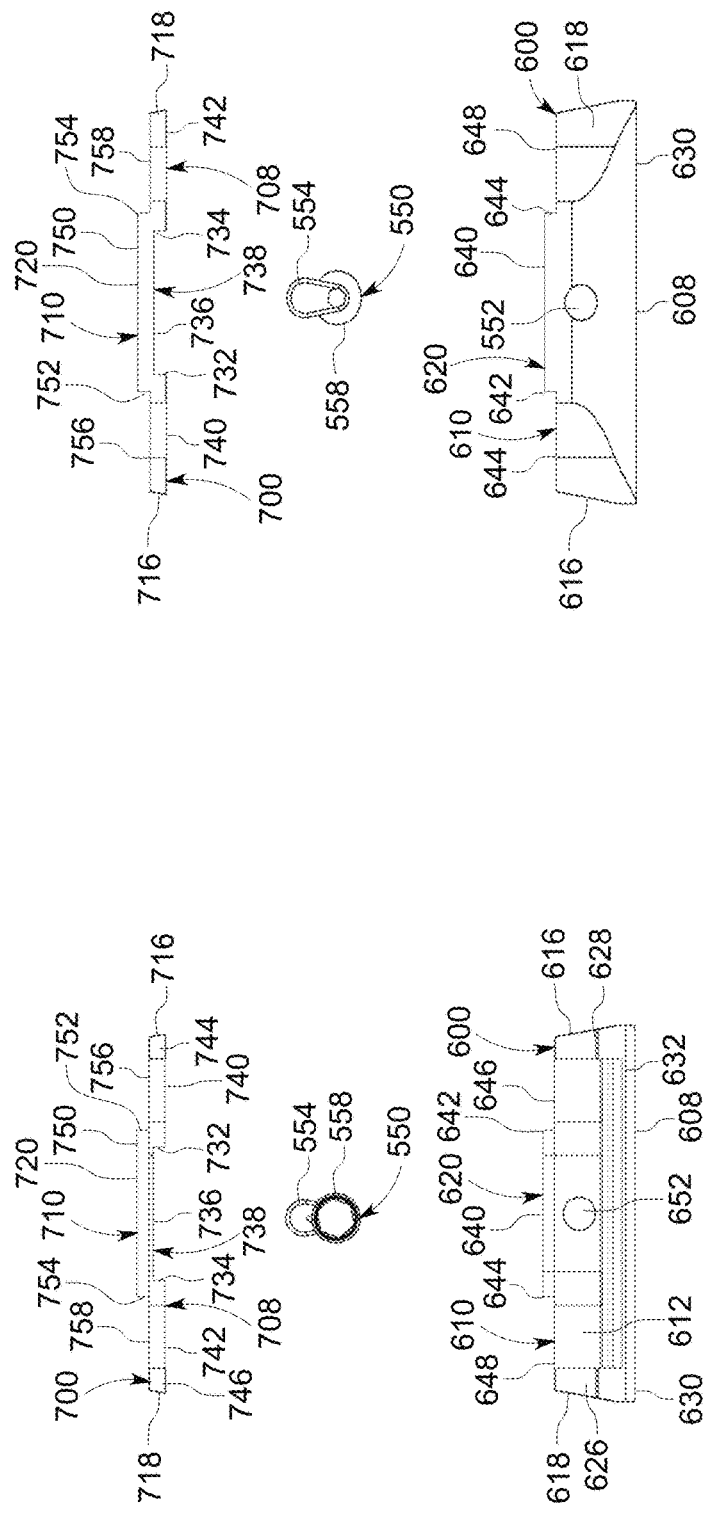
FIG. 48
FIG. 49

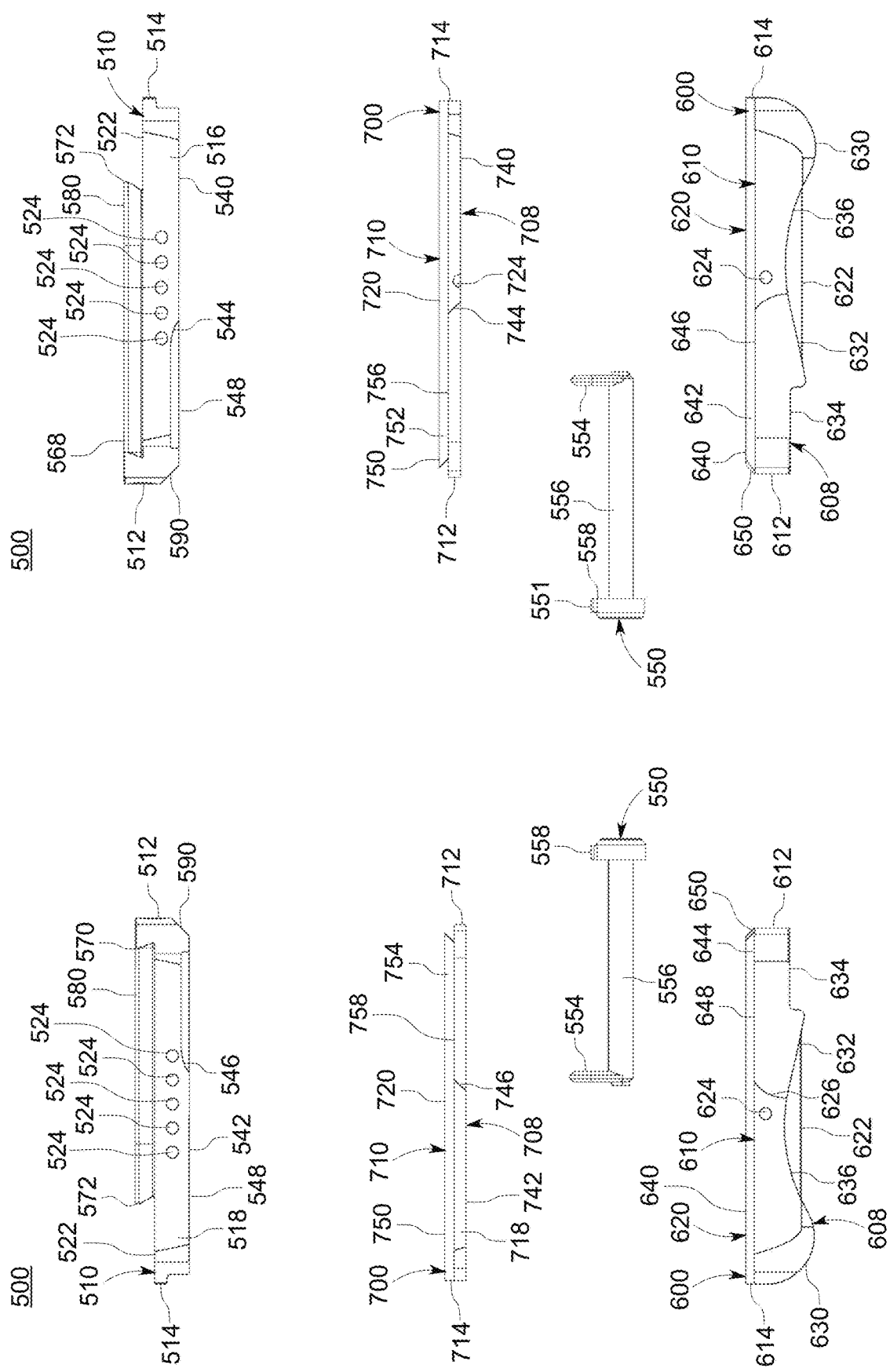

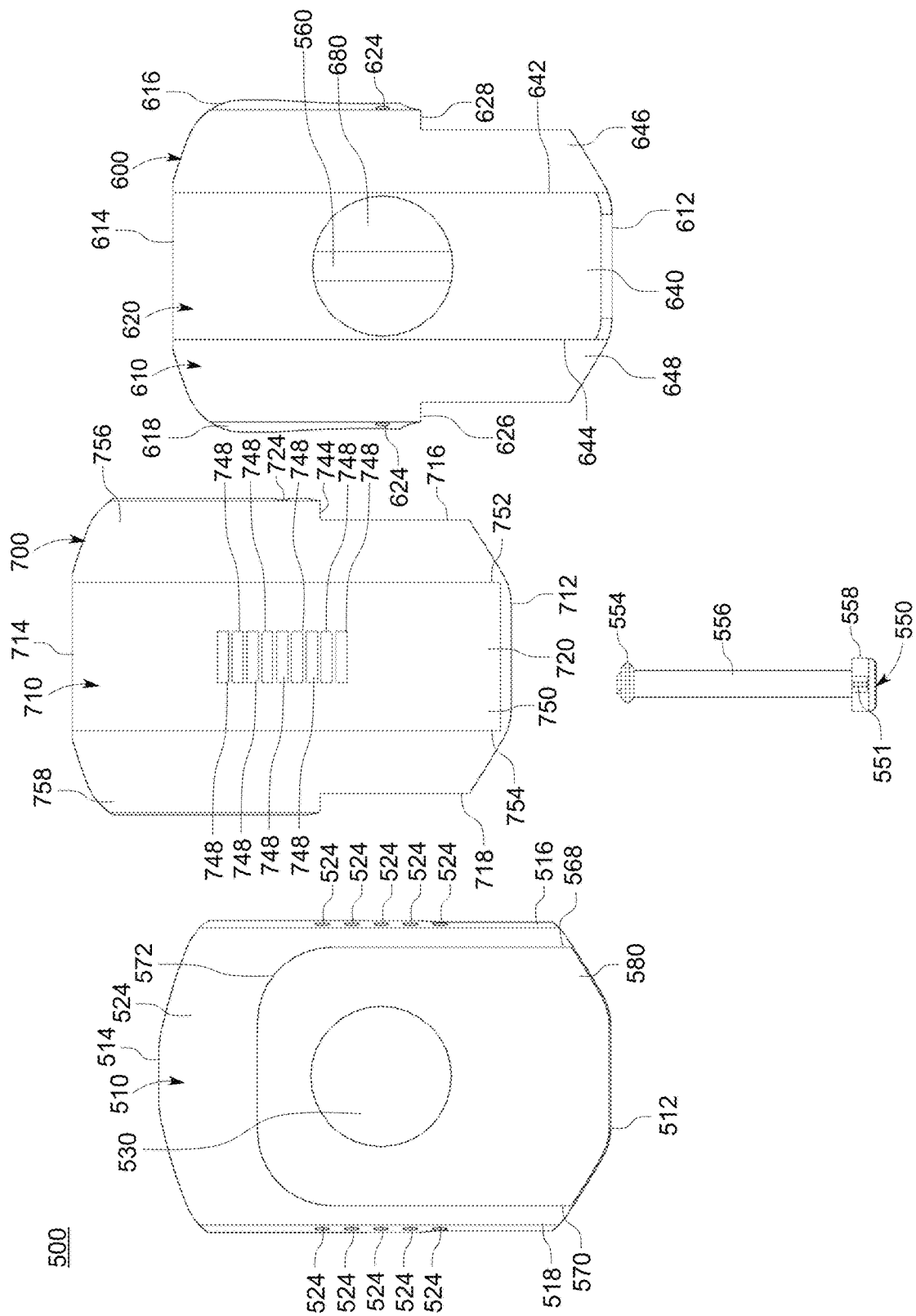

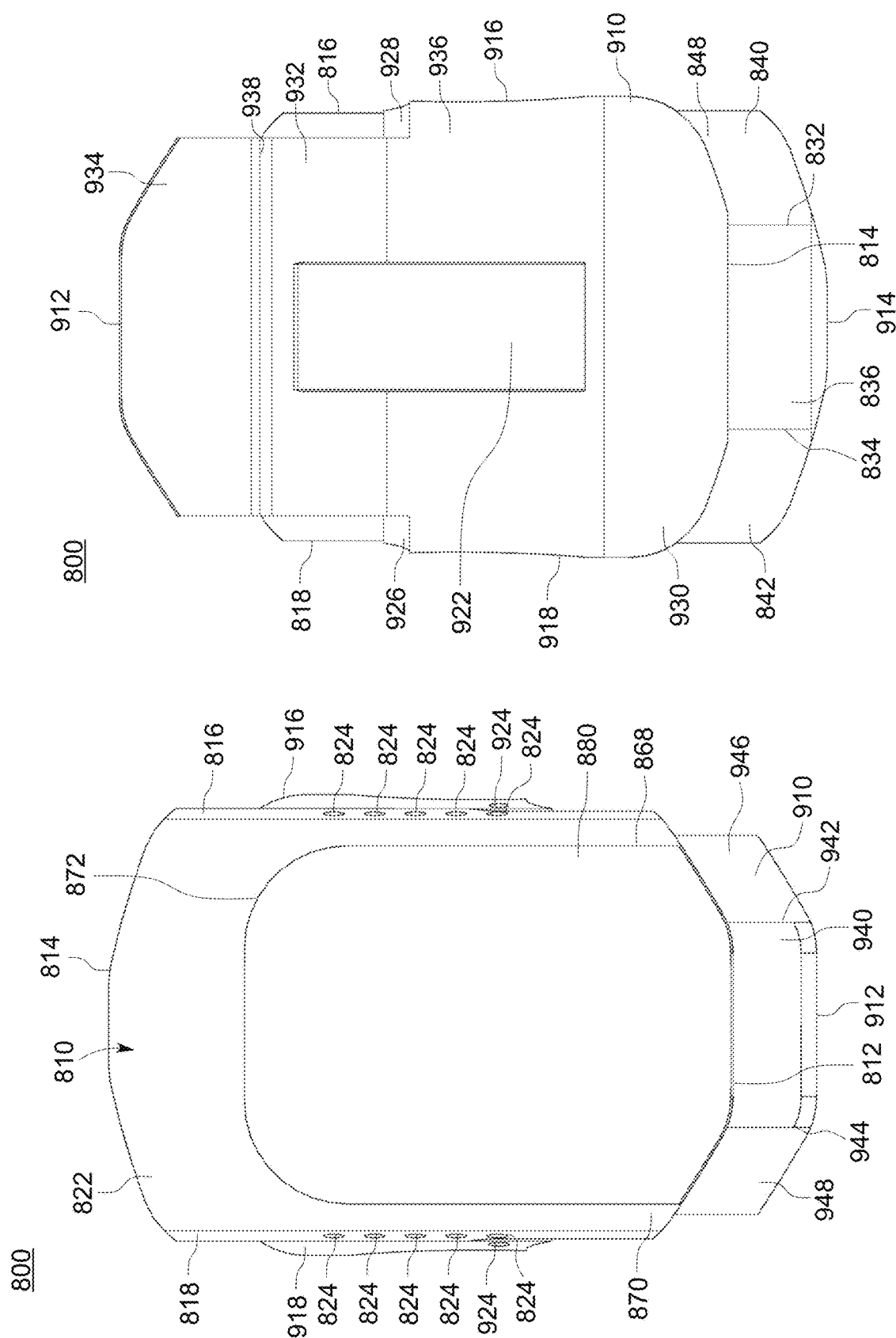

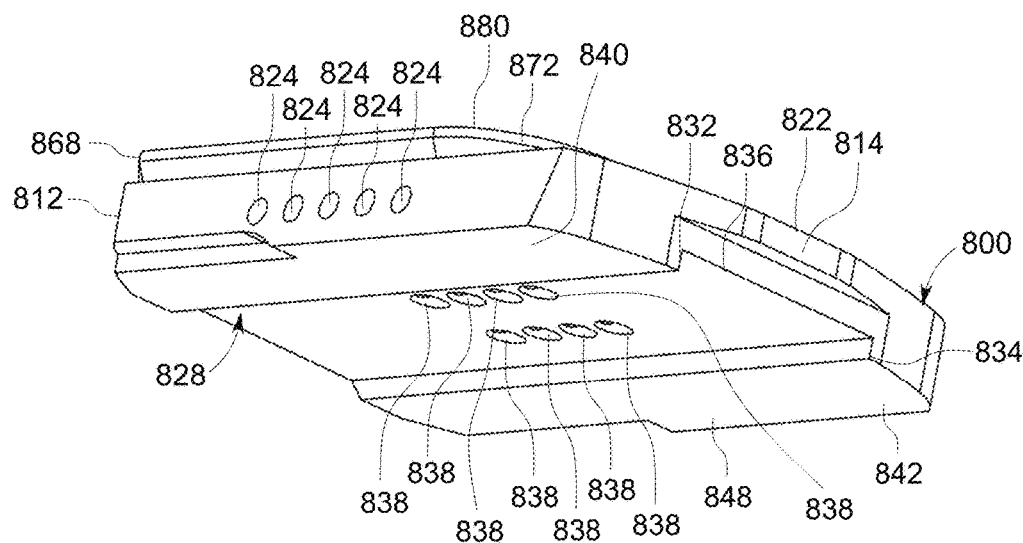
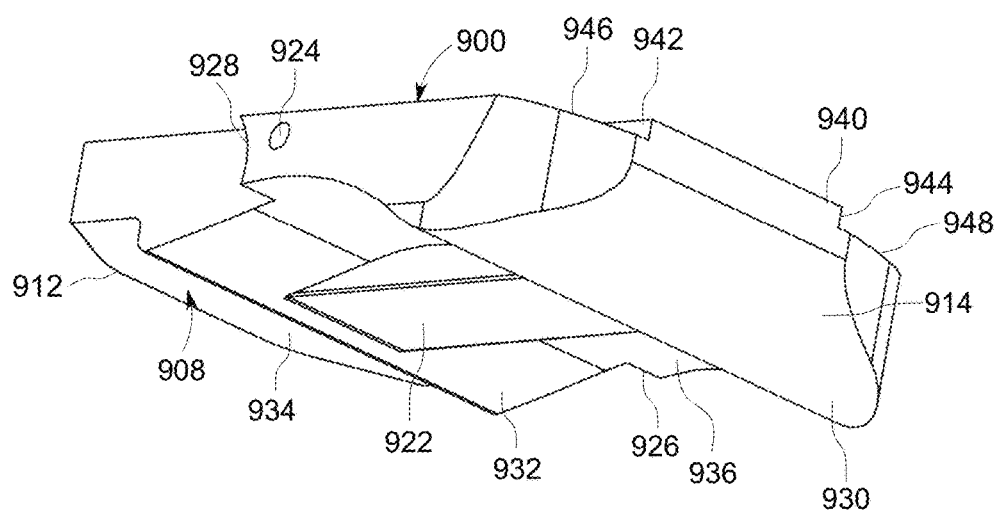
FIG. 68

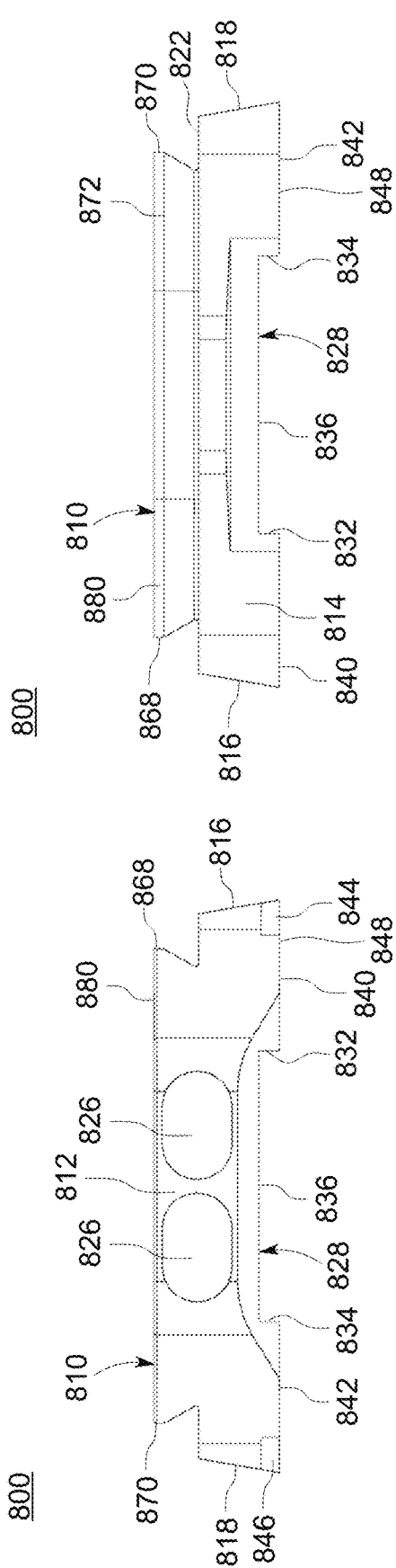
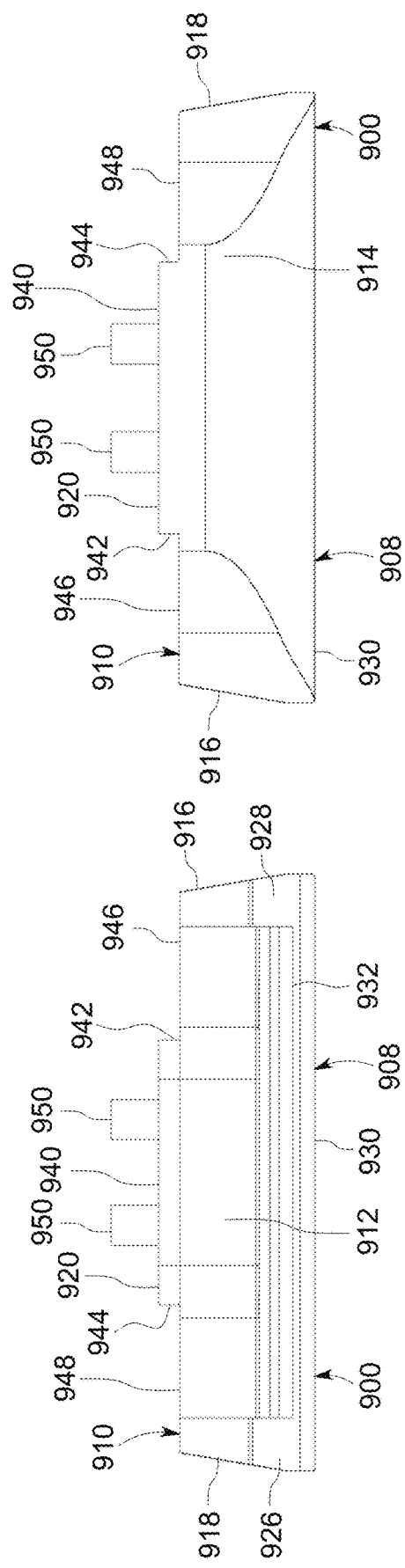
FIG. 69
FIG. 70

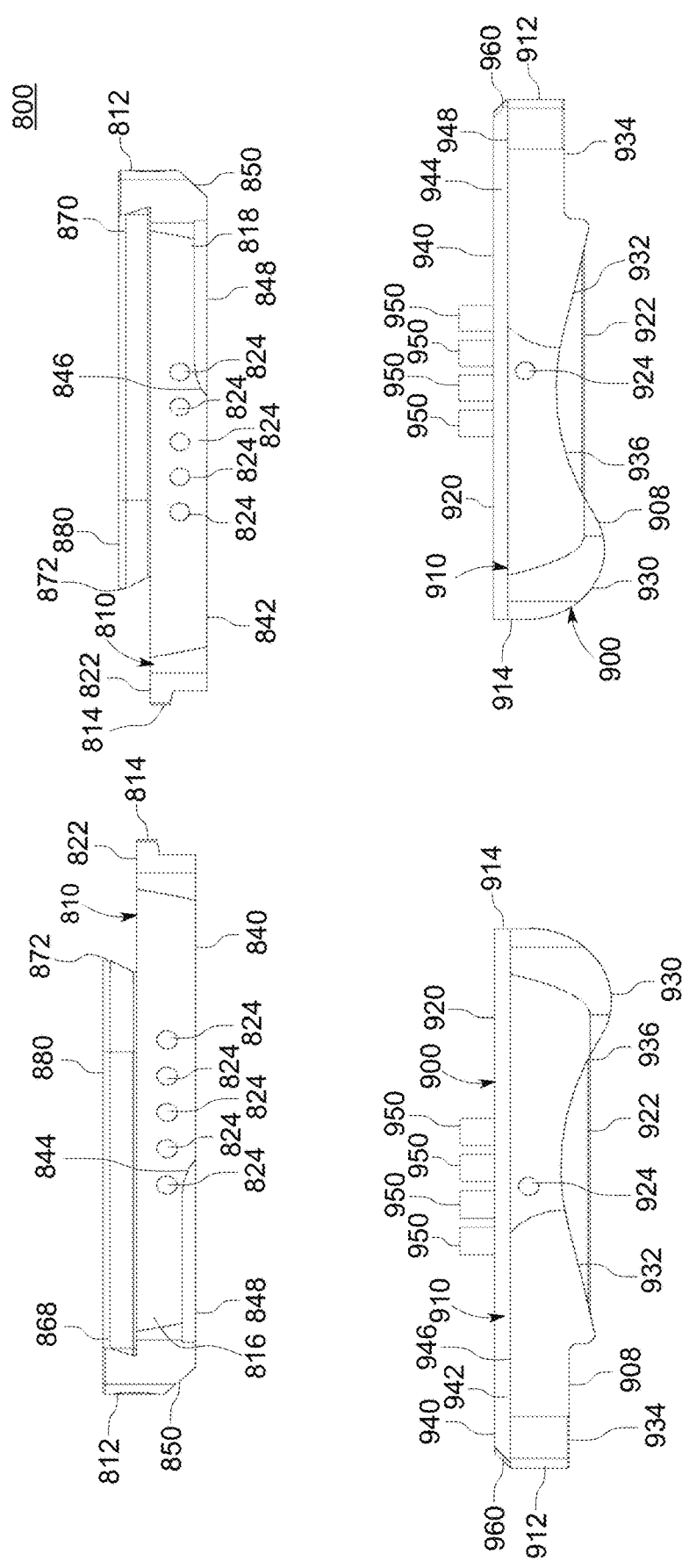

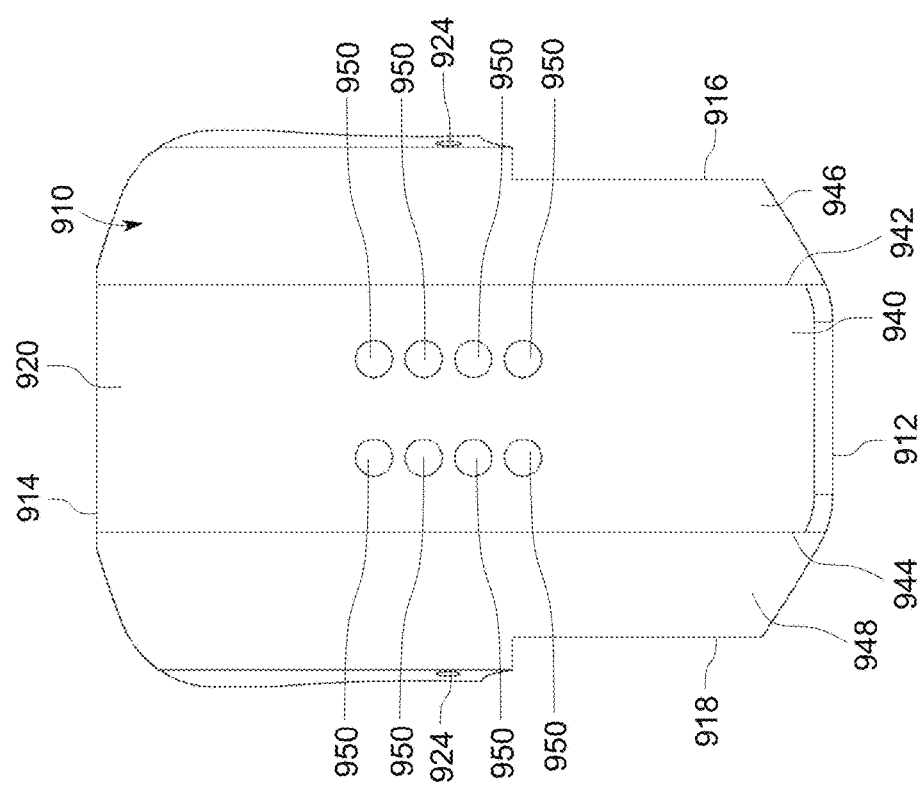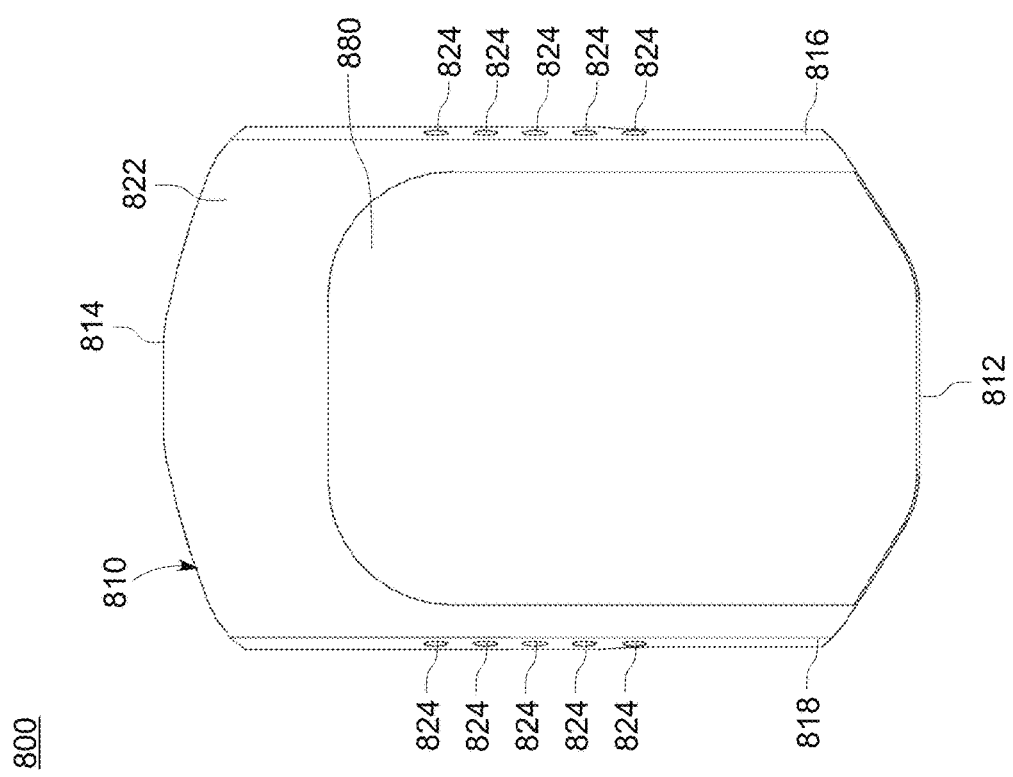
FIG. 73

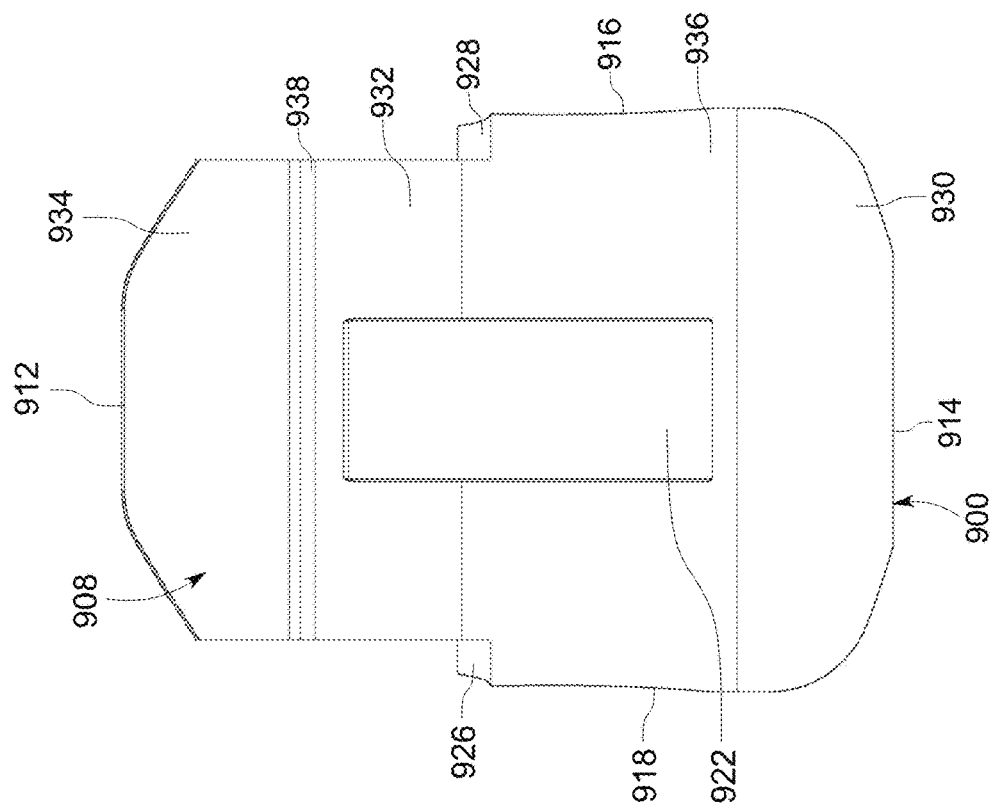
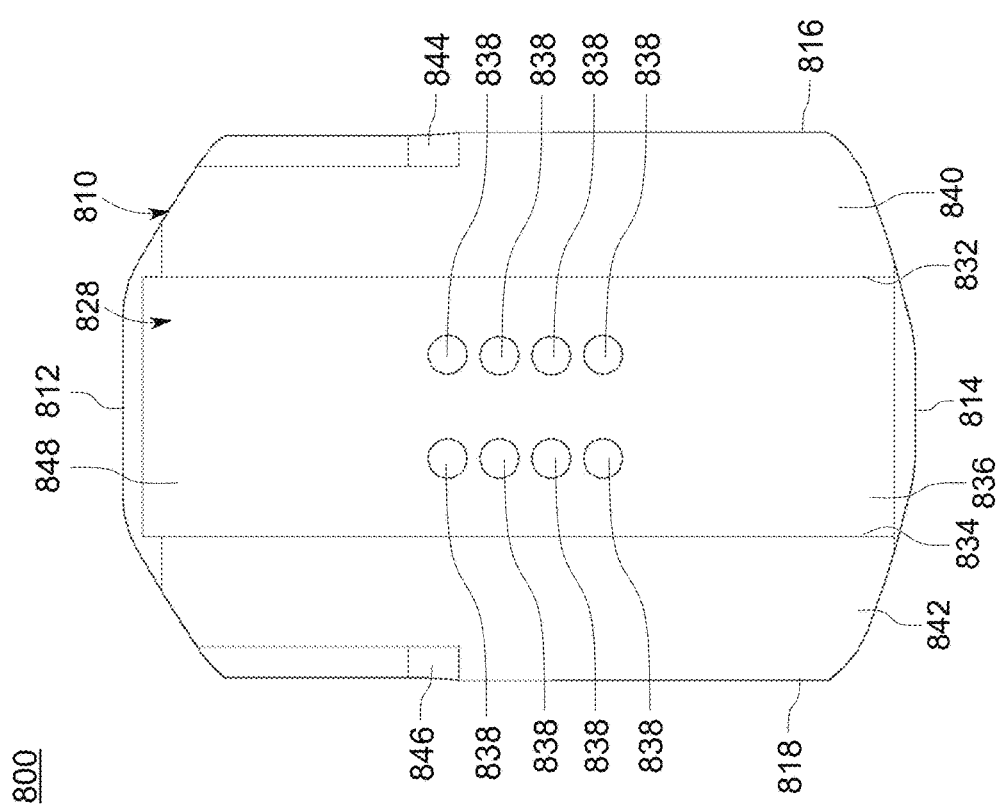
FIG. 74

TRIAL INSERT ASSEMBLY

CROSS-REFERENCE TO RELATED APPLICATIONS

This application is a continuation of PCT/US2019/065025 filed on Dec. 6, 2019 and entitled Trial Insert Assembly, which claims priority benefit under 35 U.S.C. § 119 to U.S. Provisional Application No. 62/779,092, filed Dec. 13, 2018, entitled Instruments, Guides and Related Methods for Total Ankle Replacement, U.S. Provisional Application No. 62/779,436, filed Dec. 13, 2018, entitled Joint Replacement Systems and Methods of Use and Assembly, and U.S. Provisional Application No. 62/899,646, filed Sep. 12, 2019, entitled Trial Insert Assembly, which are herein incorporated by reference in their entirety.

TECHNICAL FIELD

The present disclosure relates generally to general, podiatric, and orthopaedic surgery related to joint deformities. More specifically, but not exclusively, the present disclosure relates to implants, inserts, devices, and methods for maintaining, correcting, and/or resurfacing joint surfaces.

BACKGROUND OF THE INVENTION

Total ankle replacement (TAR), or ankle arthroplasty, is a surgical procedure to replace deformed and/or damaged articular surfaces of the human ankle joint with a prosthetic joint. TAR is becoming the treatment of choice for patients with a deformed and/or injured/damaged ankle joint, replacing the conventional use of arthrodesis (i.e. fusion of the ankle bones). One of the main advantages of TAR compared with ankle arthrodesis is preservation of functional range of motion (ROM), which is sacrificed in ankle fusion. Improved ROM allows patients to better perform activities of daily living and possibly regain athletic activities.

Many types of total ankle prostheses have been developed, such as, the cylindric-type ankle replacement prosthesis, the spherical-type ankle replacement prosthesis, and the sliding cylindric-type ankle replacement prosthesis. These and other typical total ankle replacement (TAR) prosthesis include a tibial prosthesis component, a talus prosthesis component, and a tibial bearing or insert component positioned between the tibial and talus prosthesis components. In these types of TAR prostheses, the tibial component is implanted on/in a tibia, the talus component is implanted on/in a talus, and the tibial insert is fixed to the tibial component articulating with the talus component to form a replacement ankle joint.

The proper size and position/orientation/alignment of the tibial component of a TAR prosthesis with respect to the distal end of a tibia and the corresponding ankle joint, the proper size and position/orientation/alignment of the talus component of the TAR prosthesis with respect to the proximal end of a talus and the corresponding ankle joint, and the proper size and position/orientation/alignment of the tibial insert of the TAR prosthesis with respect to the tibial component, the talus component and the corresponding ankle joint, are all important to achieving a stable replacement ankle joint and a replacement ankle joint that provides for full articulation/motion (e.g. achieving a range of motion of typical "healthy" ankle joints). For example, proper sizing and position/orientation/alignment of the tibial prosthesis, the talus prosthesis, and the tibial insert of a TAR prosthesis with respect to an ankle joint of a particular patient can prevent overstuffing or understuffing of the replacement ankle joint (and thereby provide full articulation/motion) and can ensure proper coverage of the tibial prosthesis on the tibia and the talus prosthesis on the talus. As another example, the position/orientation/alignment of the tibial prosthesis, the talus prosthesis, and the tibial insert with respect to the mechanical axis of an ankle joint of a particular patient (e.g. the mechanical axis of the tibia) can ensure the mechanical forces of the replacement ankle joint are properly distributed to achieve a full and properly-oriented range of motion.

Total ankle replacement instrumentation, guides, systems, and methods that facilitate the selection of a properly sized tibial prosthesis, talus prosthesis, and tibial insert of a total ankle replacement implant system for an ankle joint of a particular patient are thereby desirable. Further, total ankle replacement instrumentation, guides, systems, and methods that facilitate implantation of the tibial insert of a total ankle replacement implant system in proper positions and orientations for an ankle joint of a particular patient are thereby also desirable.

SUMMARY OF THE INVENTION

The present disclosure is directed toward implants, inserts, devices, and methods for use in maintaining, correcting, and/or resurfacing joint surfaces.

Provided in one aspect, is a trial insert having a first member having an engagement channel extending from a bottom surface towards a top surface and along a first direction that extends from a first end to a second end. The trial insert has a second member having an engagement member extending away from a top surface and along a second direction that extends from a first end to a second end, where the engagement member is received within the engagement channel, and where the first member is translatable relative to the second member along a longitudinal axis of the trial insert.

Provided in another aspect, is a method for using a trial insert including obtaining a joint replacement trial including a first trial component, a second trial component, and a trial insert. The method further includes connecting the first trial component to a first bone of a joint, connecting the second trial component to a second bone of the joint, and obtaining a trial insert. The trial insert has a first member having an engagement channel recessed into a bottom surface of the first member and a first bone trial connector extending away from a top surface of the first member. The trial insert further has a second member having an engagement member extending away from a top surface of the second member and a second bone trial connector recessed into a bottom surface of the second member, where the engagement member is movably coupled to the engagement channel. The method further includes connecting the first bone trial connector of a first member to the first trial component, connecting the second bone trial connector to the second trial component, determining a surgically desired position of the joint replacement trial, where determining the surgically desired position includes translating the first member relative to the second member until a desired joint range of motion is achieved, and locking the position of the first member relative to the second member.

In another aspect, a kit is provided, including a plurality of first members of a trial insert, where the first members include an engagement slot, and a plurality of second members of the trial insert, where the second members include an engagement member.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

FIG. 13 is an exploded, first side view of the trial insert of FIG. 1, in accordance with an aspect of the present disclosure;

FIG. 14 is an exploded, second side view of the trial insert of FIG. 1, in accordance with an aspect of the present disclosure;

FIG. 27 is an exploded, first end view of the trial insert of FIG. 17, in accordance with an aspect of the present disclosure;

FIG. 28 is an exploded, second end view of the trial insert of FIG. 17, in accordance with an aspect of the present disclosure;

FIG. 29 is an exploded, first side view of the trial insert of FIG. 17, in accordance with an aspect of the present disclosure;

FIG. 30 is an exploded, second side view of the trial insert of FIG. 17, in accordance with an aspect of the present disclosure;

FIG. 40 is a top view of the trial insert of FIG. 38, in accordance with an aspect of the present disclosure;

FIG. 41 is a bottom view of the trial insert of FIG. 38, in accordance with an aspect of the present disclosure;

FIG. 48 is an exploded, first end view of the trial insert of FIG. 38, in accordance with an aspect of the present disclosure;

FIG. 49 is an exploded, second end view of the trial insert of FIG. 38, in accordance with an aspect of the present disclosure;

FIG. 50 is an exploded, first side view of the trial insert of FIG. 38, in accordance with an aspect of the present disclosure;

FIG. 51 is an exploded, second side view of the trial insert of FIG. 38, in accordance with an aspect of the present disclosure;

FIG. 52 is an exploded, top view of the trial insert of FIG. 38, in accordance with an aspect of the present disclosure;

FIG. 61 is a top view of the trial insert of FIG. 59, in accordance with an aspect of the present disclosure;

FIG. 62 is a bottom view of the trial insert of FIG. 59, in accordance with an aspect of the present disclosure;

FIG. 68 is a second exploded, perspective view of the trial insert of FIG. 59, in accordance with an aspect of the present disclosure;

FIG. 69 is an exploded, first end view of the trial insert of FIG. 59, in accordance with an aspect of the present disclosure;

FIG. 70 is an exploded, second end view of the trial insert of FIG. 59, in accordance with an aspect of the present disclosure;

FIG. 71 is an exploded, first side view of the trial insert of FIG. 59, in accordance with an aspect of the present disclosure;

FIG. 72 is an exploded, second side view of the trial insert of FIG. 59, in accordance with an aspect of the present disclosure;

FIG. 73 is an exploded, top view of the trial insert of FIG. 59, in accordance with an aspect of the present disclosure; and FIG. 74 is an exploded, bottom of the trial insert of FIG. 59, in accordance with an aspect of the present disclosure.

DETAILED DESCRIPTION FOR CARRYING OUT THE INVENTION

Figure 1:
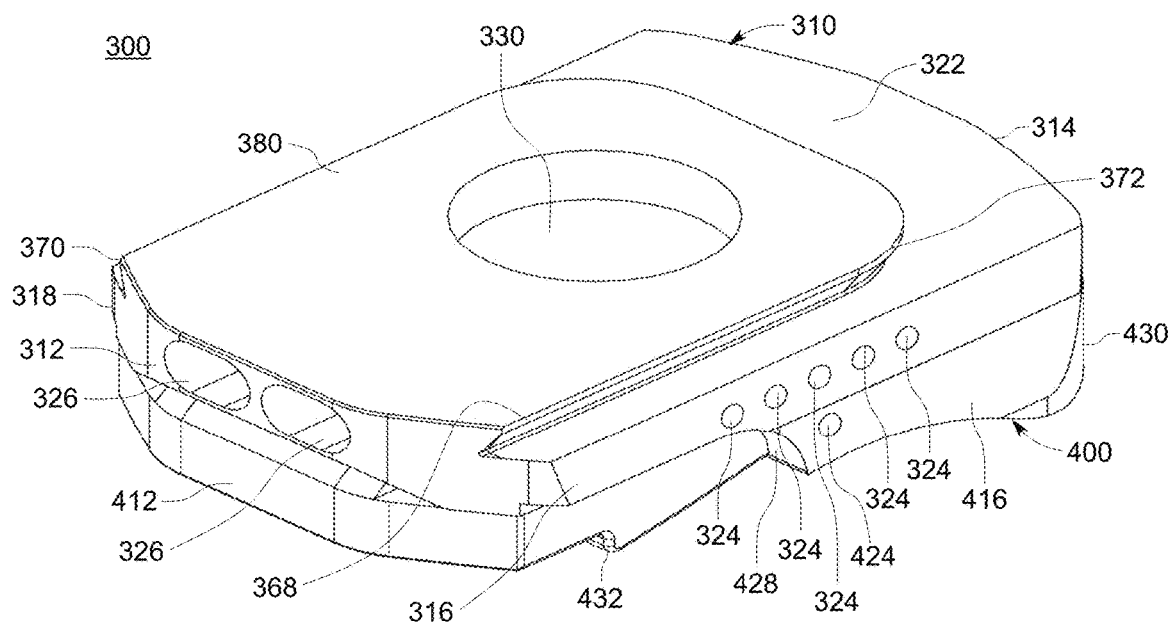
FIG. 1 is a first perspective view of one embodiment of a trial insert, in accordance with an aspect of the present disclosure.
Figure 2:
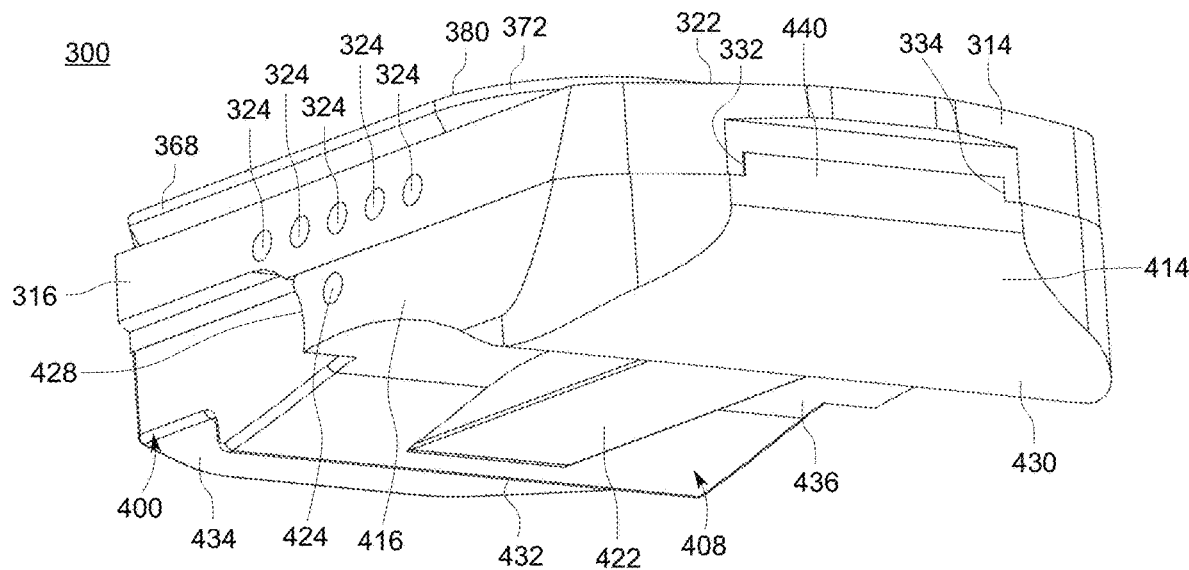
FIG. 2 is a second perspective view of the trial insert of FIG. 1, in accordance with an aspect of the present disclosure.

Generally stated, disclosed herein are devices, systems, and methods for maintaining, correcting, and/or resurfacing joint surfaces. Further, methods for using the implants, inserts, devices, and methods for maintaining, correcting, and/or resurfacing joint surfaces are discussed.

In this detailed description and the following claims, the words proximal, distal, anterior, plantar, posterior, dorsal, medial, lateral, superior, and inferior are defined by their standard usage for indicating a particular part or portion of a bone or trial insert according to the relative disposition of the natural bone or directional terms of reference. For example, "proximal" means the portion of a device or trial insert nearest the torso, while "distal" indicates the portion of the device or trial insert farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regard to the foot, the term "dorsal" refers to the top of the foot and the term "plantar" refers the bottom of the foot.

Similarly, positions or directions may be used herein with reference to anatomical structures or surfaces. For example, as the current devices, systems, instrumentation, and methods are described herein with reference to use with the bones of the ankle, the bones of the foot, ankle and lower leg may be used to describe the surfaces, positions, directions or orientations of the devices, systems, instrumentation, and methods. Further, the devices, systems, instrumentation and methods, and the aspects, components, features, and the like thereof, disclosed herein are described with respect to one side of the body for brevity purposes. However, as the human body is relatively symmetrical or mirrored about a line of symmetry (midline), it is hereby expressly contemplated that the devices, systems, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices, systems, instrumentation and methods, and the aspects, components, features, and the like thereof, described herein with respect to the right leg may be mirrored so that they likewise function with the left leg. Further, the devices, systems, instrumentation and methods, and the aspects, components, features, and the like thereof, disclosed herein are described with respect to the ankle for brevity purposes, but it should be understood that the devices, systems, instrumentation, and methods may be used with other bones or joints of the body having similar structures.

Referring to the drawings, wherein like reference numerals are used to indicate like or analogous components throughout the several views, and with particular reference to FIGS. 1-16, there is illustrated a trial insert 300. The trial insert 300 includes a first member or movable member 310 and a second member or base member 400. The first member 310 includes a top surface 322 opposite a bottom surface 348. The second member 400 includes a top surface 410 opposite a bottom surface or articulated surface 408. The top surface 410 of the second member 400 couples to the bottom surface 348 of the first member 310. The first member 310 and the second member 400 may come in, for example, multiple sizes for use with patients having different size tibia and talar bones.

As shown in FIGS. 9-16, the first member 310 includes a first end or anterior end 312 opposite a second end or posterior end 314. The distance between the first end 312 and the second end 314 may, for example, range from 28 mm to 42 mm, and more specifically may be approximately 30 mm. The first member 310 also includes a first side or medial side 316 opposite a second side or lateral side 318. The distance between the first side 316 and the second side 318 may, for example, range from approximately 20 mm to 34 mm, and more specifically may be approximately 20 mm. The top surface 322 includes a bone trial connector, a trial engagement member, or prosthetic engagement member 380, extending from the anterior end 312 towards the posterior end 314 and inset from the posterior end 314 by, for example, a range of approximately 4 mm to 8 mm, and more specifically may be approximately 7 mm, as shown in FIGS. 3, 5, 6, 13, 14, and 15. In addition, the trial engagement member 380 may be inset, for example, approximately 0 mm to 5 mm, more specifically, approximately 0 mm to 3 mm, from the first side 316 and the second side 318 respectively, and, yet more specifically inset approximately 1.8 mm from the first side 316 and the second side 318, as shown in FIGS. 7, 8, 11 and 12. The inset from the first side 316 and the second side 318 of the trial engagement member 380 may be, for example, also approximately equidistant. In an alternative embodiment, the trial engagement member 380 may, for example, extend between the first side 316 and the second side 318 and from the anterior end 312 to the posterior end 314

Figure 3:
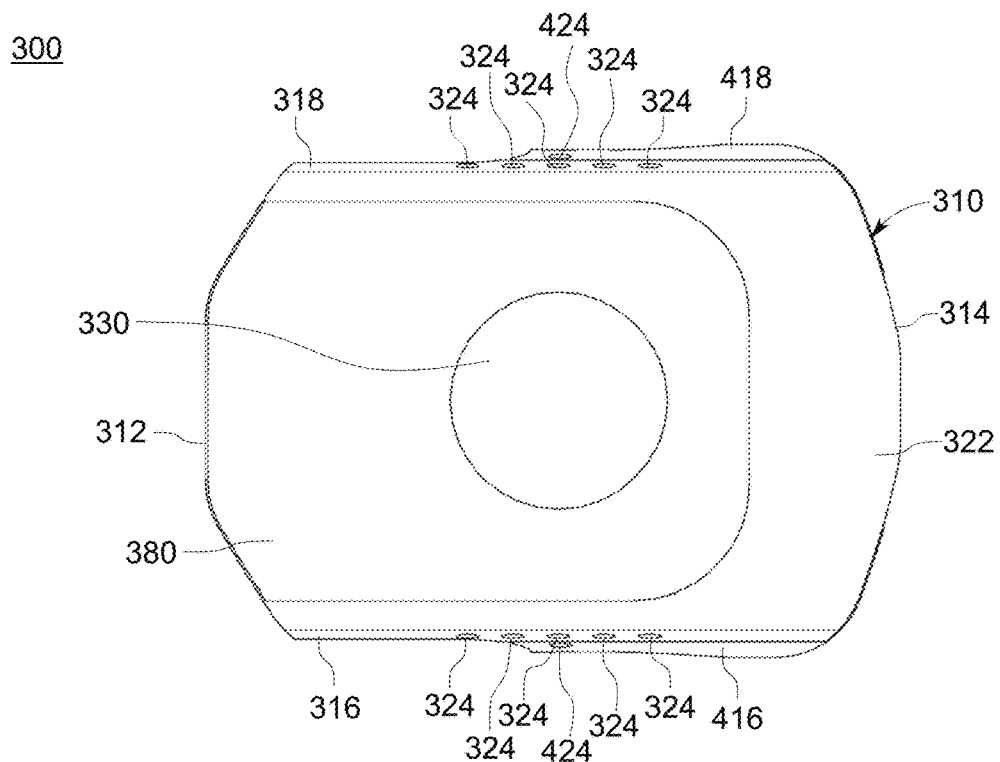
FIG. 3 is a top view of the trial insert of FIG. 1, in accordance with an aspect of the present disclosure.
Figure 4:
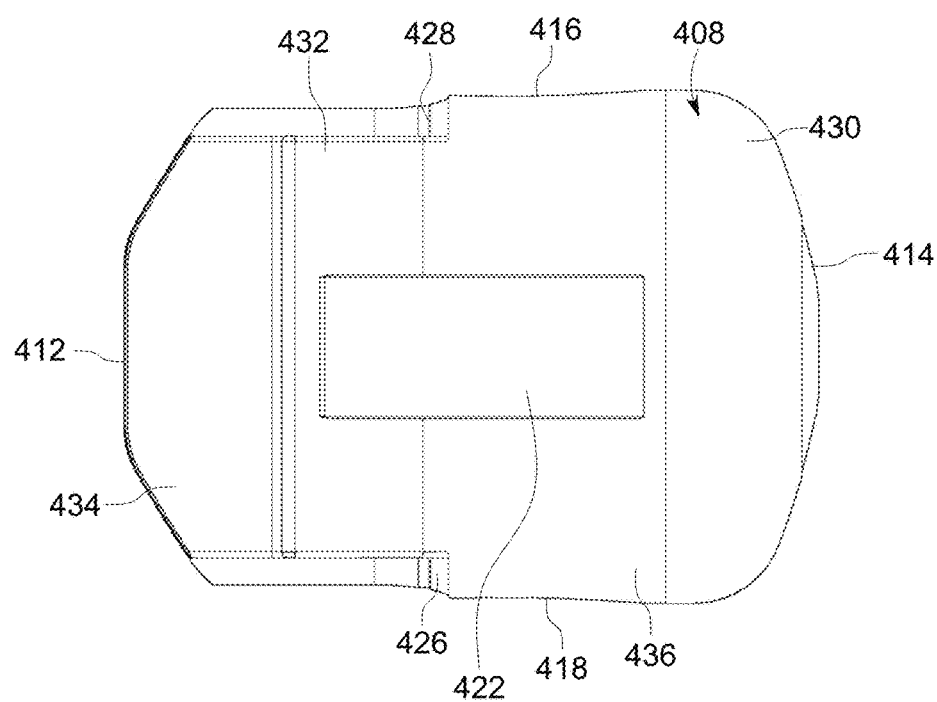
FIG. 4 is a bottom view of the trial insert of FIG. 1, in accordance with an aspect of the present disclosure.
Figure 5:
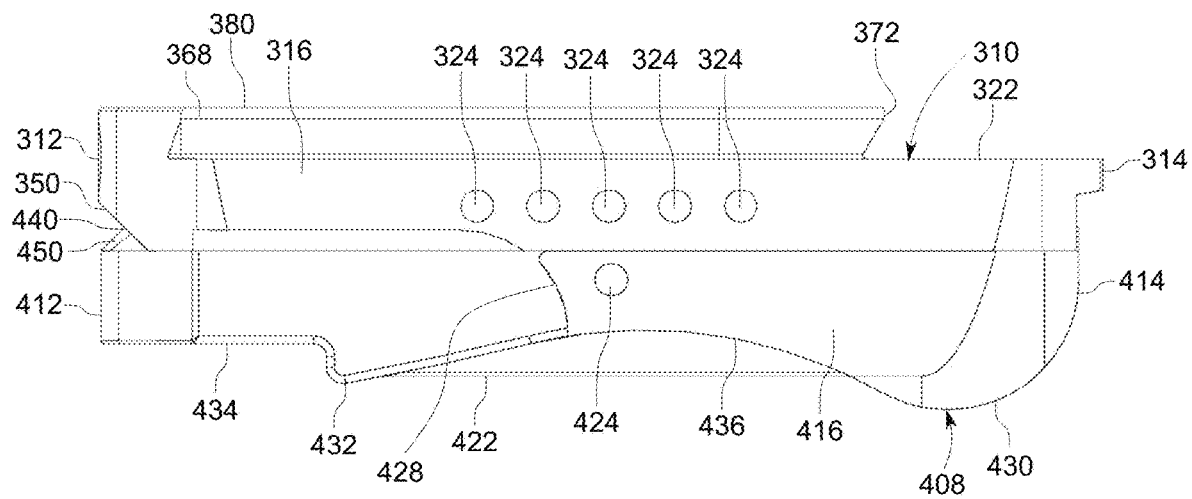
FIG. 5 is a first side view of the trial insert of FIG. 1, in accordance with an aspect of the present disclosure.
Figure 6:
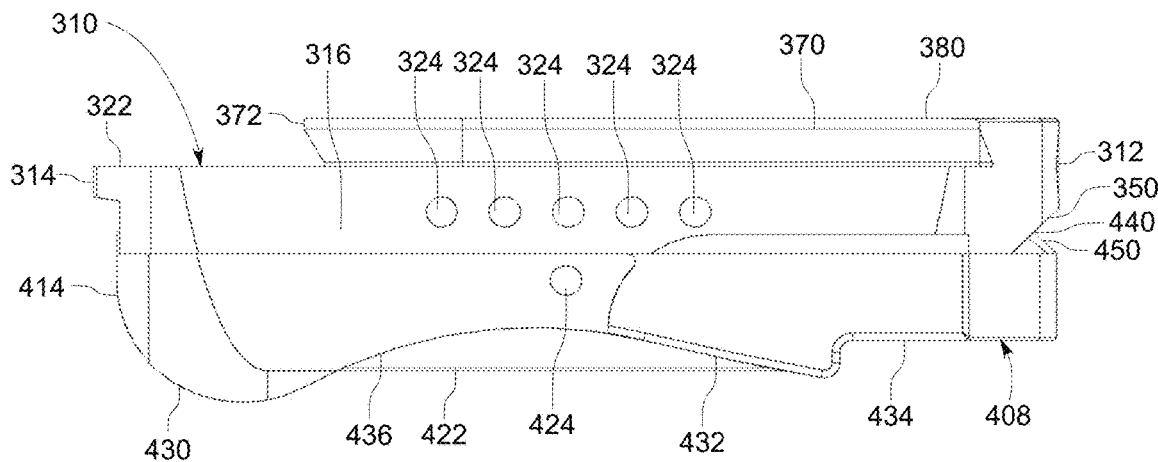
FIG. 6 is a second side view of the trial insert of FIG. 1, in accordance with an aspect of the present disclosure.
Figure 7:
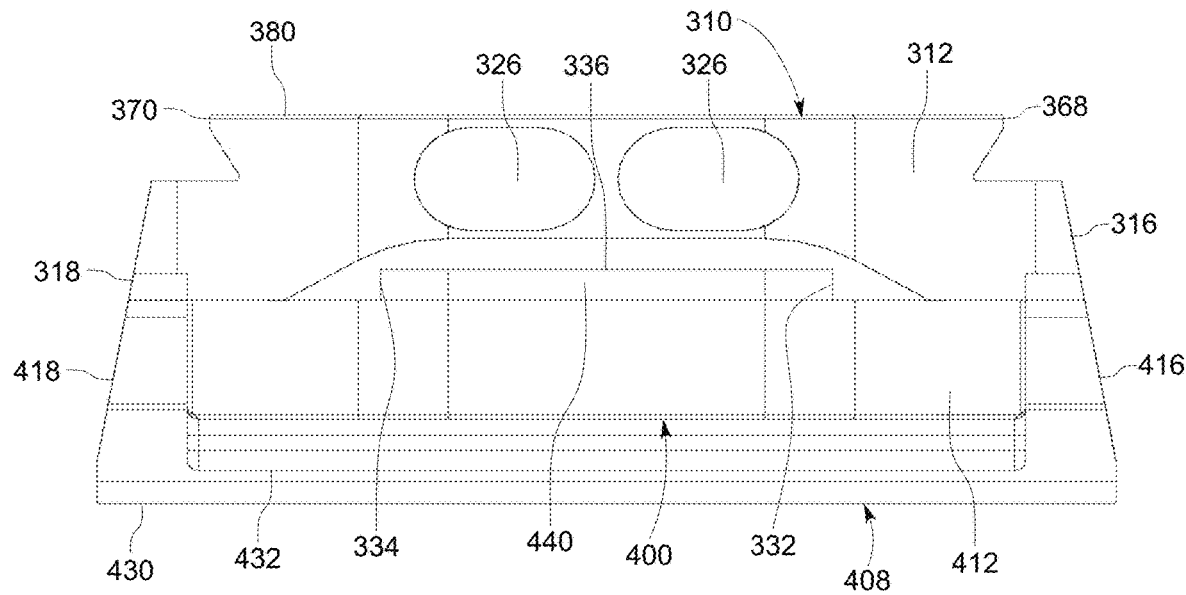
FIG. 7 is a first end view of the trial insert of FIG. 1, in accordance with an aspect of the present disclosure.
Figure 8:
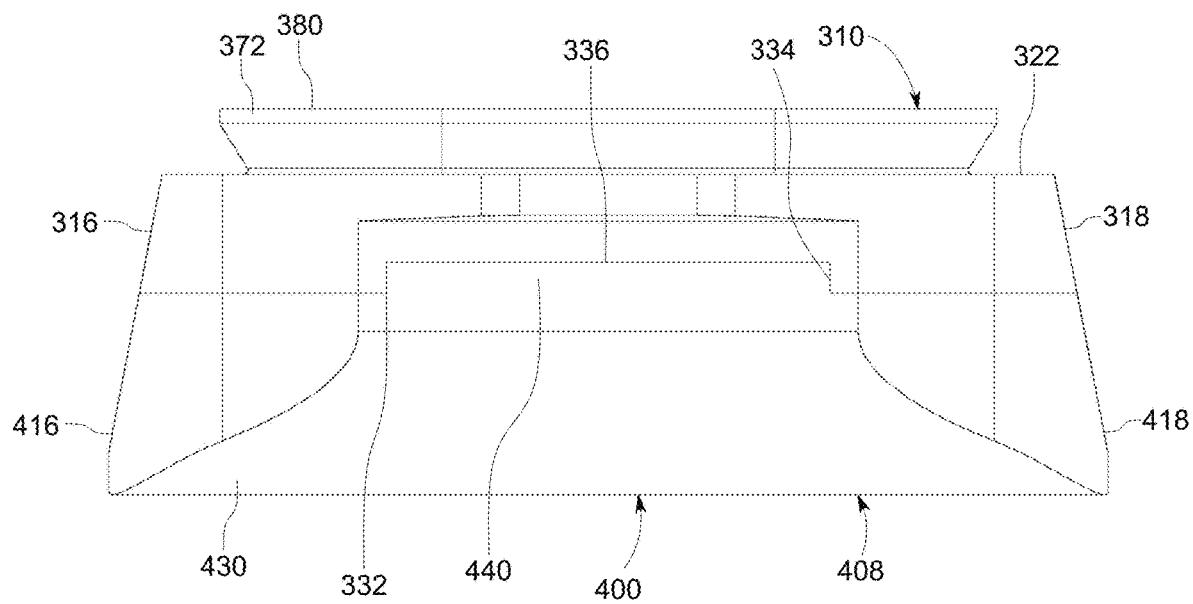
FIG. 8 is a second end view of the trial insert of FIG. 1, in accordance with an aspect of the present disclosure.
Figure 9:
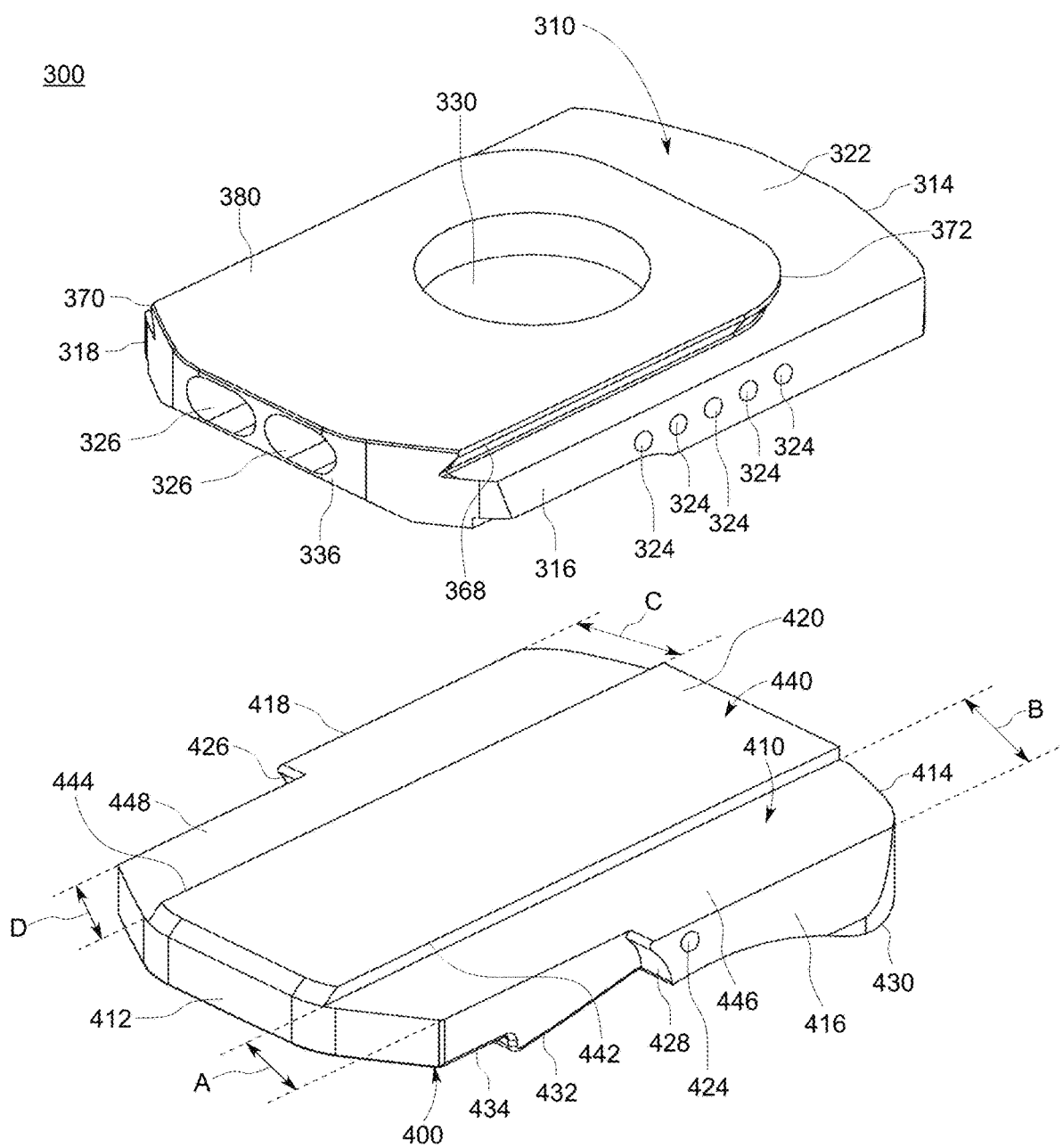
FIG. 9 is a first exploded, perspective view of the trial insert of FIG. 1, in accordance with an aspect of the present disclosure.
Figure 15:
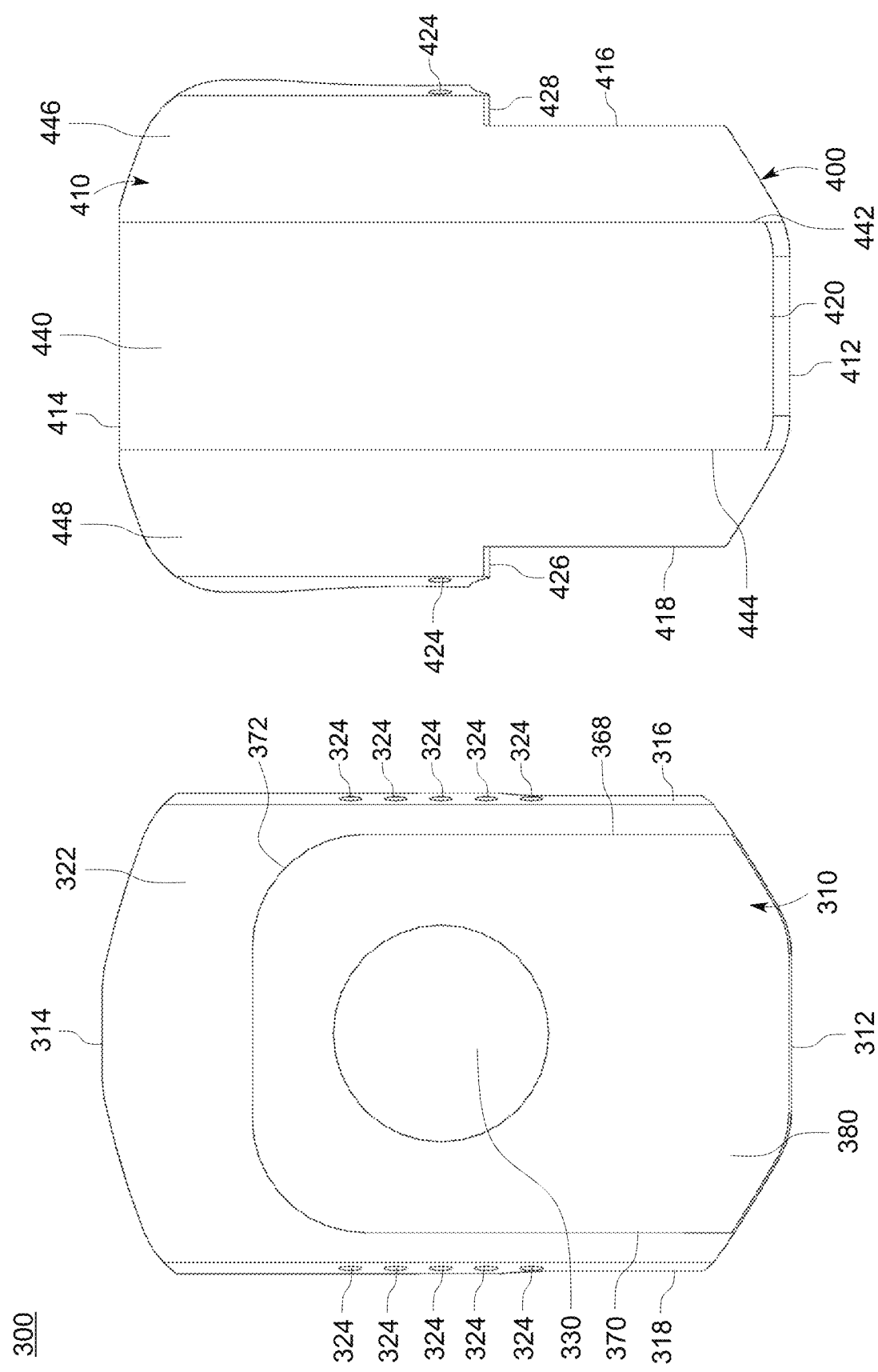
FIG. 15 is an exploded, top view of the trial insert of FIG. 1, in accordance with an aspect of the present disclosure.

The trial engagement member 380 may have, for example, engagement features along sections of the perimeter such as a first engagement feature or first male dovetail 368, a second engagement feature or second male dovetail 370, and a third engagement feature or third male dovetail 372, as shown in FIGS. 1, 3, 9, and 15. The first engagement feature 368 and the second engagement feature 370 may, for example, extend from the anterior end 312 towards the posterior end 314. The first and second engagement features 368, 370 may extend approximately parallel to each other. The male dovetail features 368, 370 may face, for example, in opposing directions towards the medial and lateral sides 316, 318, respectively, as shown in FIGS. 3 and 15. With continued reference to FIGS. 3 and 15, the third engagement feature 372 may extend, for example, approximately perpendicular to the first and second engagement features 368, 372. The third engagement feature 372 may connect or extend between the first engagement feature 368 and the second engagement feature 370 of the first member 310. The third male dovetail 372 may, for example, face the posterior end 314. The connection between the first engagement feature 368 and the third engagement feature 372 and the connection between the second engagement feature 370 and the third engagement feature 372 may, for example, be tapered, angled, squared, curved, or arced.

With reference to FIGS. 5-8 and 11-14, the trial engagement member 380 extends from the top surface 322 of the first member 310. The trial engagement member 380 may have, for example, an exemplary height of approximately 1.6 mm, although alternate heights are contemplated as would be used by one having ordinary skill in the art. The trial engagement member 380 may have, for example, a vertical bore 330 extending from the top surface of the trial engagement member 380 towards the bottom surface 348 of the first member 310. The vertical bore 330 may, for example, be approximately circular with a diameter having a range from 5 mm to 15 mm, and more specifically the diameter may be approximately 10 mm.

With reference to FIGS. 7, 8, 11, and 12, the first side 316 and the second side 318 of the first member 310 may be, for example, sloped, tapered, or angled as the sides (e.g. the first side 316 and the second side 318) extend between the top surface 322 and the bottom surface 348 of the first member 310. The angle of the first side 316 and the second side 318 from the top surface 322 may be, for example, approximately 30° to 60° extending outwards from vertical and more specifically approximately 45° outwards from vertical.

With reference to FIGS. 3, 4, 15, and 16, the first end 312 and second end 314 each have a surface that may, for example, be angled to approximately form an isosceles trapezoid or have a convex curvature.

With continued reference to FIGS. 7, 8, 11, and 12, the first end 312 is shown with at least one front opening or front bore 326, having, for example, an ovular shape or elliptical shape. In other embodiments, the at least one bore 326 may be circular. The at least one front bore 326 may be, for example, two front bores 326 positioned adjacent to each other. The two front bores 326 may be shaped and configured for use with an insertion instrument (not shown), more specifically, a forked insertion instrument (not shown). In other embodiments, there may be, for example, a single front bore 326 or more than two front bores 326.

Referring now to FIGS. 5, 6, 9, 10, 13, and 14, at least one transverse bore 324 is shown extending from the medial side 316 to the lateral side 318. The at least one transverse bore 324 may be, for example, five transverse bores 324. However, there may be embodiments with more or less than five transverse bores 324, depending on the sizes of insert trials. The transverse bores 324 may have a diameter, for example, ranging from approximately 0.25 mm to 2.0 mm and more specifically, the diameter may be 1 mm. The medial side 316 further may have a medial notch or first notch 344 extending from the medial side 316, towards the lateral side 318. The lateral side 318 may have a lateral notch or second notch 346, extending from the lateral side 318 towards the medial side 316. The first and second notches 344, 346, also extend from the first end 312 towards the second end 314.

Figure 10:
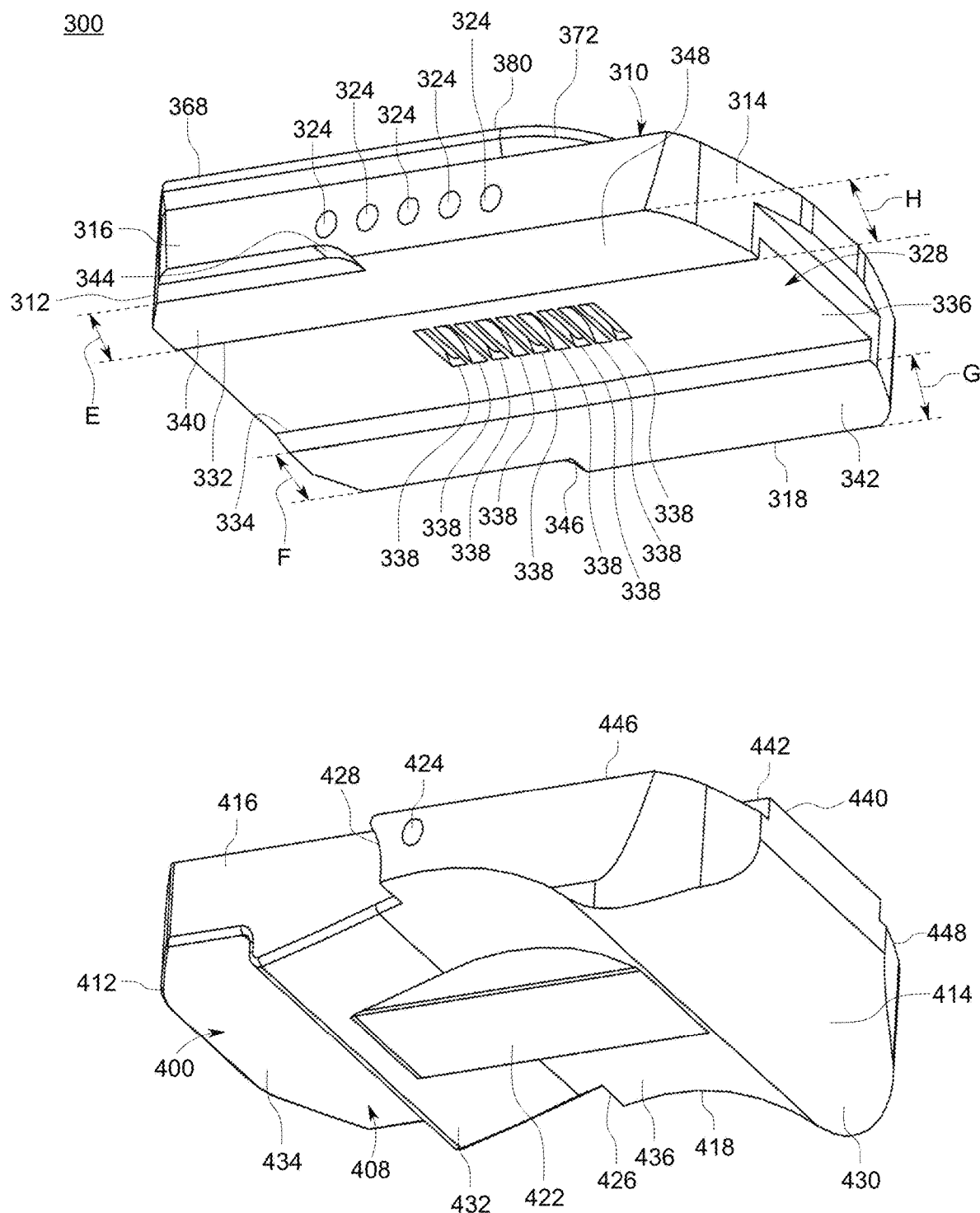
FIG. 10 is a second exploded, perspective view of the trial insert of FIG. 1, in accordance with an aspect of the present disclosure.
Figure 11:
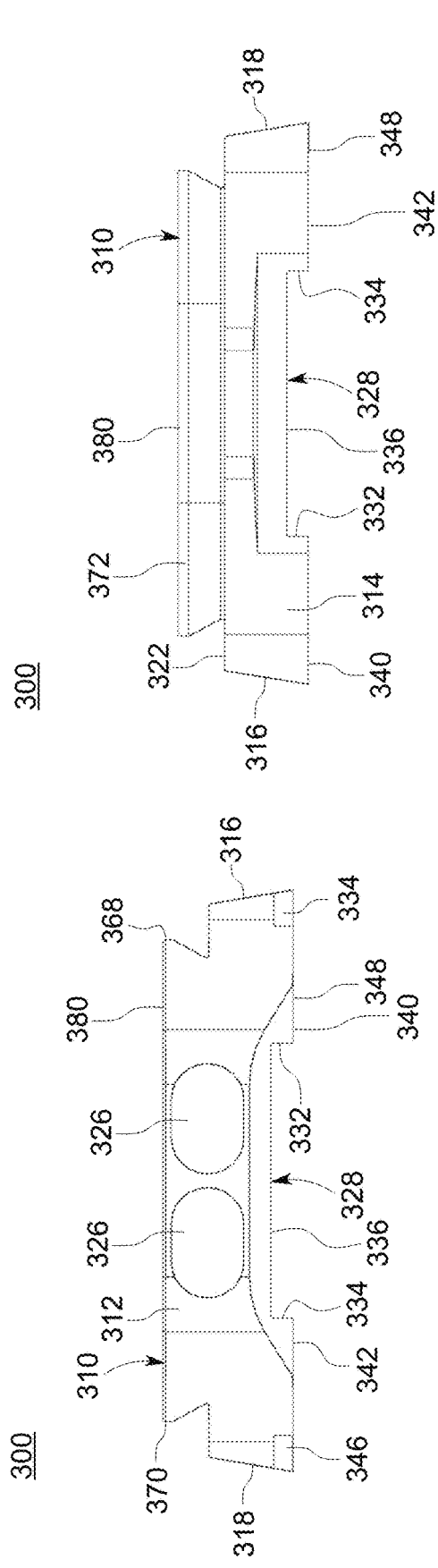
FIG. 11 is an exploded, first end view of the trial insert of FIG. 1, in accordance with an aspect of the present disclosure.
Figure 12:
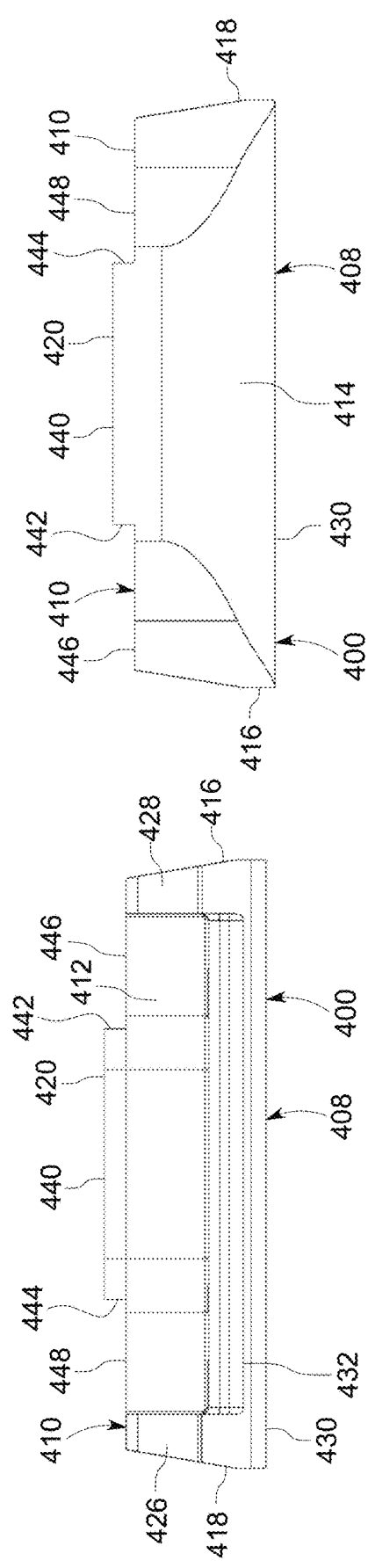
FIG. 12 is an exploded, second end view of the trial insert of FIG. 1, in accordance with an aspect of the present disclosure.
Figure 16:
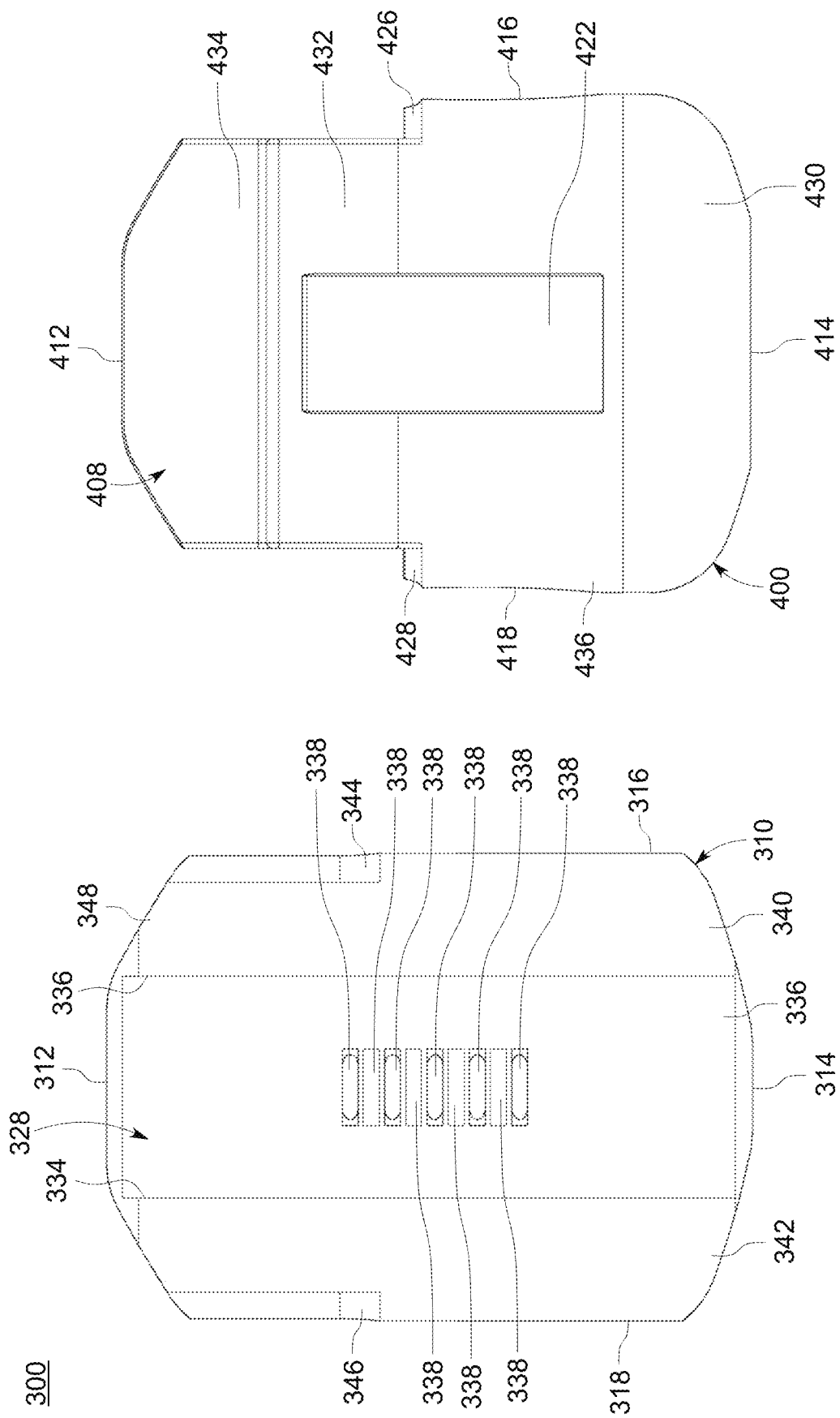
FIG. 16 is an exploded, bottom view of the trial insert of FIG. 1, in accordance with an aspect of the present disclosure.
Figure 17:
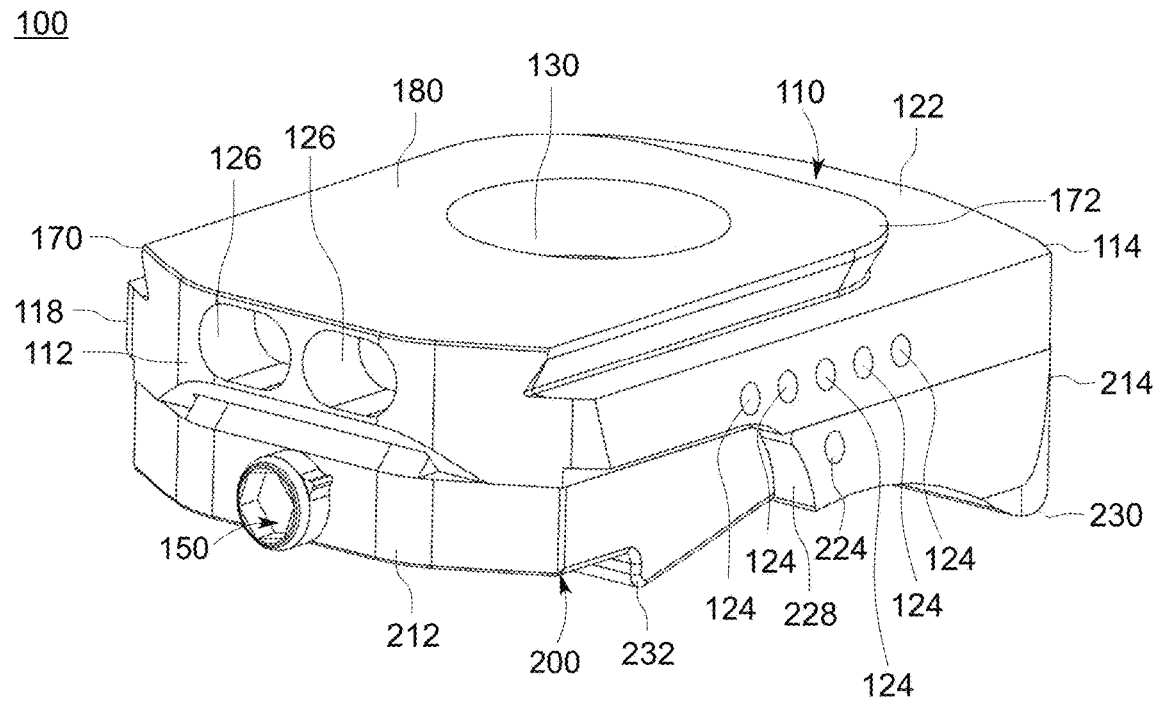
FIG. 17 is a first perspective view of another trial insert in a first position, in accordance with an aspect of the present disclosure.
Figure 18:
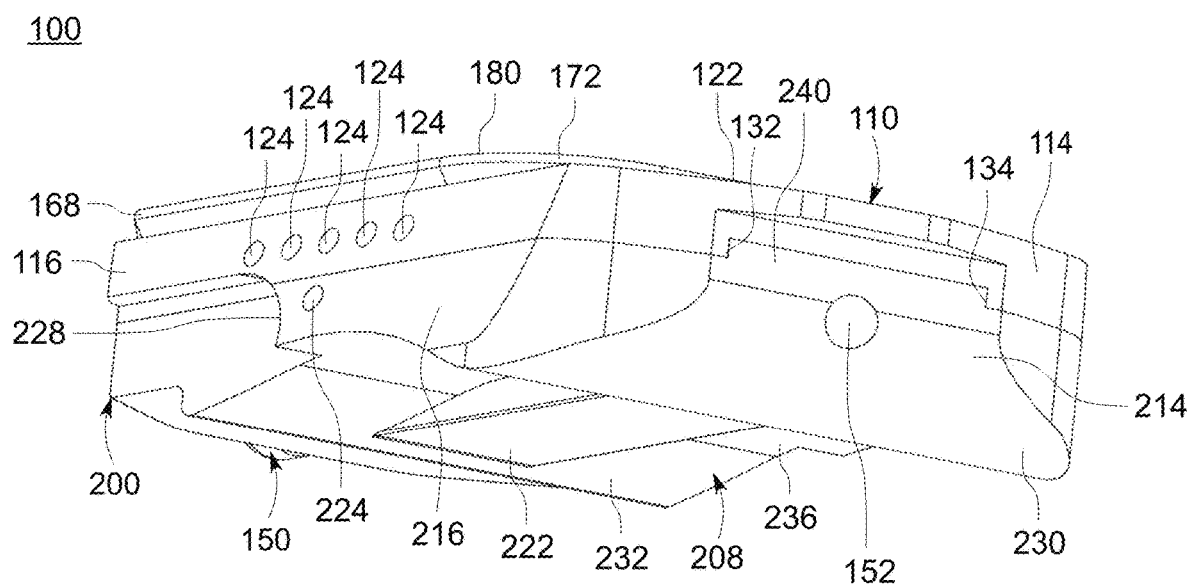
FIG. 18 is a second perspective view of the trial insert of FIG. 17, in accordance with an aspect of the present disclosure.

Referring now to FIGS. 10 and 16, the bottom surface 348 of the first member 310 is shown. The bottom surface 348 includes a recessed region or engagement region 336 extending into the first member 310 from the bottom surface 348 toward the top surface 322. The bottom surface 348 also includes an engagement slot or an engagement channel 328 extending from the first end 312 into the recessed region 336 and to the second end 314. The engagement channel 328 is bordered toward the first side 316 by a first engagement feature or first female dovetail portion 332 and bordered toward the second side 318 by a second engagement feature or second female dovetail portion 334. The engagement channel 328, first engagement feature 332, and second engagement feature 334 may have, for example, a tapered region 350 extending from the first side 312 towards the bottom surface 348, as shown in FIGS. 5, 6, 13, and 14. The recessed region 336 may have a width extending between the first and second engagement features 332, 334. The width of the recessed region 336 may, for example, range from approximately 5 mm to 15 mm and may more specifically, be approximately 10 mm wide between the first and second engagement features 332, 334. The first member 310 may come in multiple sizes for use with patients having different size bones. The engagement channel 328 of each of the first members 310 may be, for example, sized and shaped or configured to allow for replacement or exchanging of the first member 310 as needed during surgical trialing.

Referring to FIGS. 10-12 and 16, the width of the first member 310 between the first side 316 and the second side 318 at the top surface 322 may be, for example, approximately constant from the first end 312 to the second end 314. First side 316 and second side 318 may be, for example sloped out form the first member between the top surface and the bottom surface 348. Thus, the width may increase between the top surface 322 and the bottom surface 348. At the bottom surface the width of the first member 310 from the first end to the notches 344, 346 is narrower than the width of the first member 310 from the notches 344, 346 to the second end 314. The first and second engagement features 332, 334 are inset from the sides 316, 318, respectively. An inset E extends from the first engagement feature 332 to the first side 316 between the medial notch 344 and the first end 312. The inset E may be, for example, approximately 1 mm to 5 mm. An inset H extends from the first engagement feature 332 to the first side 316, between the medial notch 344 and the second end 314. The inset H may be, for example, approximately 1 mm to 7 mm. The inset E may be more specifically, approximately 4.3 mm and the inset H may be, more specifically, approximately 5.5 mm. An inset F extends from the second engagement feature 334 to the second side 318 between the lateral notch 346 and the first end 312. The inset F may be, for example, approximately 1 mm to 5 mm. An inset G extends from the second engagement feature 334 to the second side 318, between the lateral notch 346 and the second end 314. The inset G may be, for example, approximately 1 mm to 7 mm. The inset F may be more specifically, approximately 4.3 mm and the inset G may be, more specifically approximately 5.5 mm. The first engagement feature 332 and the second engagement feature 334 may be positioned, for example, approximately equidistant from the first side 316 and the second side 318, respectively.

The portion of the bottom surface 348 between the medial side 316 and the recessed region 336 is the bottom surface medial side 340. The portion of the bottom surface 348 between the lateral side 318 and the recessed region 336 is the bottom surface lateral side 342.

The bottom surface 348 of the first member 310 also includes at least one engagement slot groove or locking groove 338. The at least one locking groove 338 may be, for example, positioned within the recessed region 336. The at least one locking groove 338 may also be positioned, for example, between the anterior end 312 and the posterior end 314, as well as between the medial side 316 and the lateral side 318. The at least one locking groove 338 may be, for example, larger in the medial-lateral direction than in the anterior-posterior direction. The at least one locking groove 338 may be, for example, rectangular shaped. The at least one locking groove 338 may be, for example, nine grooves 338. However, other embodiments may have, for example, more or less than nine locking grooves 338, based on the size of the trial insert 300 and the corresponding size of the patient's tibia and talus. With continued reference to FIGS. 10 and 16, the at least one locking groove 338 may be, for example, aligned with or intersect with at least one transverse bore 324. However, if the number of locking grooves 338 is greater than the number of transverse bores 324, only some of the locking grooves may, for example, intersect with transverse bores.

Referring now to FIGS. 1-16, the second member, base member, or articulating member 400 has a first end or anterior end 412 opposite a second end or posterior end 414. The second member 400 also has a first side or medial side 416 opposite a second side or lateral side 418. In addition, the second member 400 has the top surface 410 opposite the articulated surface 408. The second member 400 may have, for example, a first notch 428 in the first side 416, extending towards the second side 418, and a second notch 426 in the second side 418, extending towards the first side 416. The notches 428, 426 may extend from the first end 412 towards the second end 414, as shown in FIGS. 15 and 16. The first end 412 and second end 414 each have a surface that may, for example, be angled to approximately form an isosceles trapezoid or have a convex curvature.

As shown in FIGS. 7, 8, 11, and 12, the sides (e.g. the first side 416 and the second side 418) may be angled, for example, approximately 30° to 60° outward from the vertical and more preferably, approximately 45° as the first side 416 and the second side 418 extend away from the top surface 410 to the articulated surface 408.

Referring to FIGS. 11, 12, 15, and 16, the medial side 416 and the lateral side 418 have notches 428, 426 extending from the anterior side 412 towards the posterior side 414. The notches 428, 426 further extend, for example, from the top surface 410 to the articulated surface 408 and may be vertical, between the top surface 410 and the bottom surface 408. The first notch 428 may, for example, have the same angle as the first side 416 between the top surface 410 and the articulated surface 408. The second notch 426 may, for example, have the same angle as the second side 418 between the top surface 410 and the articulated surface 408. However, the first notch 428 and the second notch 426 may have angles that differ from the first side 416 and second side 418, respectively, with angles ranging from vertical to 60° from the top surface 410 to the articulated surface 408. The sides (e.g. the medial side 416 and the lateral side 418) further have a transverse bore 424 extending from the medial side 416 to the lateral side 418. The transverse bore 424 may have, for example, a diameter ranging from approximately 0.25 mm to 2.0 mm and more specifically, a diameter of approximately 1 mm.

As shown in FIGS. 9 and 11-15, the top surface 410 of the second member 400 includes a raised section or engagement member 440 raised out from the top surface 410 and extending from the anterior end 412 to the posterior end 414. The engagement member 440 has a first engagement feature or first male dovetail 442 inset from the medial side 416, and a second engagement feature or second male dovetail 444 inset from the lateral side 418. The engagement member 440 is positioned between a medial top surface 446 and a lateral top surface 448. The first engagement feature 442 and the second engagement feature 444 extend from the first end 412 towards the second end 414. An inset A extends along the medial top surface 446 from the first engagement feature 442 to the first side 416, between the medial notch 428 and the first end 412. The inset A may be, for example, approximately 1 mm to 5 mm. An inset B extends along the medial top surface 446 from the first engagement feature 442 to the first side 416, between the medial notch 428 and the second end 414. The inset B may be, for example, approximately 1 mm to 7 mm. The inset A may be more specifically, approximately 4.3 mm and the inset B may be, more specifically, approximately 5.5 mm. An inset D extends along the lateral top surface 448 from the second engagement feature 444 to the second side 418, between the lateral notch 426 and the first end 412. The inset D may be, for example, approximately 1 mm to 5 mm. An inset C extends along the lateral top surface 448 from the second engagement feature 444 to the second side 418, between the lateral notch 426 and the second end 414. The inset C may be, for example, approximately 1 mm to 7 mm. The inset D may be more specifically, approximately 4.3 mm and the inset C may be, more specifically, approximately 5.5 mm. The engagement member 440, the first engagement feature 442, and the second engagement feature 444 may have, for example, a tapered region 450 extending from the first side 412 towards the engagement member top surface 420, as shown in FIGS. 5, 6, 13, and 14. The engagement member 440 is configured, shaped and dimensioned, for engagement with the engagement slot 328 of the first member 310.

As shown in FIGS. 10-14 and 16, the articulated surface 408 of the second member 400 includes a first segment 434, a second segment 432, a third segment 436, a fourth segment 430, and a trial engagement member 422. The first segment 434 extends from the first end 412 towards the second end 414 and may have, for example, a planar surface. The second segment 432 may have a triangular or wedge shape from a side view. The second segment 432 may extend, for example, from an end of the first segment 434, generally perpendicular to the articulated surface 408 forming a first portion of the second segment 432. The first portion of the second segment 432 may extend away from the articulated surface 408, for example, approximately 1 mm, although alternate distances are contemplated as would be known by one having ordinary skill in the art. From the free end of the first portion, the second segment 432 may, for example, curve or angle towards the top surface 410 and the second end 414 forming a second portion. The second portion of the second segment 432 may form, for example, a hypotenuse that connects to the third segment 436. The hypotenuse portion may be, for example, approximately 2.6 mm or greater, and more specifically, have a linear distance of approximately 4.75 mm. The third segment 436 extends from an end of the second segment 432 towards the second end 414 of the second member 400 and connects with the fourth segment 430. The third segment 436 may, for example, be approximately parallel to the top surface 410 or have a concave curvature between the second segment 432 and the fourth segment 430. The third segment 436 may be, for example, curved in the direction of a longitudinal axis extending from the first end 412 to the second end 414. The fourth segment 430 may have, for example, a convex curvature extending from the third segment 436 to the second end 414. The fourth segment 430 may be, for example, curved in the direction of the longitudinal axis.

As further shown in FIGS. 10-14, and 16, the trial engagement member 422 extends from the articulated surface 408 outwards, forming a raised structure extending from the second segment 432 to the third segment 436. The trial engagement member 422 further has a length which may be, for example, approximately perpendicular to the first end 412 and the second end 414. The trial engagement member 422 has a width which may be, for example, approximately perpendicular to the first side 416 and the second side 418. The trial engagement member 422 may have, for example, a length larger than the width. The trial engagement member 422 may have, for example, an exemplary length of approximately 14 mm, although alternate distances are contemplated as would be known by one having ordinary skill in the art. The trial engagement member 422 may have, for example, an exemplary width of approximately 6 mm, although alternate distances are contemplated as would be known by one having ordinary skill in the art. The trial engagement member 422 further has a bottom surface which may be, for example, a planar surface the extends parallel with the engagement member top surface 420.

The trial insert 300 is configured (e.g. shaped and dimensioned) for engagement with a tibial trial component or a tibial implant (not shown) at the trial engagement member 380, engagement between the first member 310 and the second member 400, and engagement between the second member 400 and a talar trial component or a talar implant (not shown). The first, second, and third engagement features 368, 370, 372, of the trial engagement member 380, engage with a tibial trial component (not shown) and/or a tibial implant (not shown), providing a fixed support for the first member 310 of the trial insert 300. The engagement member 440 and the engagement slot 328 are engaged at the first engagement features 332, 442 (e.g. female and male dovetail portions) and at the second engagement features 334, 444 (e.g. female and male dovetail portions) providing a linkage for movement of the first member 310 and the second member 400, relative to each other, and provides for relative position translation along the interface between the engagement slot 328 and the engagement member 400, in the anterior/posterior direction. However, since the first member 310 may be, for example, connected to the tibial trial component (not shown), the second member 200 is moveable along the engagement member 440 within the engagement slot 328, in the anterior/posterior direction relative to the first member 310. The second member 400 engages with the talar trial component (not shown) and/or a talar implant (not shown) along the articulated surface 408, such that plantar flexion, neutral, and dorsiflexion motions may be simulated, and the positions of the trial insert 300 refined by further positioning the first member 310 relative to the second member 400.

Referring now to FIGS. 17-37, another trial insert 100 is shown. The implant 100 includes a first member or movable member 110, a second member or base member 200, and a locking screw 150. The first member 110 includes a top surface 122 opposite a bottom surface 148. The second member 200 includes a top surface 210 opposite a bottom surface or an articulating surface 208. The top surface 210 of the second member 200 removably connects to the first member 110 and the bottom surface 148 engages the second member 200. The first member 110 and the second member 200 may come in multiple sizes for use with patients having different size tibia and talus bones and requiring different sizes of trials.

As shown in FIGS. 25-32, the first member 110 includes a first end or anterior end 112 opposite a second end or posterior end 114. The distance between the first end 112 and the second end 114 may be, for example, from approximately 28 mm to 42 mm, and more specifically, approximately 30 mm. The first member 110 also includes a first side or medial side 116 opposite a second side or lateral side 118. The distance between the first side 116 and the second side 118 may, for example, approximately range from 20 mm to 34 mm, and more specifically, may be approximately 20 mm. The top surface 322 includes a bone trial connector, a trial engagement member, or a prosthetic engagement member 180, extending from the anterior end 112 towards the posterior end 114 and inset from the posterior end 114, as shown in FIGS. 19, 21, 22, and 29-31. The trial engagement member 180 may be inset from the second end 114, for example, approximately 4 mm to 8 mm, and more specifically approximately 7 mm. In addition, the trial engagement member 180 may be, for example, inset approximately 0 mm to 5 mm, more specifically, approximately 0 mm to 3 mm, from the first side 116 and the second side 118 respectively, and, yet more specifically inset approximately 1.8 mm from the first side 116 and the second side 118, as shown in FIGS. 23, 24, 27 and 28. The insets from the first side 116 and the second side 118 of the trial engagement member 180 also may be, for example, approximately equidistant. In an alternative embodiment, the trial engagement member 180 may, for example, extend between the first side 116 and the second side 118 and from the anterior end 112 to the posterior end 114.

Figure 19:
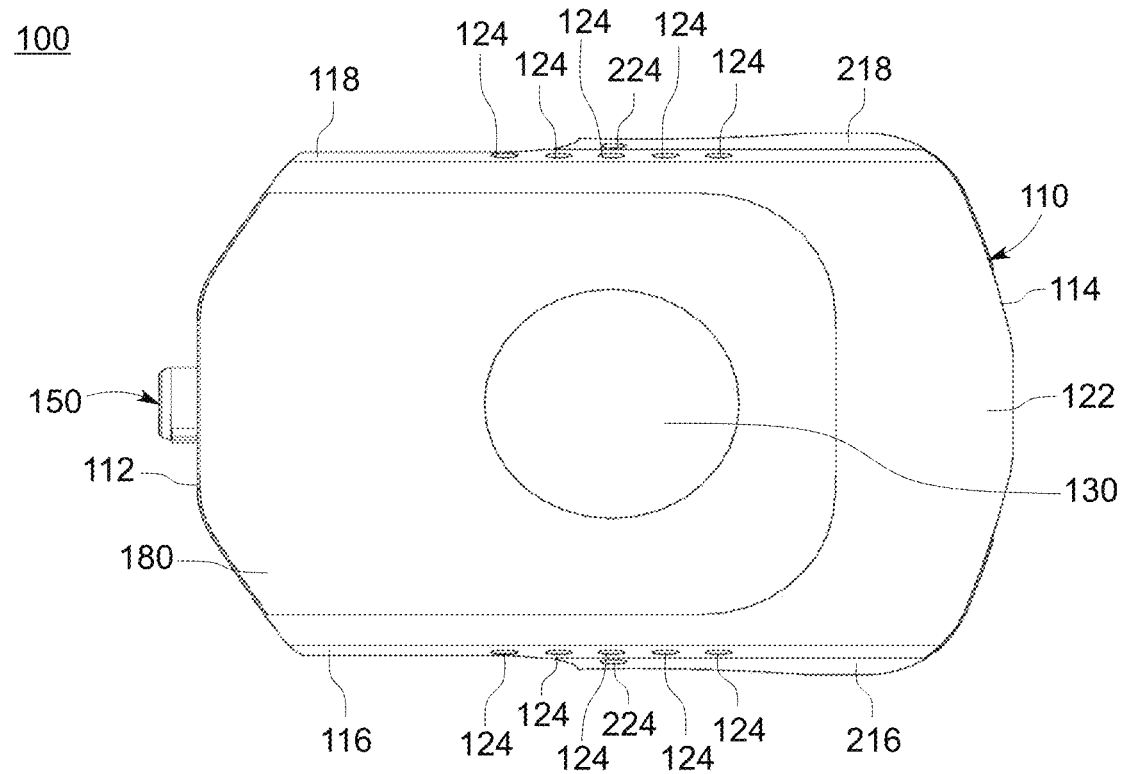
FIG. 19 is a top view of the trial insert of FIG. 17, in accordance with an aspect of the present disclosure.
Figure 20:
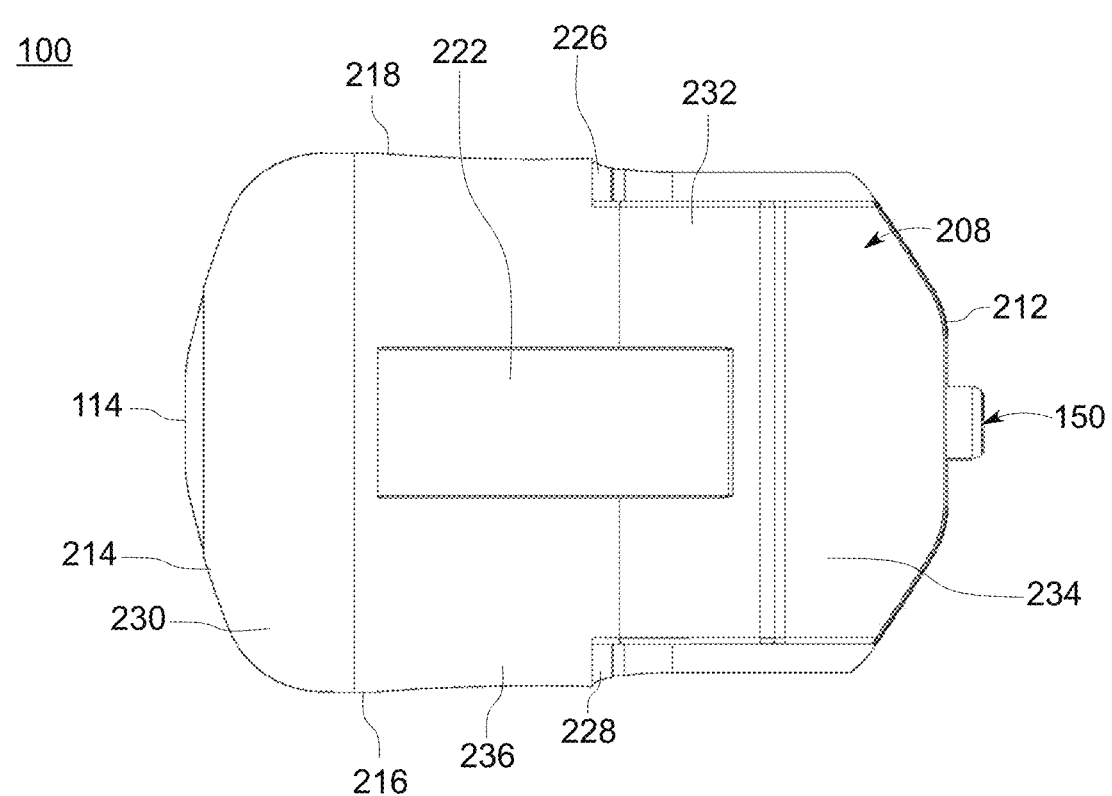
FIG. 20 is a bottom view of the trial insert of FIG. 17, in accordance with an aspect of the present disclosure.
Figure 21:
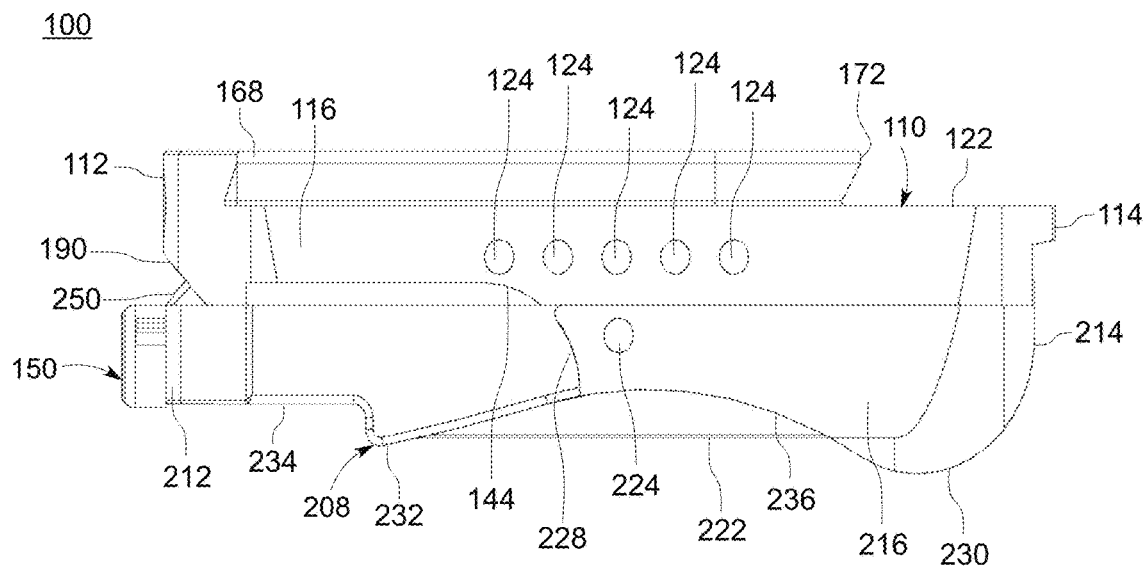
FIG. 21 is a first side view of the trial insert of FIG. 17, in accordance with an aspect of the present disclosure.
Figure 22:
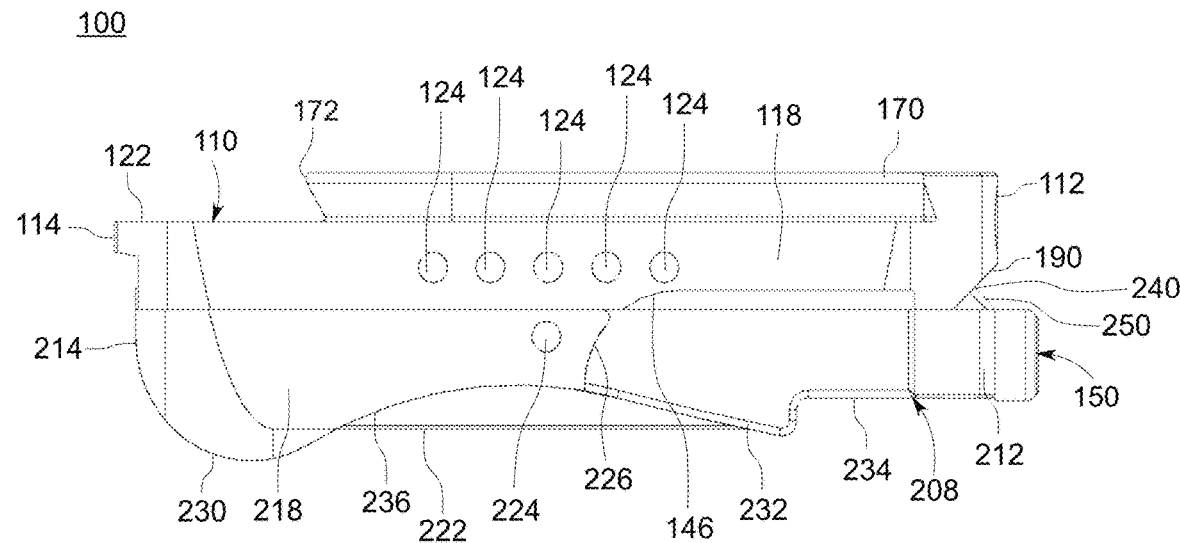
FIG. 22 is a second side view of the trial insert of FIG. 17, in accordance with an aspect of the present disclosure.
Figure 23:
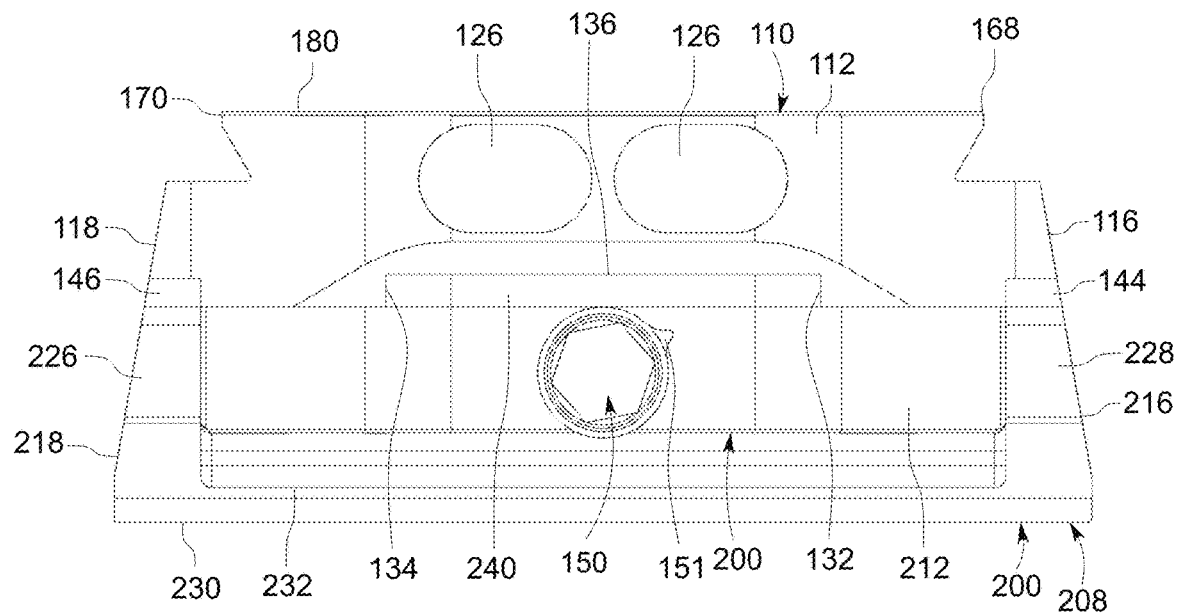
FIG. 23 is a first end view of the trial insert of FIG. 17, in accordance with an aspect of the present disclosure.
Figure 24:
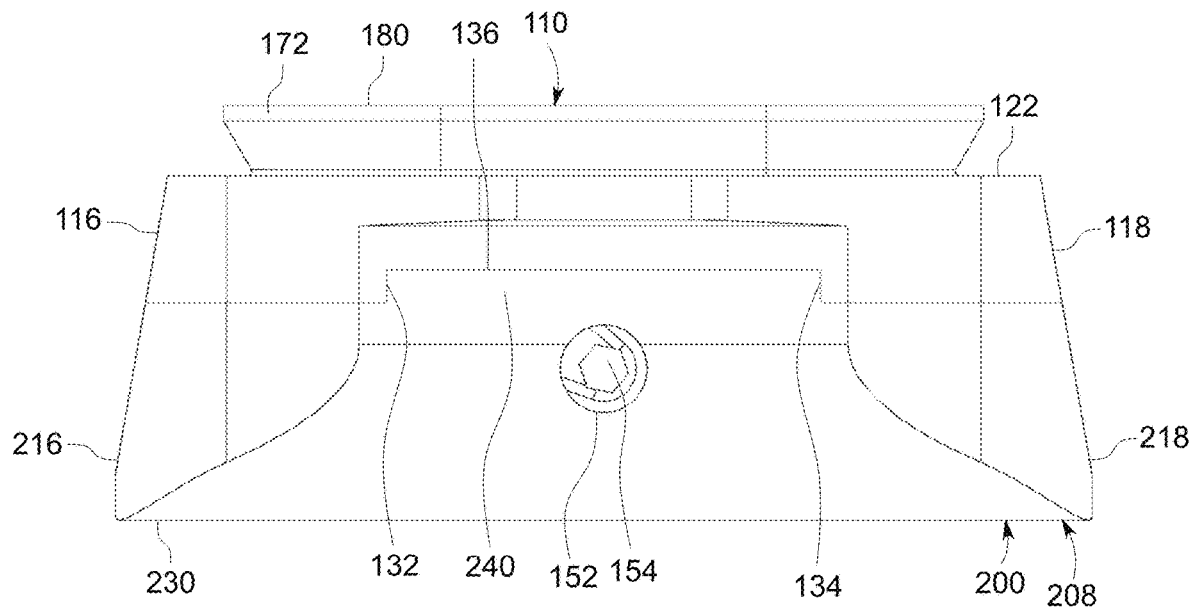
FIG. 24 is a second end view of the trial insert of FIG. 17, in accordance with an aspect of the present disclosure.
Figure 31:
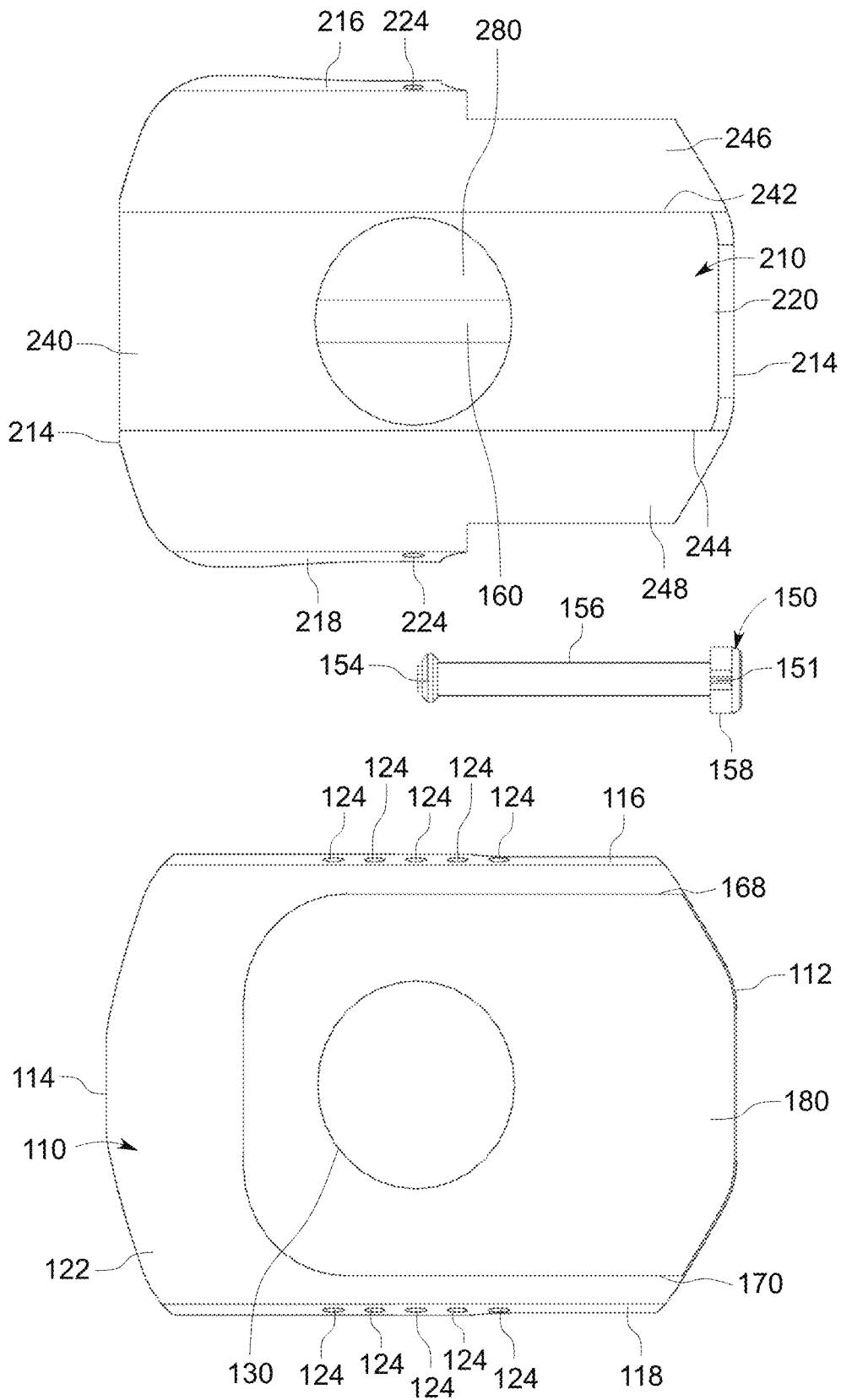
FIG. 31 is an exploded, top view of the trial insert of FIG. 17, in accordance with an aspect of the present disclosure.

The trial engagement member 180 may have, for example, engagement features along sections of the perimeter such as a first engagement feature or first male dovetail 168, a second engagement feature or second male dovetail 170, and a third engagement feature or third male dovetail 372, as shown in FIGS. 17, 19, 25, and 31. The first engagement feature 168 and the second engagement feature 170 may, for example, extend from the anterior end 112 towards the posterior end 114 and the first and second engagement features 168, 170 may extend approximately parallel to each other. The male dovetail features 168, 170 may face in opposing directions towards the medial and lateral sides, 116 and 118, respectively, as shown in FIGS. 19 and 31. With continued reference to FIGS. 19 and 31, the third engagement feature 172 may extend, for example, approximately perpendicular to and connected to the first engagement feature 168 and the second engagement feature 170. The third male dovetail 172 may, for example, face the posterior end 114 of the first member 110. The connection between the first engagement feature 168 and the third engagement feature 172 and the connection between the second engagement feature 170 and the third engagement feature 172 may, for example, be tapered, angled, squared, curved, or arced.

With reference to FIGS. 21-24 and 27-30, the trial engagement member 180 may, for example, extend away from the top surface 122 of the first member 110, to an exemplary embodiment height of approximately 1.6 mm, although alternate heights are contemplated as would be used by one having ordinary skill in the art. The trial engagement member 180 may have, for example, a vertical bore 130 extending from the top surface 122 of the trial engagement member 180 towards the bottom surface 148 of the first member 110. The vertical bore 130 may be, for example, approximately circular with a diameter ranging from approximately 5 mm to 15 mm, and more specifically, have a diameter of 10 mm.

With reference to FIGS. 23, 24, 27, and 28, the first side 116 and the second side 118 of the first member 110 may be, for example, sloped, tapered, or angled as the sides (e.g. the first side 116 and the second side 118) extend between the top surface 122 and the bottom surface 148 of the first member 110. The angle of the first side 116 and the second sides 118 extending from the top surface 122 to the bottom surface 148 may be, for example, approximately 30° to 60° extending outwards from vertical and more specifically approximately 45° outwards from vertical.

With reference to FIGS. 19, 20, 31, and 32, the first end 112 and second end 114 each have a surface that may, for example, be angled to approximately form an isosceles trapezoid or to have a convex curvature.

With continued reference to FIGS. 23, 24, 27, and 28, the first end 112 is shown with at least one front opening or front bore 126 having, for example, an ovular shape or elliptical shape. In other embodiments, the at least one bore 126 may be circular. The at least one front bore 126 may be, for example, two front bores. In other embodiments there may be, for example, a single front bore or more than two front bores. The two front bores 126 may be shaped and configured for use with an insertion instrument (not shown), more specifically, a forked insertion instrument (not shown).

Referring now to FIGS. 21, 22, 25, 26, 29, and 30, at least one transverse bore 124 is shown extending from the medial side 116 to the lateral side 118. The at least one transverse bore 124 may be, for example, five transverse bores. However, there may be embodiments with more or less than five transverse bores for use with patients having different sizes of tibia and tibial bones. The medial side 116 further has a medial notch or first notch 144 extending from the medial side 116 towards the lateral side 118. The lateral side 118 has a lateral notch or second notch 146 extending from the lateral side 118 towards the medial side 116. The first and second notches, 144, 146, also extend from the first end 112 towards the second end 114. The transverse bores 124 may have a diameter of, for example, approximately from 0.25 mm to 2.0 mm, and more specifically approximately 1 mm.

Figure 26:
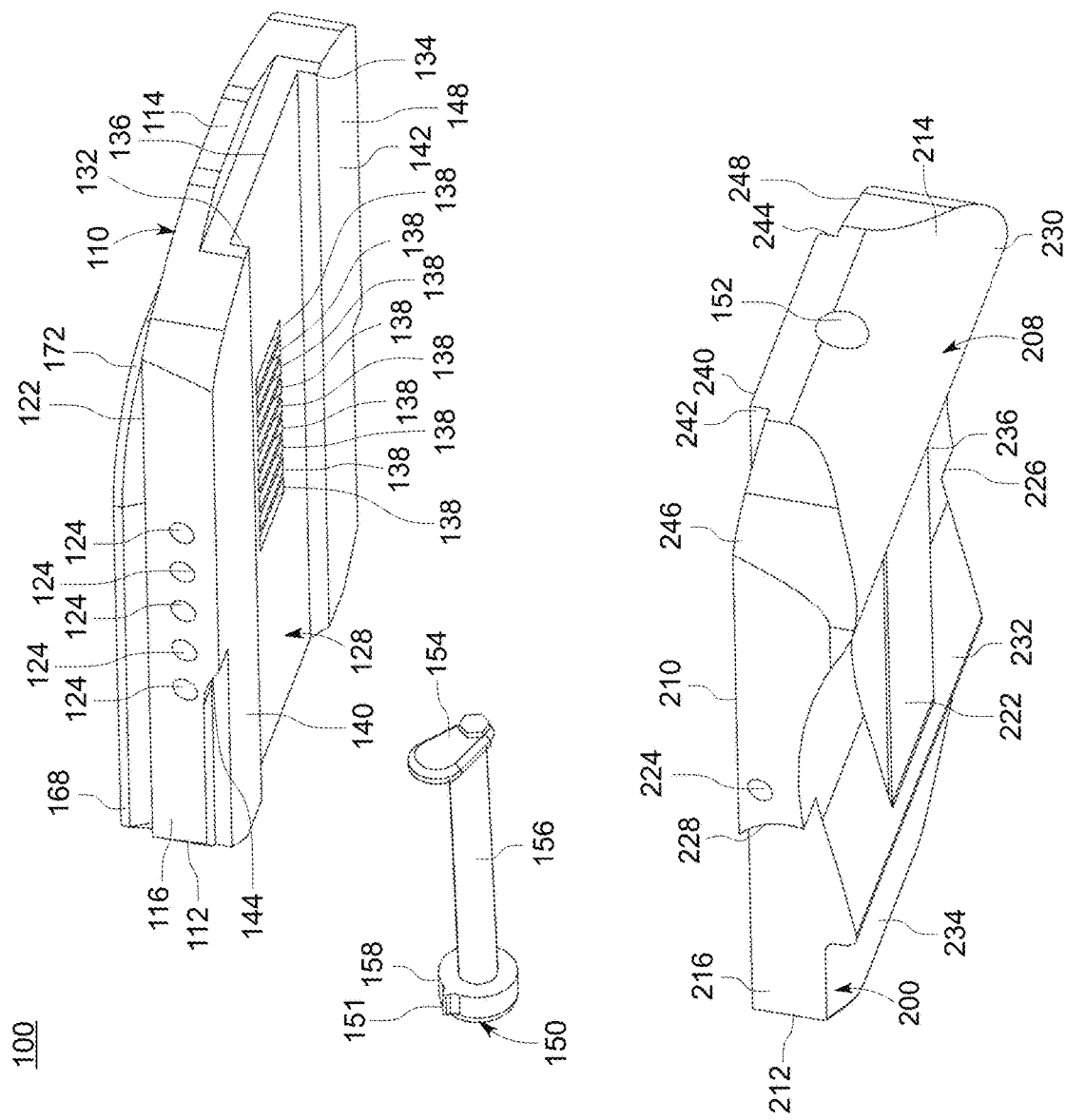
FIG. 26 is a second exploded, perspective view of the trial insert of FIG. 17, in accordance with an aspect of the present disclosure.
Figure 32:
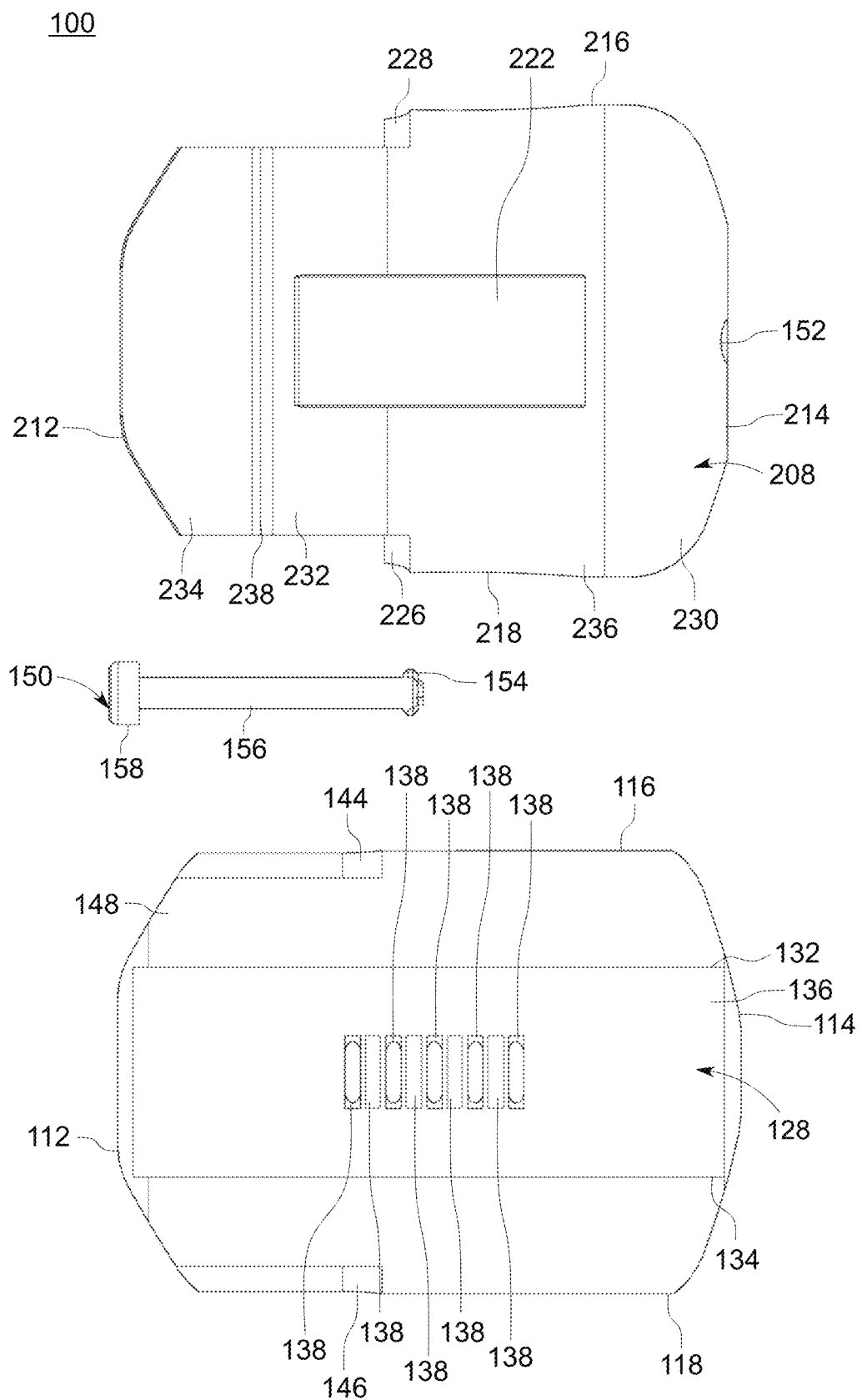
FIG. 32 is an exploded, bottom view of the trial insert of FIG. 17, in accordance with an aspect of the present disclosure.
Figure 33:
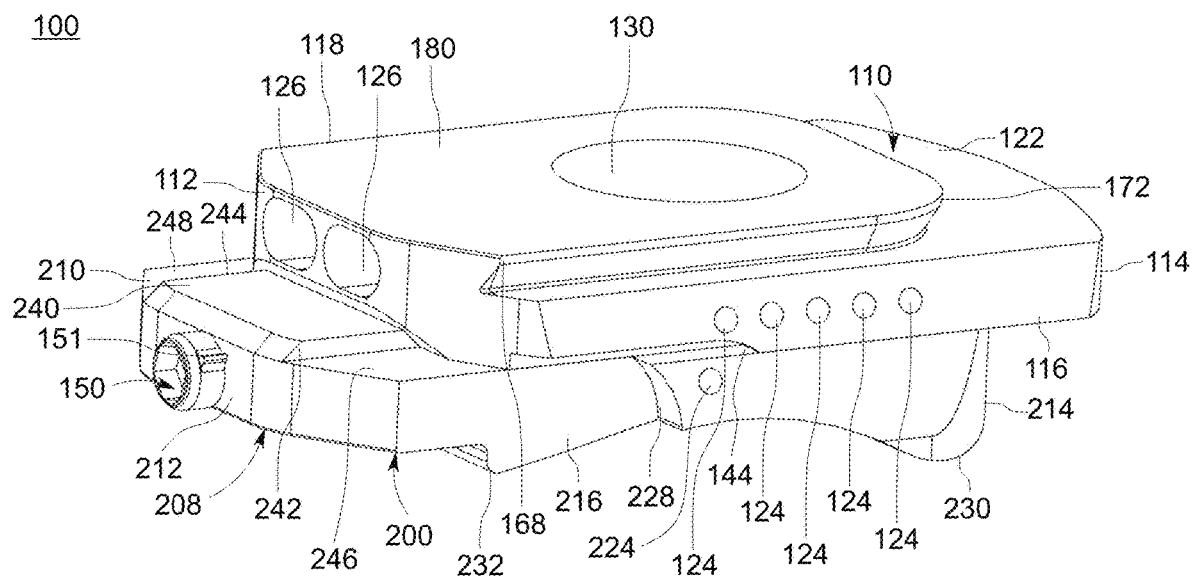
FIG. 33 is a first perspective view of the trial insert of FIG. 17 in a second position, in accordance with an aspect of the present disclosure.
Figure 34:
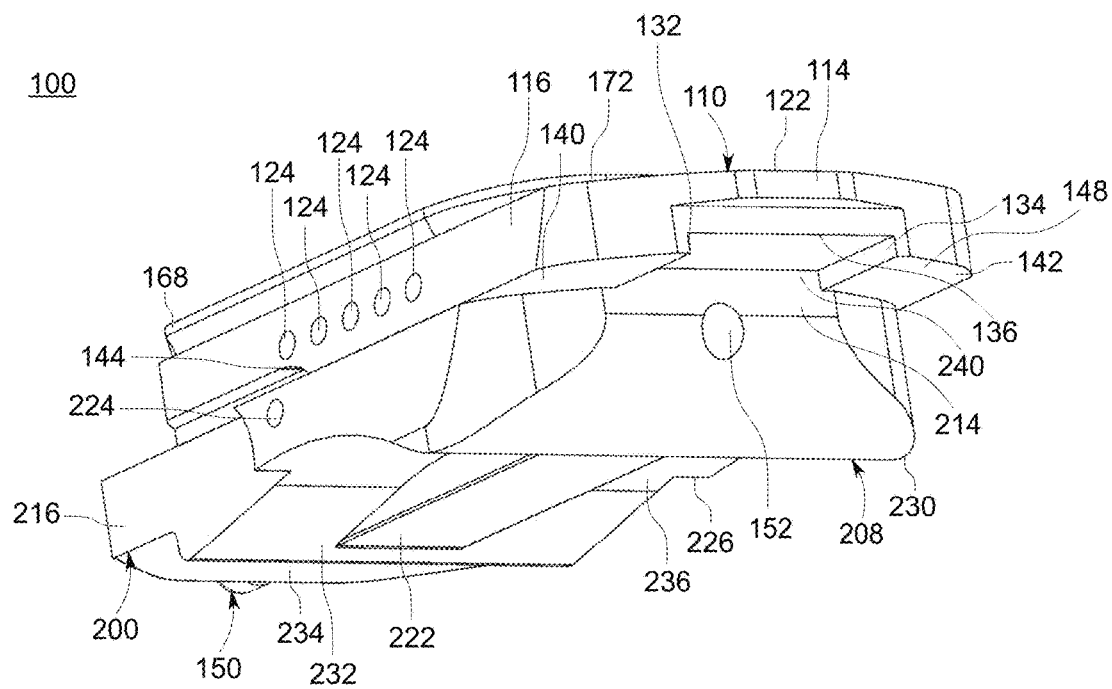
FIG. 34 is a second perspective view of the trial insert of FIG. 33, in accordance with an aspect of the present disclosure.
Figure 35:
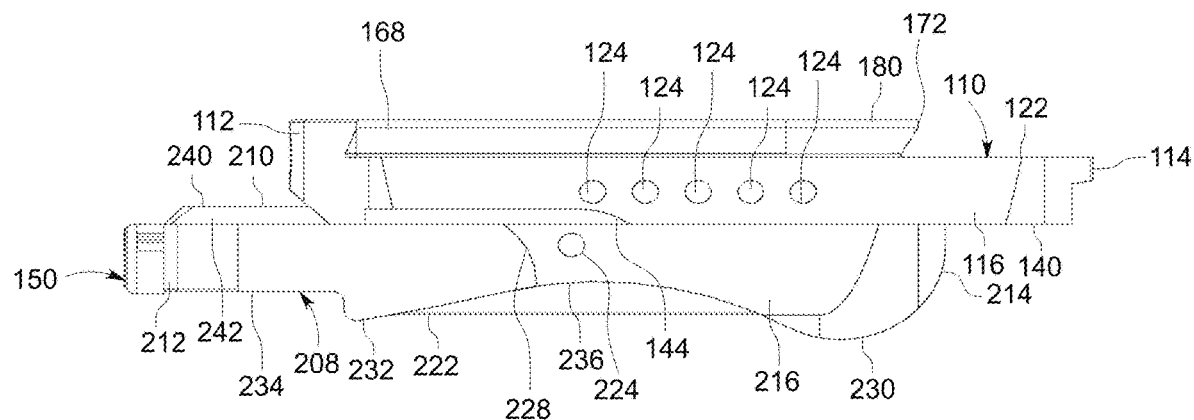
FIG. 35 is a first side view of the trial insert of FIG. 33, in accordance with an aspect of the present disclosure.
Figure 36:
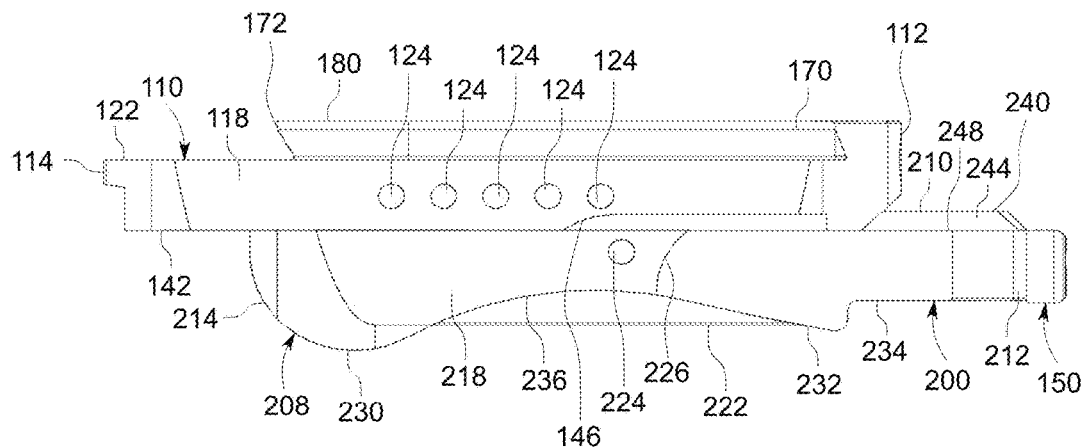
FIG. 36 is a second side view of the trial insert of FIG. 33, in accordance with an aspect of the present disclosure.

Referring now to FIGS. 26 and 32, the bottom surface 148 of the first member 110 is shown. The bottom surface 148 includes a recessed region or engagement region 136 extending into the first member 110 from the bottom surface 148 toward the top surface 122. The bottom surface 148 also includes an engagement slot or an engagement channel 128 extending from the first end 112 to the second end 114 and into the recessed region 136. The engagement channel 128 is bordered toward the first side 116 by a first engagement feature or first female dovetail portion 132 and bordered toward the second side 118 by a second engagement feature or second female dovetail portion 134. The engagement channel 128, first engagement feature 132, and second engagement feature 134 may have, for example, a tapered region 190 extending from the first side 112 towards the bottom surface 148, as shown in FIGS. 21, 22, 29, and 30. The recessed region 136 may have a width between the first and second engagement features 132, 134 of, for example, approximately 5 mm to 15 mm, and more specifically, approximately 10 mm. The first member 110 may come in multiple sizes for use with patients requiring different sized trials or implants. In addition, the engagement channel 128 of every first member 110 may be, for example, sized and shaped to allow for replacement or exchanging of the first member 110 as needed.

Referring to FIGS. 26-28 and 32, the width of the first member 110 between the first side 116 and the second side 118 at the top surface 122 may be, for example, approximately constant from the first end 112 to the second end 114. First side 116 and second side 118 may be, for example sloped out form the first member between the top surface and the bottom surface 148. Thus, the width may increase between the top surface 122 and the bottom surface 148. At the bottom surface the width of the first member 110 from the first end to the notches 144, 146 is narrower than the width of the first member 110 from the notches 144, 146 to the second end 114. With additional reference to FIG. 10, the various insets (e.g. inset E, F, G, and H) are similarly described here. The first and second engagement features 132, 134 are inset from the sides (e.g. the first side 116 and the second side 118). The first engagement feature 132 may be, for example, inset from the first side 116 by approximately 1 mm to 5 mm, between the medial notch 144 and the first end 112 and by approximately 1 mm to 7 mm, between the medial notch 144 and the second end 114. The first engagement feature 132 may be, more specifically, inset from the first side 116 by approximately 4.3 mm from the medial notch 144 to the first end 112 and by approximately 5.5 mm from the medial notch 144 to the second end 114. The second engagement feature 134 may be, for example, inset from the second side 118 by approximately 1 mm to 5 mm between the lateral notch 146 and the first end 112 and by approximately 1 mm to 7 mm between the lateral notch 146 and the second end 114. The second engagement feature 134 may be, for example, inset from the second side 118 by approximately 4.3 mm between the lateral notch 146 and the first end 112 and by approximately 5.5 mm between the lateral notch 146 and the second end 114. The first engagement feature 132 and the second engagement feature 134 may be positioned, for example, approximately equidistant from the first side 116 and the second side 118, respectively.

The portion of the bottom surface 148 between the medial side 116 and the recessed region 136 is the bottom surface medial side 140. The portion of the bottom surface 148 between the lateral side 118 and the recessed region 136 is the bottom surface lateral side 142.

The bottom surface 148 of the first member 110 also includes at least one engagement slot, groove, or locking groove 138. The at least one locking groove 138 may be, for example, positioned within the recessed region 136, between the anterior end 112 and the posterior end 114, and between the medial side 116 and the lateral side 118. The at least one locking groove 138 may be, for example, inset or recessed into the first member 110 within the channel or recessed region 136. The at least one locking groove 138 may be, for example, larger in the medial/lateral direction than in the anterior/posterior direction. The at least one locking groove 138 may have, for example, a polygonal shape, such as, a rectangular shape. The at least one locking groove 138 may be, for example, nine grooves. However, other embodiments may have, for example, more or less than nine locking grooves, for use with patients requiring different sizes of tibial and talar trials and implants and depending on the possible offset that may be needed based on the patient's anatomical dimensions.

With continued reference to FIGS. 26 and 32, the at least one locking groove 138 aligns or intersects with at least one transverse bore 124. The alignment of the locking grooves 138 with the transverse bores 124 provides a visual marker of the position of the interior locking grooves 138 on an exterior of the first member 110. The surgeon may use the exterior bores 124 to align a locking foot 154 with the interior locking grooves 138 during the surgical procedure to secure the first member 110 to the second member 200.

Referring now to FIGS. 17-37, the second member, base member, or articulating member 200 has a first end or anterior end 212 opposite a second end or posterior end 214. The second member 200 also has a first side or medial side 216 opposite a second side or lateral side 218. In addition, the second member 200 has the top surface 210 opposite an articulated surface 208. The first and second sides 216, 218 may have, for example, a first notch 228 in the first side 216, extending towards the second side 218, and a second notch 226 in the second side 218, extending towards the first side 216. The notches 226, 228 may extend from the first end 212 towards the second end 214, as shown in FIGS. 15 and 16. The first end 212 and second end 214 each have a surface that may, for example, be angled to approximately form an isosceles trapezoid or to have a convex curvature.

Further referring to FIGS. 17-37, the lock screw 150 is shown inserted in and coupled to the second member 200. The lock screw 150 may include a head 158 and as shown in FIGS. 17-37, the head 158 may protrude from the front end 212 of the second member 200 when the lock screw 150 is coupled to the second member 200. The lock screw 150 will be described in greater detail below and will not be described again here for the sake of brevity.

As shown in FIGS. 23, 24, 27, and 28, the sides (e.g. the first side 216 and the second side 218) may be angled, for example, outward from the vertical and the sides (e.g. the first side 216 and the second side 218) may be angled, for example, approximately 30° to 60° outward from the vertical and more preferably, approximately 45°, as the first side 216 and the second side 218 extend away from the top surface 210 to the articulated surface 208.

Referring to FIGS. 27, 28, 31, and 32, the medial side 216 and the lateral side 218 have notches 228, 226 extending from the anterior side 212 towards the posterior side 214. The notches 228, 226 further extend from the top surface 210 to the articulated surface 208 and may be, for example, vertical between the top surface 210 and the bottom surface 208. The first notch 228 may, for example, have the same angle as the first side 216 between the top surface 210 and the articulated surface 208. The second notch 226 may, for example, have the same angle as the second side 218 between the top surface 210 and the articulated surface 208. However, the first notch 228 and the second notch 226 may have angles that differ from the first side 216 and second side 218, respectively, with angles ranging from, for example, vertical to 60° from the top surface 210 to the articulated surface 208. The sides further have a transverse bore 224, extending from the medial side 216 to the lateral side 218. The transverse bore 224 may have, for example, a diameter ranging from approximately 0.25 mm to 2.0 mm, and more specifically, a diameter of approximately 1 mm. The transverse bore 224 may, for example, intersect with the second member bore 280 and/or the screw bore 152.

As shown in FIGS. 25 and 27-31, the top surface 210 of the second member 200 includes a raised section or an engagement member 240, raised out from the top surface 210 and extending from the anterior end 212 to the posterior end 214. With additional reference to FIG. 9, the various insets (e.g. inset A, B, C, and D) are similarly described here. For the sake of brevity, the inset measurements and dimensions are approximately the same. The engagement member 240 has a first engagement feature or first male dovetail 242 inset from the medial side 216, and a second engagement feature or second male dovetail 244 inset from the lateral side 218. The engagement member is between a medial top surface 246 and a lateral top surface 248. The first engagement feature 242 and the second engagement feature 244 extend from the first end 212 towards the second end 214. The engagement member 240, the first engagement feature 242, and the second engagement feature 244 may have, for example, a tapered region 250 extending from the first side 212 towards an engagement member top surface 220, as shown in FIGS. 21, 22, 29, and 30. The engagement member 240 is configured (e.g. shaped and dimensioned) for engagement with the engagement slot 128 of the first member 110.

Figure 25:
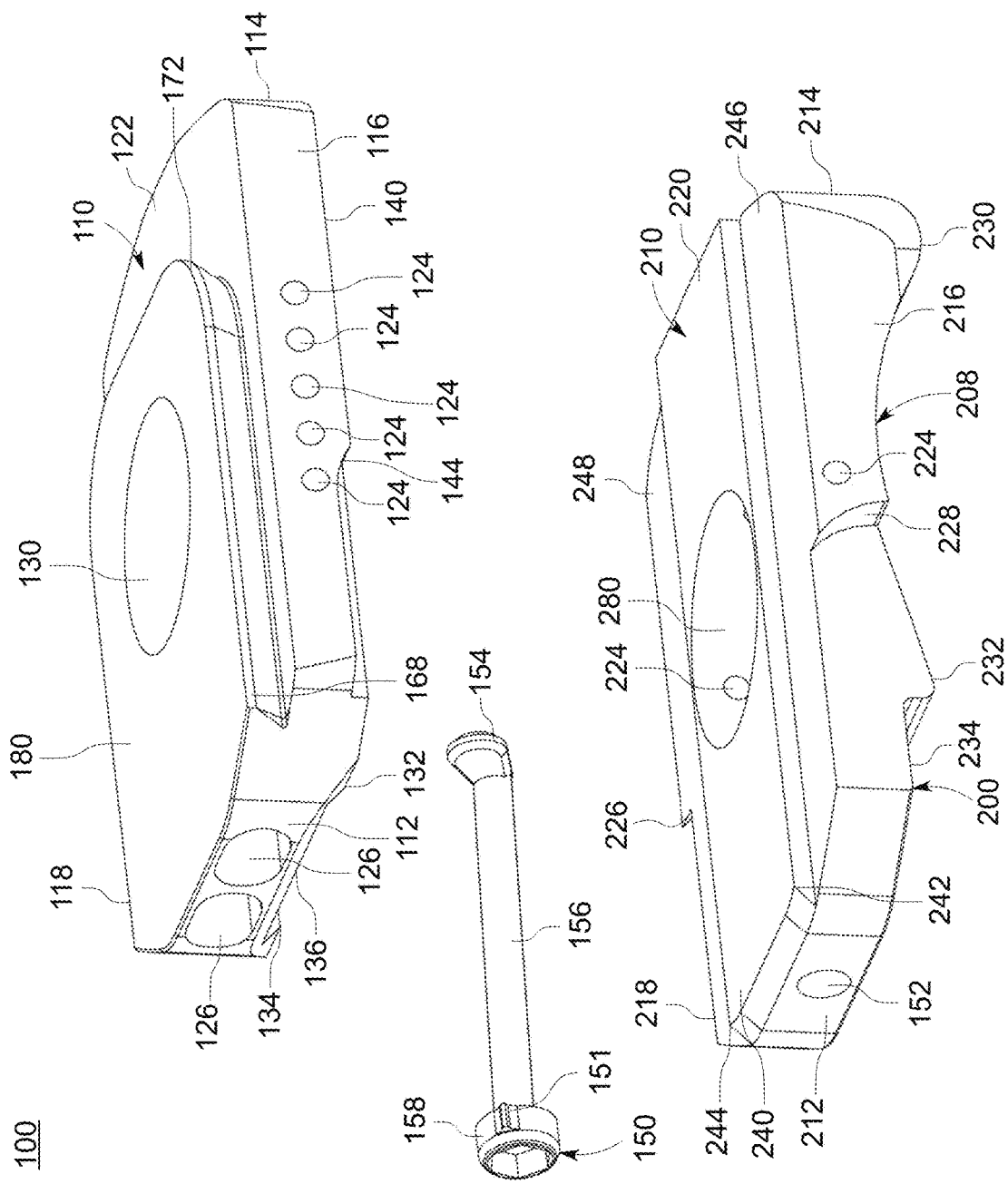
FIG. 25 is a first exploded, perspective view of the trial insert of FIG. 17, in accordance with an aspect of the present disclosure.
Figure 37:
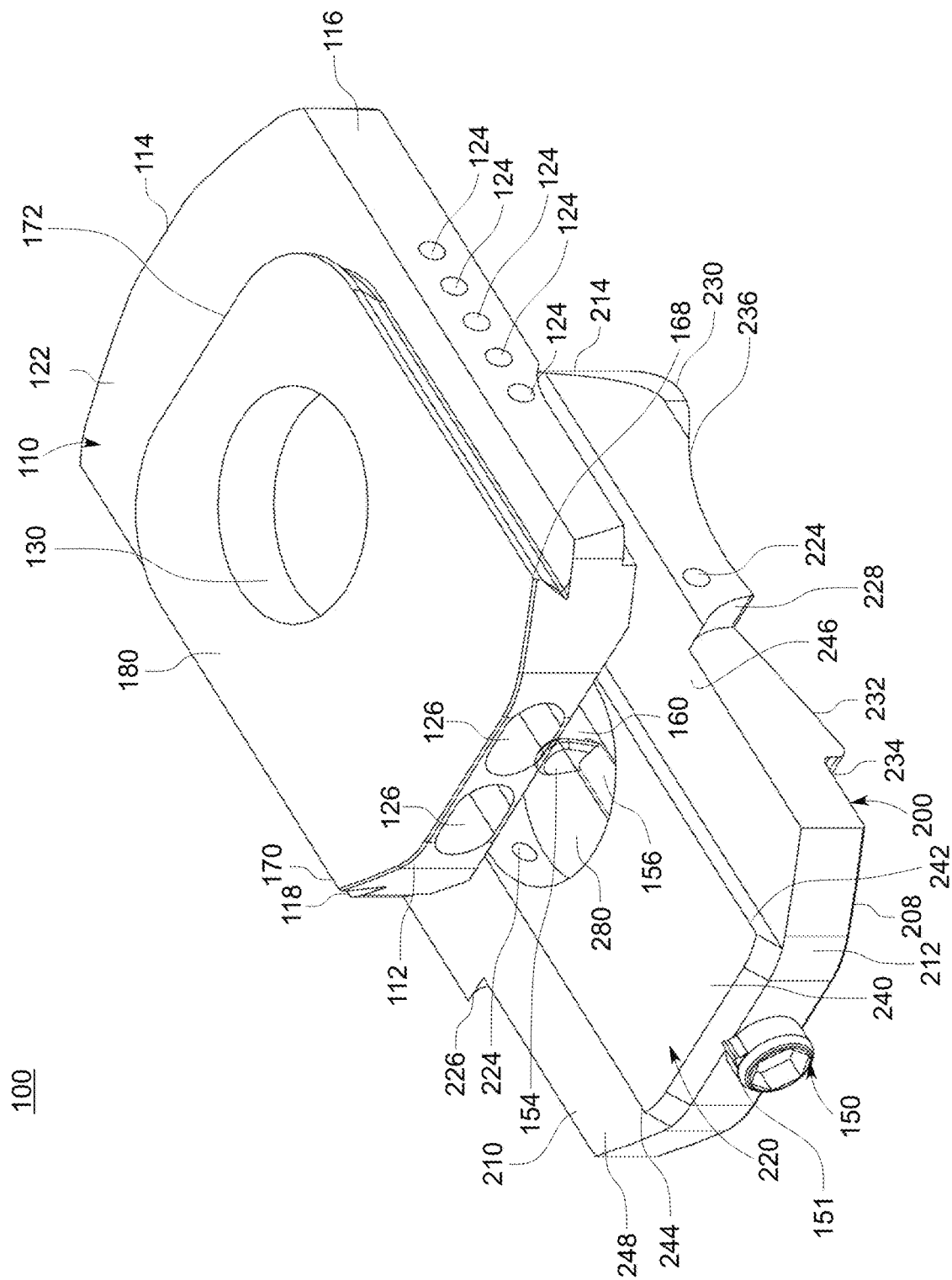
FIG. 37 is a first perspective view of the trial insert of FIG. 17 in a third position, in accordance with an aspect of the present disclosure.
Figure 38:
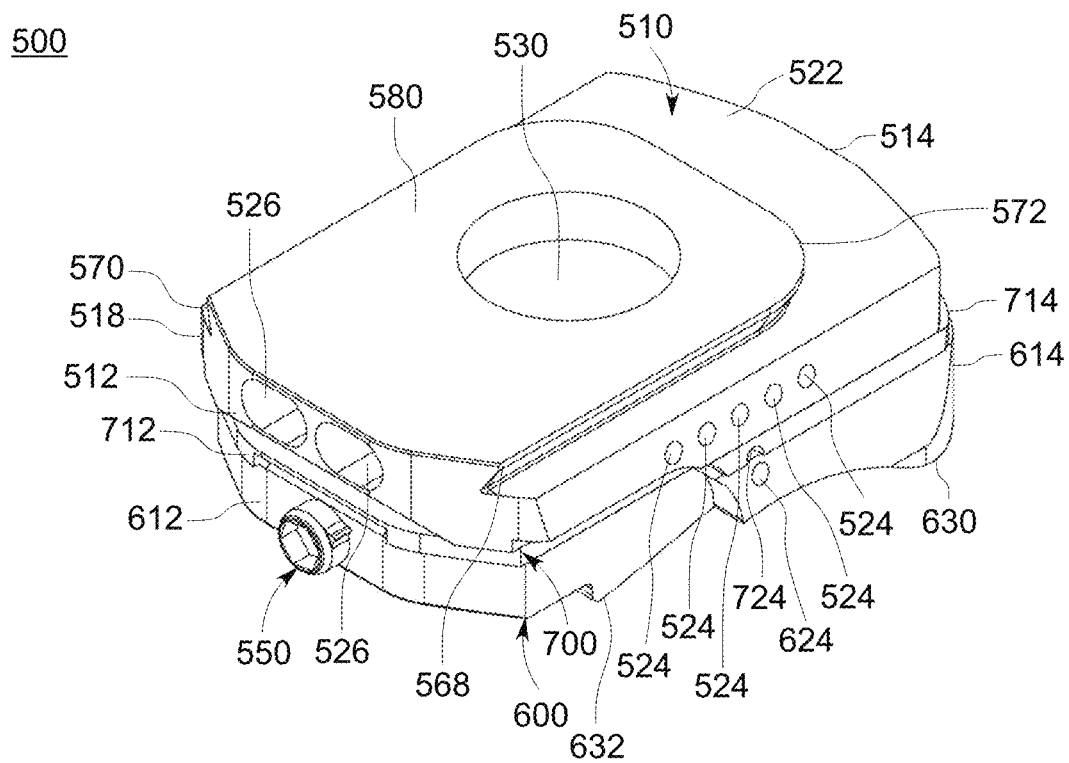
FIG. 38 is a first perspective view of yet another trial insert in a first position, in accordance with an aspect of the present disclosure.
Figure 39:
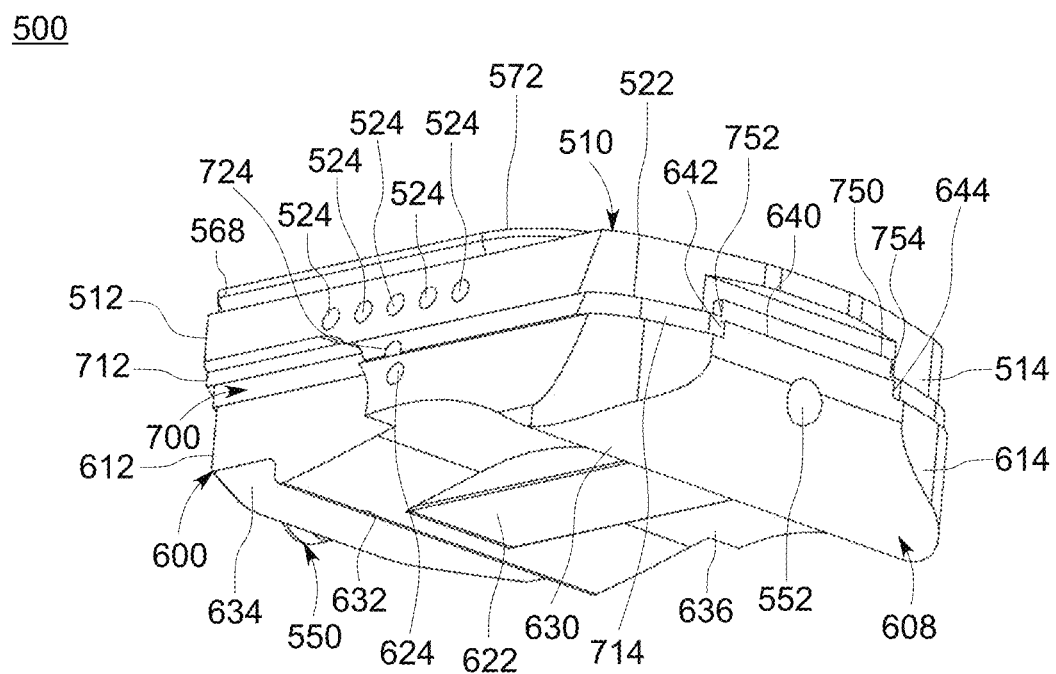
FIG. 39 is a second perspective view of the trial insert of FIG. 38, in accordance with an aspect of the present disclosure.
Figure 42:
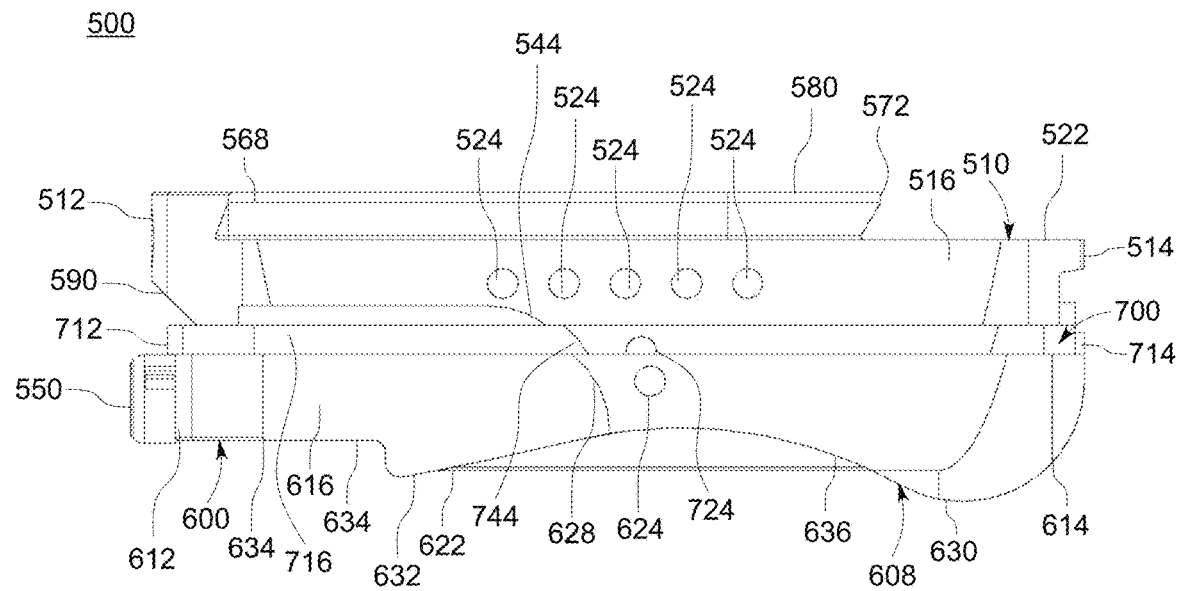
FIG. 42 is a first side view of the trial insert of FIG. 38, in accordance with an aspect of the present disclosure.
Figure 43:
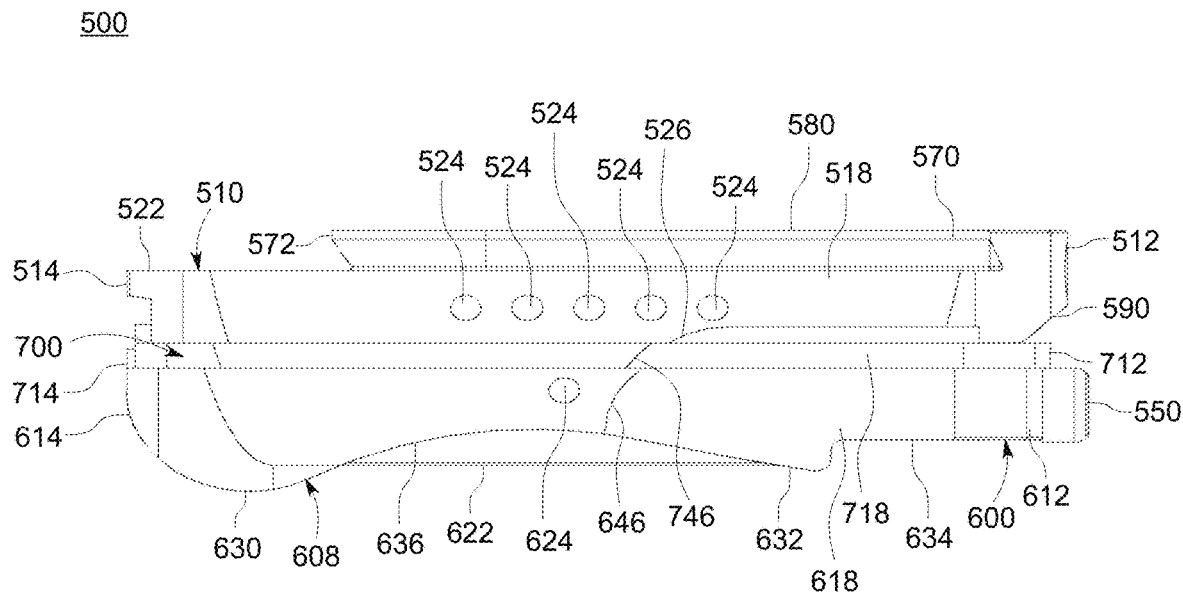
FIG. 43 is a second side view of the trial insert of FIG. 38, in accordance with an aspect of the present disclosure.
Figure 44:
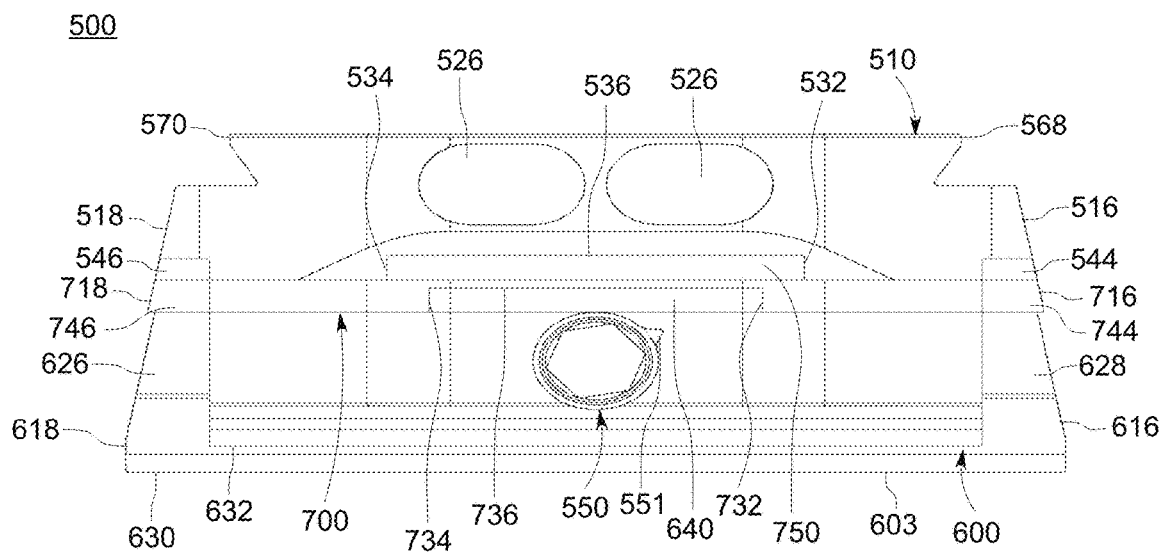
FIG. 44 is a first end view of the trial insert of FIG. 38, in accordance with an aspect of the present disclosure.
Figure 45:
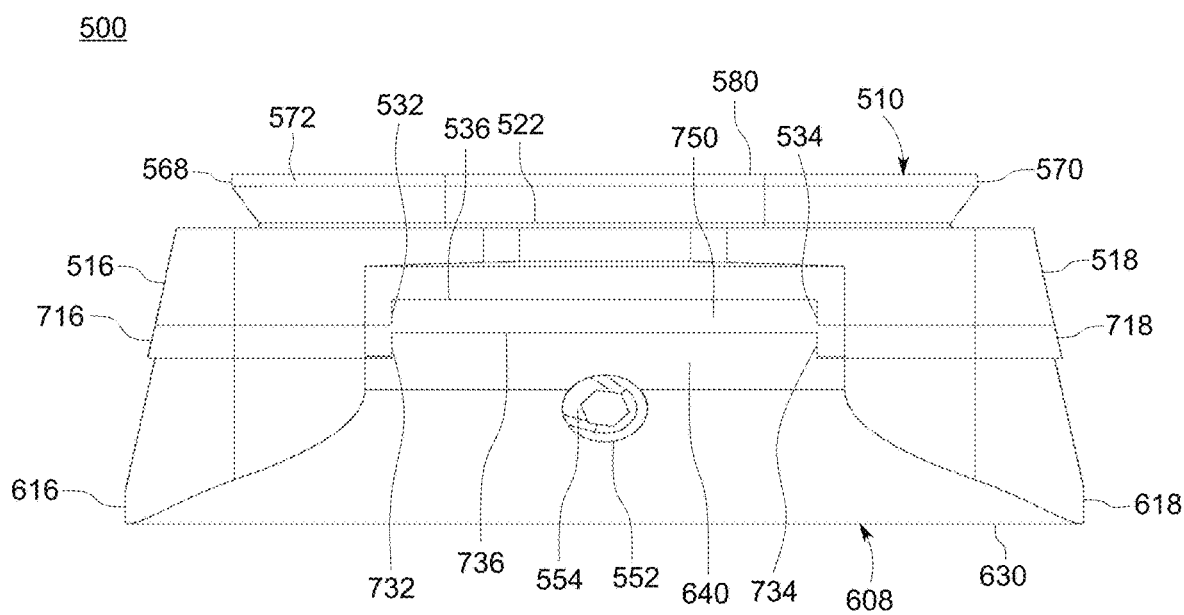
FIG. 45 is a second end view of the trial insert of FIG. 38, in accordance with an aspect of the present disclosure.

Referring to FIGS. 25, 31, and 37, a second member bore or second member cylinder 280 is shown extending from the engagement member top surface 220 toward the bottom surface 208. The second member bore 280 may, for example, have a diameter that ranges from approximately 5 mm to 15 mm and more specifically, may have a diameter of approximately 9.5 mm. The second member bore 280 may be positioned between the first engagement feature 242 and the second engagement feature 244 of the engagement member 240. The second member bore 280 may, for example, intersect the transverse bore 224.

Referring to FIGS. 25-30, and 37, the lock screw 150 is shown with a lock screw body or lock screw shaft 156, with the head 158 connected to one end and the locking foot 154 connected to an opposite end of the lock screw shaft 156. The lock screw body 156 is elongated and may be, for example, cylindrical. The lock screw body 156 may have, for example, threading extending along at least a portion of the length of the body 156 to engage an interior of the screw bore 152. Alternatively, the lock screw body 156 may be, for example, unthreaded or fully threaded. The lock screw body 156 may alternately have, for example, protrusions, spikes, barbs, or similar anchoring features extending outwards. The head 158 is shown with a circular or cylindrical shape and a hex or hexagonal drive type. However, other embodiments may include other head shapes or drive types. The head 158 may also have, for example, a protrusion 151 extending from the head 158 perpendicular to the shaft 156, and aligned with the foot 154, such that the protrusion 151 may be used to indicate an approximate rotational position of the foot 154. In other embodiments, protrusion 151 may be, for example, a notch, a marking, or an indicator, aligned with the position of the foot 154. The foot 154 may have, for example, an ovular or elliptical plate, with a length and width larger than thickness, and one end of the foot being flared. In other embodiments, the foot 154 may be, for example, any shape such that the length of the foot 154 is larger than the width. The foot 154 is shown extending from the end in an approximately perpendicular direction to the lock screw shaft 156, with the flared end extending away from the lock screw shaft 156 and the narrower end connected to the lock screw shaft 156. The lock screw 150 may be, for example, a monolithic component.

With reference to FIGS. 25, 27, 28, and 31, a lock screw bore 152 extends from the first end 212 towards the second end 214 of the second member 200. The lock screw bore 152 is shown extending from the first end 212 to the second end 214. However, it is also contemplated that in other embodiments, the lock screw bore 152 may extend towards but not entirely to the second end 214. The lock screw bore 152 may be, for example, cylindrical although alternative shapes are also contemplated. The second member bore 280 extends towards the bottom surface 248 such that the second member bore 280 intersects with the lock screw bore 152. The intersection of the second member bore 280 and the lock screw bore 152 may result in, for example, the lock screw bore 152 being a channel 160.

With reference to FIG. 37, the lock screw 150 is shown with the head 158 at the first end 212 and the lock screw body 156 extending into the lock screw bore 152, into the intersection between the lock screw bore 152 and the second member bore 280, with the foot 154 protruding from the second member bore 280. The lock screw 150 may be, for example, rotatable about a screw shaft longitudinal axis and within the lock screw bore 152. The foot 154, being within the channel 160, may be, for example, able to rotate between a first or transverse position and a second or dorsal position about the screw shaft longitudinal axis, and protruding through the top of the second member bore 280 above the engagement member 220.

As shown in FIGS. 26-30, and 32, the articulated surface 208 of the second member 200 includes a first segment 234, a second segment 232, a third segment 236, a fourth segment 230, and a trial engagement member 222. The first segment 234 extends from the first end 212 towards the second end 214, and may have, for example, a planar surface. The second segment 232 may extend, for example, from an end of the first segment 234, generally perpendicular to the articulated surface 208 forming a first portion of the second segment 232. The first portion of the second segment 232 may, for example, extend away from the articulated surface 208, for an exemplary embodiment of approximately 1 mm, although alternate distances are contemplated as would be known by one having ordinary skill in the art. From the free end of the first portion, the second segment 232 may, for example, curve or angle towards the top surface 210 and the second end 214 forming a second portion. The second portion of the second segment 232 may form, for example, a hypotenuse that connects to the third segment 236. The hypotenuse portion may be, for example, approximately 2.6 mm or greater and more specifically, have a linear distance of approximately 4.75 mm. The third segment 236 extends from an end of the second segment 232 towards the second end 214 of the second member 200 and connects with the fourth segment 230. The third segment 236 may, for example, be approximately parallel to the top surface 210 or may have a concave curvature between the second segment 232 and fourth segments 230. The third segment 236 may be, for example, curved in the direction of a longitudinal axis extending from the first end 212 to the second end 214. The fourth segment 230 may have, for example, a convex curvature extending from the third segment 436 and to the second end 214. The fourth segment 230 may be, for example, curved in the direction of the longitudinal axis.

As further shown in FIGS. 26-30, and 32, the trial engagement member 222 extends from the articulated surface 208 outwards, forming a raised structure extending from the second segment 232 to the third segment 236. The trial engagement member 222 further has a length which may be, for example, approximately perpendicular to the first end 212 and the second end 214. The trial engagement member 22 has a width which may be, for example, approximately perpendicular to the first side 216 and the second side 218. The trial engagement member 222 may have, for example, a length larger than the width. The trial engagement member 222 may, for example, have an exemplary length of approximately 14 mm, although alternate distances are contemplated as would be known by one having ordinary skill in the art. The trial engagement member 222 may, for example, have an exemplary width of approximately 6 mm, although alternate distances are contemplated as would be known by one having ordinary skill in the art. The trial engagement member 222 further has a bottom surface which may, for example, be a planar surface which extends parallel with the engagement member top surface 220.

With reference to FIGS. 17-37, the trial insert 100 is configured (e.g. shaped and dimensioned) for engagement with a tibial trial component or a tibial implant (not shown) at the trial engagement member 180, engagement between the first member 110 and the second member 200, and engagement between the second member 200 and a talar trial component or a talar implant (not shown). The first, second, and third engagement features 168, 170, 172, of the trial engagement member 180, engage with a tibial trial component (not shown), providing a fixed support for the first member 110 of the trial insert 100.

With continued reference to FIGS. 17-37, the engagement member 240 and the engagement slot 128 are engaged at the first female dovetail 132 and first male dovetail 242 and at the second female dovetail 134 and the second male dovetail 244, providing a linkage for movement of the first member 110 and the second member 200 relative to each other, and provides for relative position translation along the interface between the engagement slot 128 and the engagement member 200, in the anterior/posterior direction. However, since the first member 110 may be, for example, connected to the tibial trial component (not shown), the first member 110 may remain fixed and the second member 200 is moveable along the engagement member 240 within the engagement slot 128, in the anterior/posterior direction. The second member may be, for example, further engaged with the talar trial component (not shown) along the articulated surface 208, such that plantar flexion, neutral, and dorsiflexion motions may be simulated, and the positions of the trial insert 100 refined by further positioning the first member 110 relative to the second member 200. After the second member 200 is placed in a desired anterior/posterior position, the at least one locking groove 138 of the first member 110 may be, for example, above the second member bore 280 and the lock screw 150 may be rotated about the lock screw longitudinal axis, such that the flared end of the foot 154 engages with one of the at least one locking groove 138.

Referring now to FIGS. 38-58, another trial insert 500 is shown. The insert 500 includes a first member or movable member 510, a second member or base member 600, a shim or spacer 700, and a locking screw 550. The first member 510 includes atop surface 522 opposite a bottom surface 548. The second member 600 includes a top surface 610 opposite a bottom surface or articulated surface 608. The shim 700 includes a top surface 710 opposite a bottom surface 708. The top surface 610 of the second member 600 removably connects to the bottom surface 708 of the shim 700 and the bottom surface 548 of first member 510 engages the top surface 710 of the shim 700. The first member 510, the shim 700, and the second member 600 may come in multiple sizes for use with patients having different size tibia and talar bones and requiring different sizes of trials and/or implants.

As shown in FIGS. 46-53, the first member 510 includes a first end or anterior end 512 opposite a second end or posterior end 514. The distance between the first end 512 and the second end 514 may be, for example, approximately from 28 mm to 42 mm, and more specifically, approximately 30 mm. The first member 510 also includes a first side or medial side 516 opposite a second side or lateral side 518. The distance between the first side 516 and the second side 518 may, for example, range from 20 mm to 34 mm, and more specifically be approximately 20 mm. The top surface 522 includes a bone trial connector, a trial engagement member, or a prosthetic engagement member 580, extending from the anterior end 512 towards the posterior end 514, as shown in FIGS. 40, 42, 43, and 50-52. The trial engagement member 580 may be, for example, inset from the posterior end 514 by, for example, approximately 4 mm to 8 mm, and more specifically approximately 7 mm. The trial engagement member 580 may be, for example, inset approximately 0 mm to 5 mm, more specifically, approximately 0 mm to 3 mm, from the first side 516 and the second side 518 respectively, and, yet more specifically inset approximately 1.8 mm from the first side 516 and the second side 518, as shown in FIGS. 44, 45, 48 and 49. The trial engagement member insets from the first side 516 and the second side 518 and may be, for example, approximately equidistant. In an alternative embodiment, the trial engagement member 580 may, for example, extend between the first side 516 and the second side 518 and from the anterior end 512 to the posterior end 514.

The trial engagement member 580 may have, for example, engagement features along sections of the perimeter such as a first engagement feature or first male dovetail 568, a second engagement feature or second male dovetail 570, and a third engagement feature or third male dovetail 572, as shown in FIGS. 38, 40, 46, and 52. The first engagement feature 568 and the second engagement feature 570 may, for example, extend from the anterior end 512 towards the posterior end 514. The two engagement features 568, 570 may extend approximately parallel with the male dovetail features facing in opposing directions towards the medial and lateral sides, 516 and 518, respectively, as shown in FIGS. 40 and 52. With continued reference to FIGS. 40 and 52, the third engagement feature 572 may be, for example, approximately perpendicular and extend between or connect to the first engagement feature 568 and the second engagement feature 570. The third male dovetail 572 may, for example, face the posterior end 514. The connection between the first engagement feature 568 and the third engagement feature 572 and the connection between the second engagement feature 570 and the third engagement feature 572 may, for example, be tapered, angled, squared, curved, or arced.

With reference to FIGS. 42-45 and 48-51, the trial engagement member 580 may, for example, extend away from the top surface 522 of the first member 510, to an exemplary embodiment height of approximately 1.6 mm, although alternate heights are contemplated as would be used by one having ordinary skill in the art. The trial engagement member 580 may have, for example, a vertical bore 530 extending from the top surface of the trial engagement member 580 towards the bottom surface 548 of the first member 510. The vertical bore 530 may, for example, be approximately circular, round, oval or the like, with an approximate diameter ranging from 5 mm to 15 mm, and more specifically a diameter of approximately 10 mm.

With reference to FIGS. 44, 45, 48, and 49, the first side 516 and the second side 518 of the first member 510 may be, for example, sloped, tapered, or angled as the sides (e.g. the first side 516 and the second side 518) extend between the top surface 522 and the bottom surface 548 of the first member 510. The angle of the first side 516 and the second sides 518 extending from the top surface 522 to the bottom surface 548 may be, for example, approximately 30° to 60° extending outwards from vertical and more specifically approximately 45° outwards from vertical.

With reference to FIGS. 40, 41, 52, and 53, the first end 512 and second end 514 each have a surface that may be, for example, be angled to approximately form an isosceles trapezoid or to have a convex curvature.

With continued reference to FIGS. 44, 45, 48, and 49, the first end 512 is shown with at least one front opening or front bore 526, having, for example, an ovular shape or elliptical shape. In other embodiments, the at least one bore 526 may be circular. The at least one front bore 526 may be, for example, two front bores 526 positioned adjacent to each other. The two front bores 526 may be shaped and configured for use with an insertion instrument (not shown), more specifically, a forked insertion instrument (not shown). In other embodiments, there may be, for example, a single front bore or more than two front bores.

Referring now to FIGS. 42, 43, 46, 47, 50, and 51, at least one transverse bore 524 is shown extending from the medial side 516 to the lateral side 518. The at least one transverse bore 524 may be, for example, five transverse bores. However, there may be embodiments with more or less than five transverse bores, for use with patients with different size bones which require different size tibial trials and/or tibial implants. The transverse bores 524 may have, for example, a range from approximately 0.25 mm to 2.0 mm and more specifically, may be approximately 1 mm in diameter. The medial side 516 further has a medial notch or first notch 544 extending from the medial side 516, towards the lateral side 518. The lateral side 518 has a lateral notch or second notch 546, extending from the lateral side 518 towards the medial side 516. The first and second notches 544, 546, also extend from the first end 512 towards the second end 514.

Figure 47:
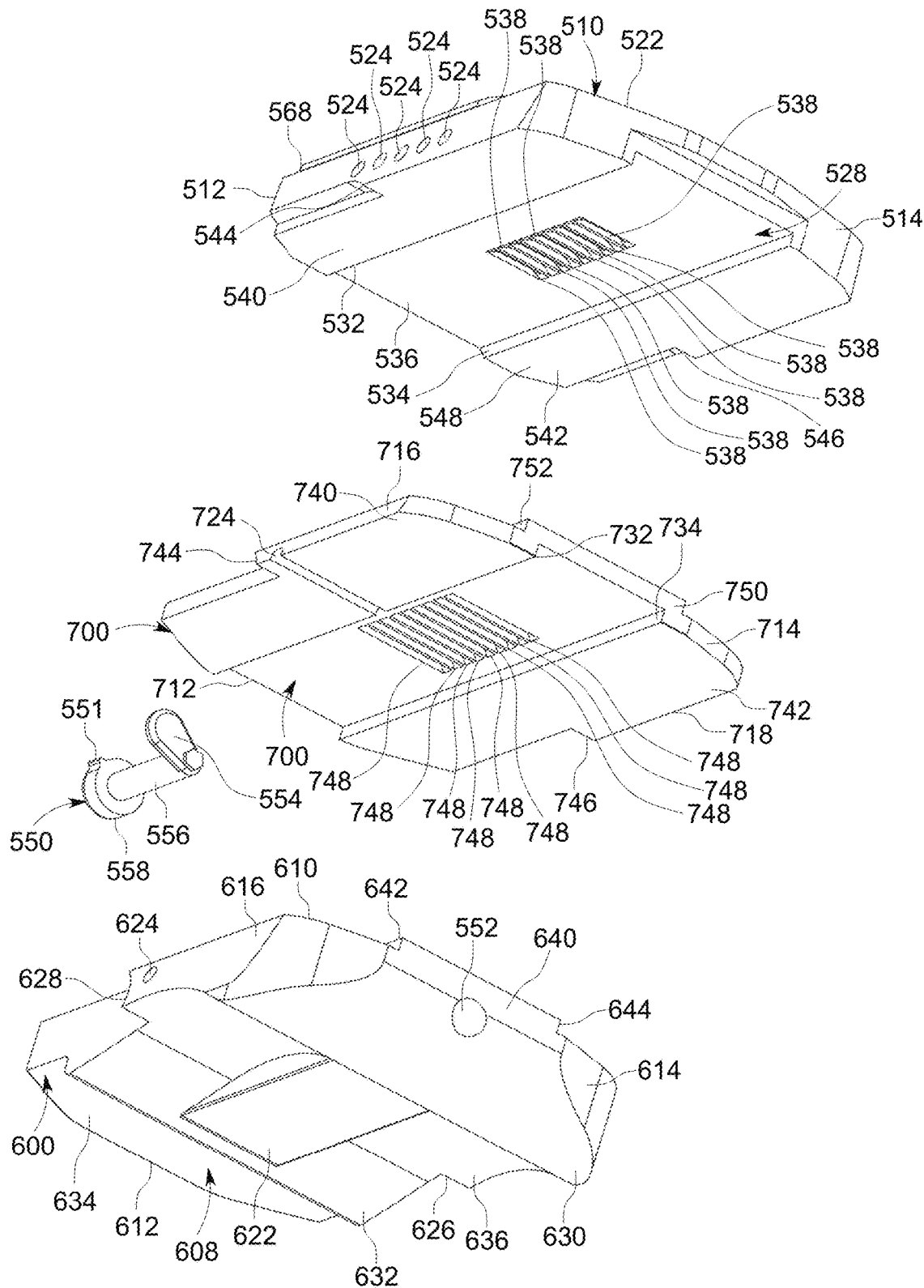
FIG. 47 is a second exploded, perspective view of the trial insert of FIG. 38, in accordance with an aspect of the present disclosure.
Figure 53:
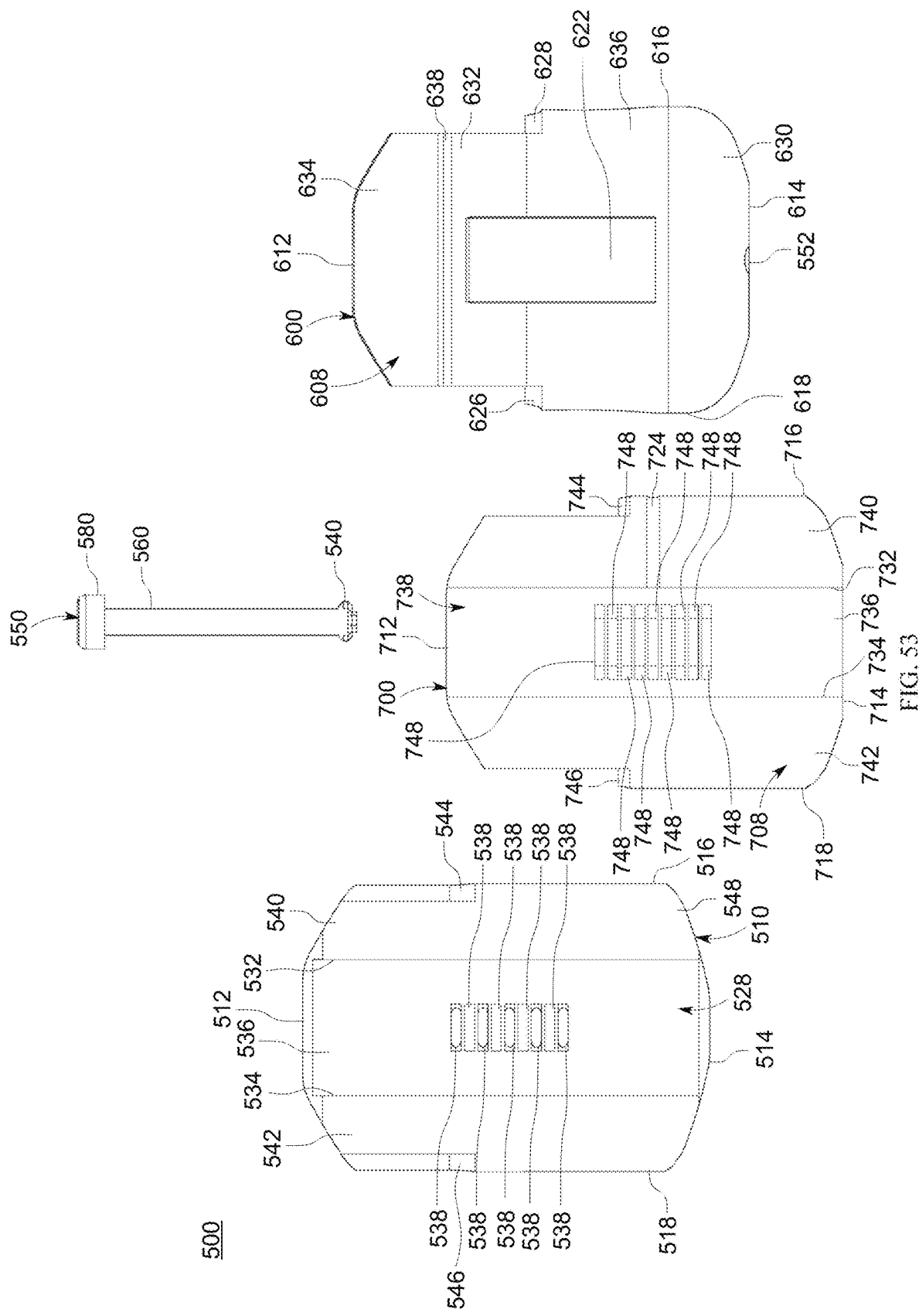
FIG. 53 is an exploded, bottom view of the trial insert of FIG. 38, in accordance with an aspect of the present disclosure.
Figure 54:
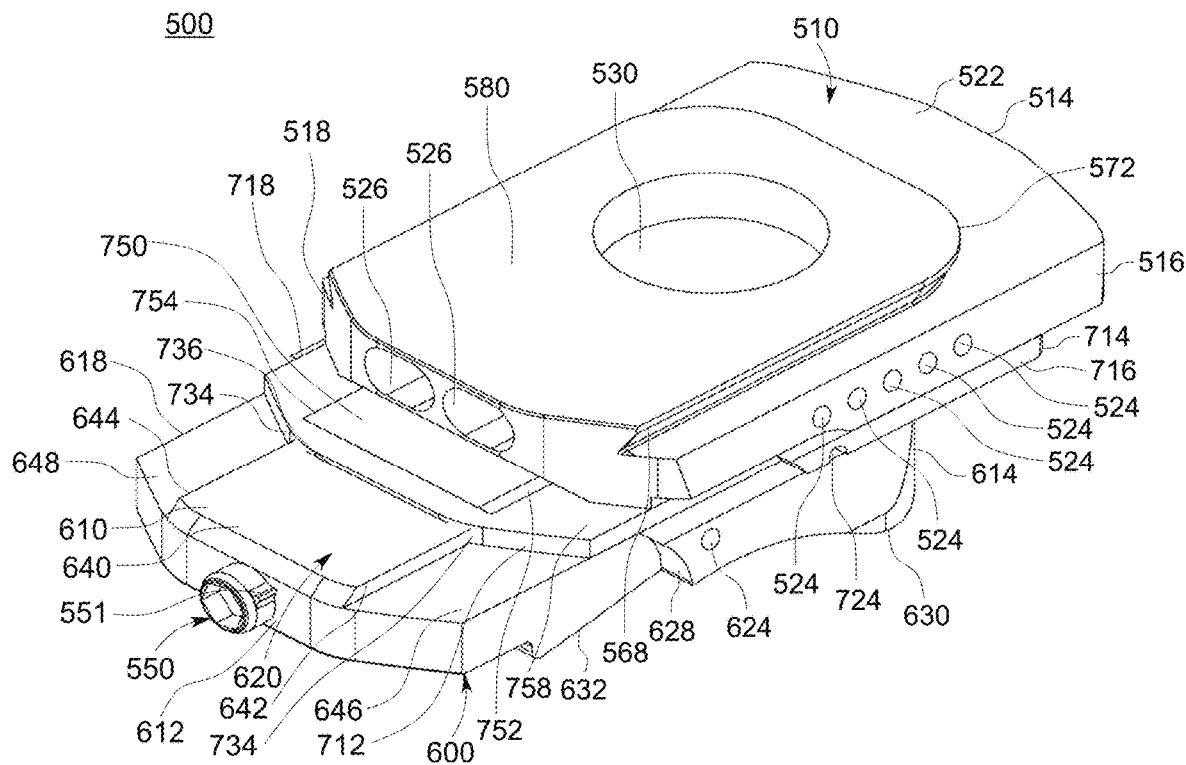
FIG. 54 is a first perspective view of trial insert of FIG. 38 in a second position, in accordance with an aspect of the present disclosure.
Figure 55:
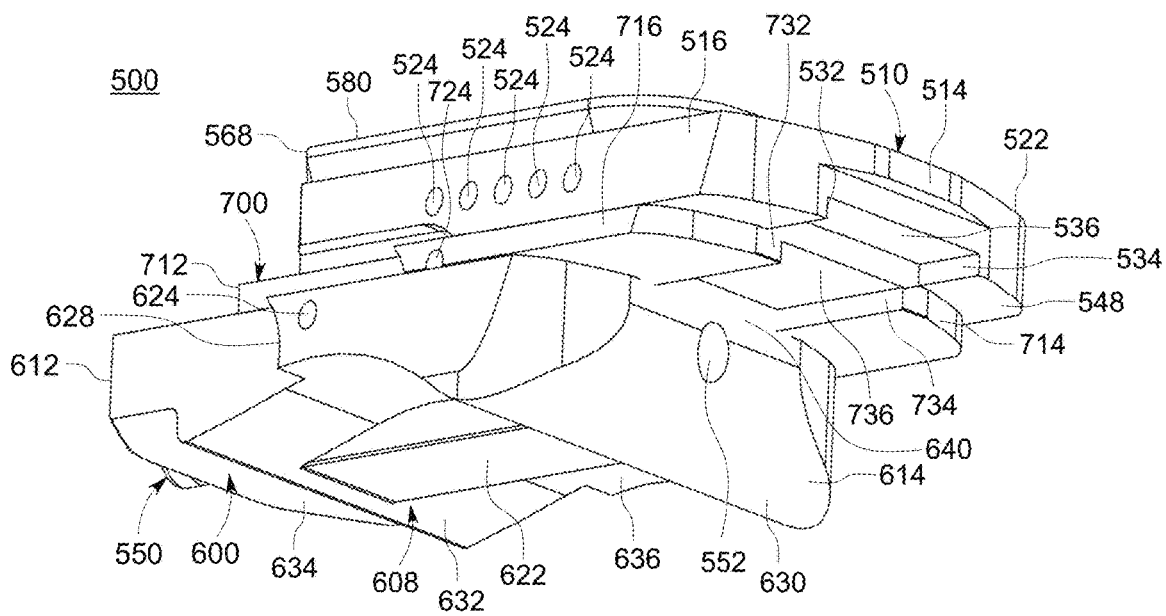
FIG. 55 is a second perspective view of the trial insert of FIG. 54, in accordance with an aspect of the present disclosure.
Figure 56:
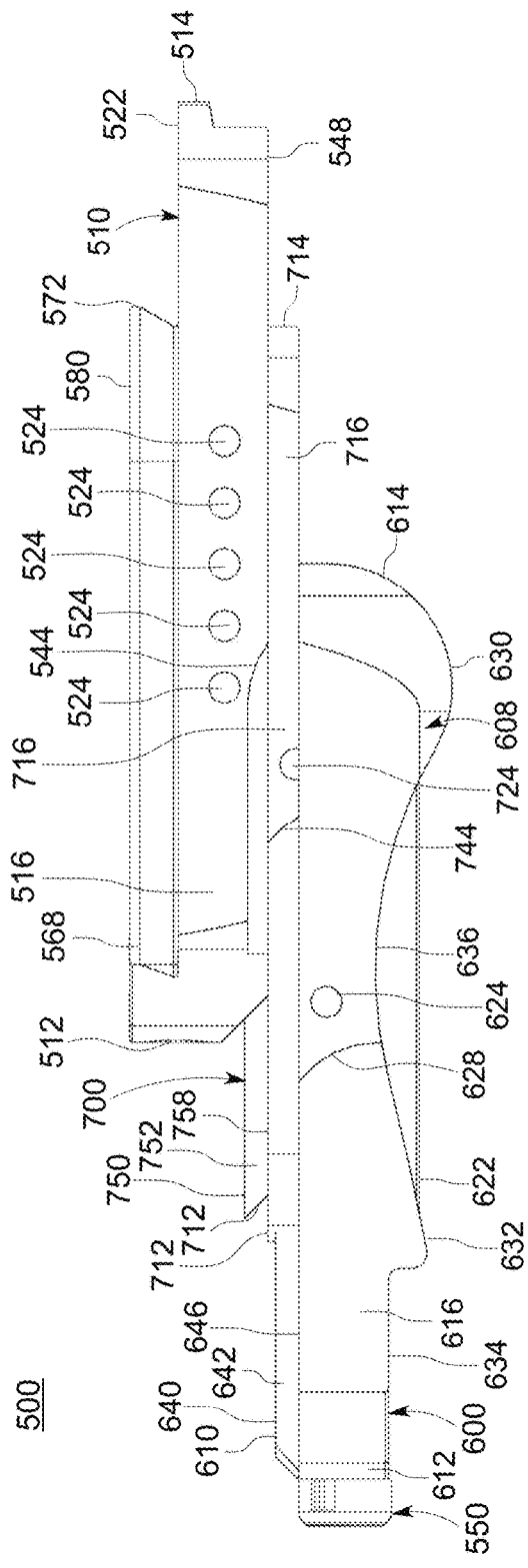
FIG. 56 is a first side view of the trial insert of FIG. 54, in accordance with an aspect of the present disclosure.
Figure 57:
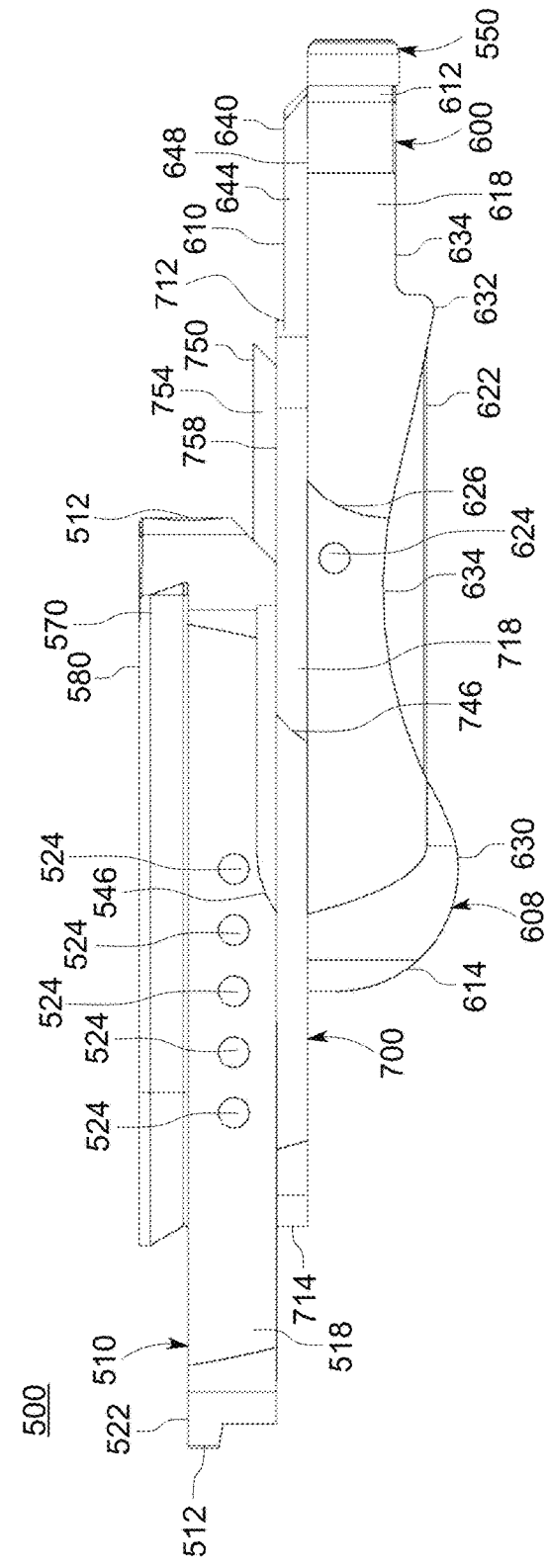
FIG. 57 is a second side view of the trial insert of FIG. 54, in accordance with an aspect of the present disclosure.

Referring now to FIGS. 47 and 53, the bottom surface 548 of the first member 510 is shown. The bottom surface 548 includes a recessed region or engagement region 536 extending into the first member 510 from the bottom surface 548 toward the top surface 522. The bottom surface 548 also includes an engagement slot or an engagement channel 528 extending from the first end 512 into the recessed region 536 to the second end 514 and bordered toward the first side 516 by a first engagement feature or first female dovetail portion 532 and bordered toward the second side 518 by a second engagement feature or second female dovetail portion 534. The engagement channel 528, first engagement feature 532, and second engagement feature 534 may have, for example, a tapered region 590 extending from the first side 512 towards the bottom surface 548, as shown in FIGS. 42, 43, 50, and 51. The recessed region may have, for example, a width between the first and second engagement features 332, 334 of approximately 5 mm to 15 mm and more specifically approximately 10 mm. The first member 510 may come in multiple sizes for use with patients requiring different sized trials and/or implants and the engagement channel 528 of each of the first members 510 may be, for example, sized and shaped the same to allow for replacement of the first member 510 as needed.

Referring to FIGS. 47-49, and 53, the width of the first member 510 between the first side 516 and the second side 518 at the top surface 522 may be, for example, approximately constant from the first end 512 to the second end 514. First side 516 and second side 518 may be, for example sloped out form the first member between the top surface and the bottom surface 548. Thus, the width may increase between the top surface 522 and the bottom surface 548. At the bottom surface the width of the first member 510 from the first end to the notches 544, 546 is narrower than the width of the first member 510 from the notches 544, 546 to the second end 514. With additional reference to FIG. 10, the various insets (e.g. inset E, F, G, and H) are similarly described here. The first and second engagement features 532, 534 are inset from the sides (e.g. the first side 516 and the second side 518). The first engagement feature 532 may be, for example, inset from the first side 516 by approximately 1 mm to 5 mm, between the medial notch 544 and the first end 512 and by approximately 1 mm to 7 mm, between the medial notch 544 and the second end 514. The first engagement feature 532 may be more specifically, inset from the first side 516 by approximately 4.3 mm from the medial notch 544 to the first end 512 and by approximately 5.5 mm from the medial notch 544 to the second end 514. The second engagement feature 534 may be, for example, inset from the second side 518 by approximately 1 mm to 5 mm between the lateral notch 546 and the first end 512 and by approximately 1 mm to 7 mm between the lateral notch 546 and the second end 514. The second engagement feature 534 may be, more specifically, inset from the second side 518 by approximately 4.3 mm between the lateral notch 546 and the first end 512 and by approximately 5.5 mm between the lateral notch 546 and the second end 514. The first engagement feature 532 and the second engagement feature 534 may be positioned, for example, approximately equidistant from the first side 516 and the second side 518, respectively.

The portion of the bottom surface 548 between the medial side 516 and the recessed region 536 is the bottom surface medial side 540. The portion of the bottom surface 548 between the lateral side 518 and the recessed region 536 is the bottom surface lateral side 542.

The bottom surface 548 of the first member 510 also includes at least one engagement slot groove or locking groove 538. The at least one locking groove 538 may be, for example, positioned within the recessed region 536, between the anterior end 512 and the posterior end 514, and between the medial side 516 and the lateral side 518. The at least one locking groove 518 may be, for example, larger in the medial/lateral direction than in the anterior/posterior direction. The at least one locking groove 538 may be, for example, nine grooves. However, other embodiments may have, for example, more or less than nine locking grooves 538, based on the size of the trial insert 500 and the corresponding size of the patient's tibia and talus.

With continued reference to FIGS. 47 and 53, the alignment of the locking grooves 538 with the transverse bores 524 provides a visual marker of the position of the interior locking grooves 538 on an exterior of the first member 510. The surgeon may use the exterior bores 524 to align a locking foot 554 with the interior locking grooves 538 during the surgical procedure to secure the first member 510 to the second member 600.

Referring again to FIGS. 38-58, the shim 700 is shown positioned between the first member 510 and the second member 600. The shim 700 engages the first member 510 on the top side 710 and the second member 600 on the bottom side 708. The shim 700 may, for example, adjust spacing in the dorsal/plantar directions and/or help the first member 510 engage with the second member 600. The shim 700 may come in varying thicknesses to provide spacing options between the first member 510 and the second member 600, as needed for variations in patient anatomy.

With reference to FIGS. 46-53, the shim 700 has a first end or anterior end 712 opposite a second end or posterior end 714, a first side or medial side 716 opposite a second side or lateral side 718, and with the top surface 710 opposite the bottom surface 708. The shim 700 has a thickness between the top surface 710 and the bottom surface 708. The first and second sides 716, 718 may have, for example, a first notch 744 in the first side 716, extending towards the second side 718, and a second notch 746 in the second side 718, extending towards the first side 716. The notches 744, 746 may extend from the first end 712 towards the second end 714, as shown in FIGS. 52 and 53.

With reference to FIGS. 48, 49, and 52, the shim 700 has an engagement member 750. The engagement member 750 extends out from the top surface 710 and from the first end 712 to the second end 714. The engagement member 750 may also be inset from the first side 716 along a medial top surface 756 and from the second side 718 along a lateral top surface 758. The engagement member 750 further has a top surface 720. The engagement member 750 has a first engagement feature or first male dovetail 752 positioned towards the medial side 716 and a second engagement feature or second male dovetail 754 positioned towards the lateral side 718. The first and second engagement features 752, 754 may also extend along at least a portion of the top surface 720 between the second end 714 and the first end 712. The first engagement feature 752 may extend parallel to the second engagement feature 754 along a first or anterior/posterior direction. In addition, near the first end 712, the engagement member 750 may, for example, slope or curve to meet the top surface 710 at or near the first end 712.

With reference to FIGS. 48, 49, and 53, the shim 700 has an engagement slot 738, extending from the bottom surface 708 towards the top surface 710. The engagement slot 738 may be, for example, inset or recessed into the bottom surface 708 of the shim 700 forming a recessed region 736. The recessed region 736 is opposite the top surface 720 of the engagement member 750. The engagement slot 738 extends along a first or anterior/posterior direction between the first end 712 and the second end 714. The recessed region 736 is also inset from the medial side 716 and the lateral side 718, between a medial bottom surface 740 and a lateral bottom surface 742. The engagement slot 738 further has a first engagement feature or first female dovetail 732 positioned toward the medial side 716 and a second engagement feature or second female dovetail 734 positioned toward the lateral side 718. The first and second engagement features 732, 734 may also extend from the first end 712 to the second end 714. The first engagement feature 732 may extend parallel to the second engagement feature 734 along the anterior/posterior direction.

With continued reference to FIGS. 48, 49, 52, and 53, the first side 716 slopes outward in a medial direction and the second side 718 slopes outward in a lateral direction, with both sides being angled, curved, or sloping from the top surface 710 to the bottom surface 708. The slope is configured, shaped and dimensioned, to approximately match the slope of the sides of the first member 510 and the second member 600.

Referring to FIGS. 50 and 51, the shim 700 has a transverse hole 724, extending from one side towards the other side, for example the first side 716 towards the second side 718. In other embodiments, the hole may extend from the second side 718 towards the first side 716 or from the first side 716 to the second side 718. The transverse hole 724 is shown as a semi-circular shape but may be of any shape. The transverse hole 724 may be, for example, used to set a zero or initial position of the shim 700, in relation to the first member 510 and/or the second member 600.

Referring now to FIGS. 46, 47, 52, and 53, the shim 700 has at least one engagement opening or locking opening 748, extending from top surface 720 of the engagement member 750 to the recessed region 726 of the engagement slot 738. The at least one locking opening 748 is positioned within the first engagement features 732, 752 and the second engagement features 734, 754. The at least one locking opening 748 is shown as being longer in the medial/lateral direction than in the anterior/posterior direction, and may be, for example, rectangular.

Referring now to FIGS. 38-58, the second member, base member, or articulating member 600 has a first end or anterior end 612 opposite a second end or posterior end 614. The second member 600 also has a first side or medial side 616 opposite a second side or lateral side 618. In addition, the second member 600 has the top surface 610 opposite the bottom surface or articulated surface 608. The first and second sides 616, 618 may have, for example, a first notch 628 in the first side 616, extending towards the second side 618, and a second notch 626 in the second side 618, extending towards the first side 616. The notches 628, 626 may extend from the first end 612 to the second end 614, as shown in FIGS. 52 and 53. The first end 612 and second end 614 each have a surface that may, for example, be angled to approximately form an isosceles trapezoid or to have a convex curvature.

Further referring for FIGS. 38-58, lock screw 550 is shown inserted in and coupled to the second member 600. The lock screw 550 may include a head 558 and as shown in FIGS. 38-58, the head 558 may protrude from the front end 612 of the second member 600 when the lock screw 550 is coupled to the second member 600. The lock screw 550 will be described in greater detail below and will not be described again here for the sake of brevity.

As shown in FIGS. 44, 45, 48, and 49, the surfaces of the first and second sides 616, 618 may be angled, for example, approximately 30° to 60° outward from the vertical and more preferably, approximately 45°, between the top surface 610 and the articulated surface 608.

Referring to FIGS. 48, 49, 52, and 53, the medial side 616 and the lateral side 618 have notches 628, 626 extending from the anterior side 612 towards the posterior side 614. The notches 628, 626 further extend from the top surface 610 to the articulated surface 608 and may be, for example, vertical between the top surface 610 and the bottom surface 608. The first notch 628 may, for example, have the same angle as the first side 616 between the top surface 610 and the articulated surface 608. The second notch 626 may, for example, have the same angle as the second side 618 between the top surface 610 and the articulated surface 608. However, the first notch 628 and the second notch 626 may have angles that differ from the first side 616 and second side 618, respectively, with angles ranging from vertical to 60° from the top surface 610 to the articulated surface 608. In addition, the sides have a transverse bore 624, extending from the medial side 616 to the lateral side 618. The transverse bore 624 may have, for example, a diameter ranging from approximately 0.25 mm to 2.0 mm and more specifically, a diameter of approximately 1 mm. The transverse bore 624 may, for example, intersect with the second member bore 680 and/or the screw bore 552.

As shown in FIGS. 46 and 48-52, the top surface 610 of the second member 600 includes a raised section or an engagement member 640, raised out from the top surface 610 and extending from the anterior end 612 to the posterior end 614. With additional reference to FIG. 9, the various insets (e.g. inset A, B, C, and D) are similarly described here. For the sake of brevity, the inset measurements and dimensions are approximately the same. The engagement member 640 has a first engagement feature or first male dovetail 642 inset from the medial side 616 and a second engagement feature or second male dovetail 644 inset from the lateral side 618. The engagement member 640 is positioned between a medial top surface 646 and a lateral top surface 648. The first engagement feature 642 and the second engagement feature 644 extend from the first end 612 towards the second end 614. The engagement member 640, first engagement feature 642, and second engagement feature 644 may have, for example, a tapered region 650 extending from the first side 612 towards an engagement member top surface 620, as shown in FIGS. 5, 6, 13, and 14. The engagement member 640 is sized, shaped, and configured for engagement with the engagement slot 738 of the shim 700.

Figure 46:
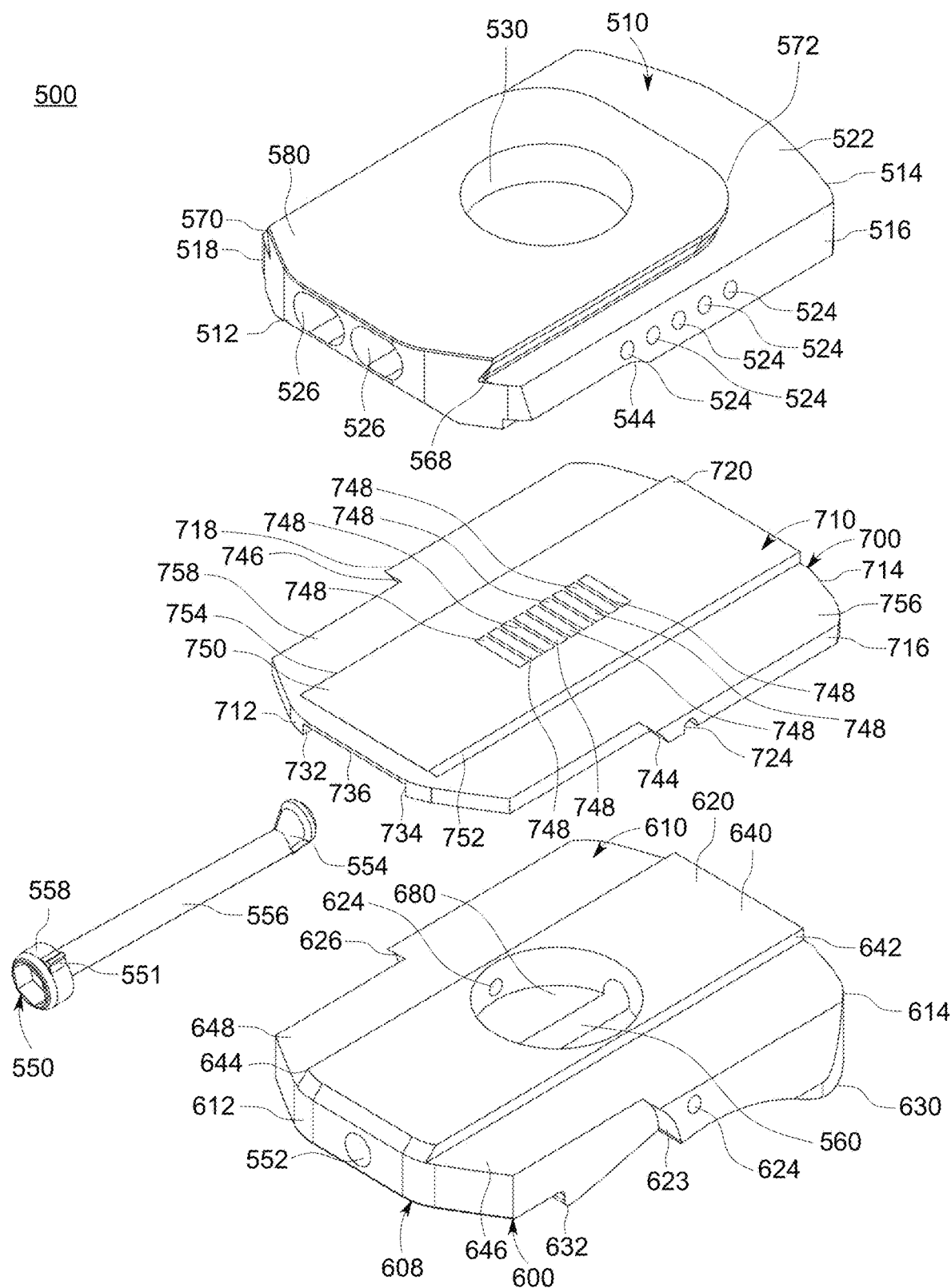
FIG. 46 is a first exploded, perspective view of the trial insert of FIG. 38, in accordance with an aspect of the present disclosure.
Figure 58:
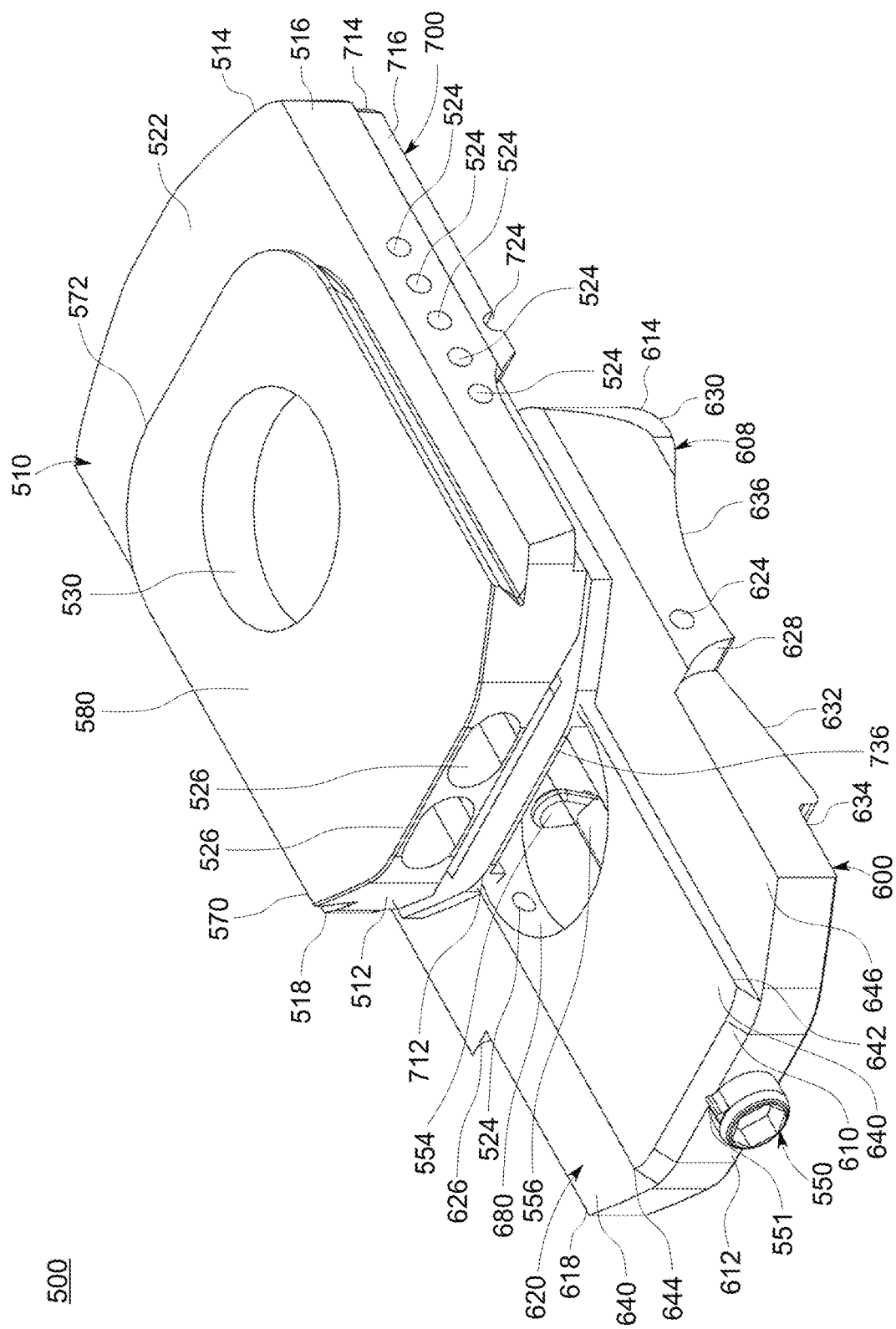
FIG. 58 is another perspective view of the trial insert of FIG. 38 in a third position, in accordance with an aspect of the present disclosure.
Figure 59:
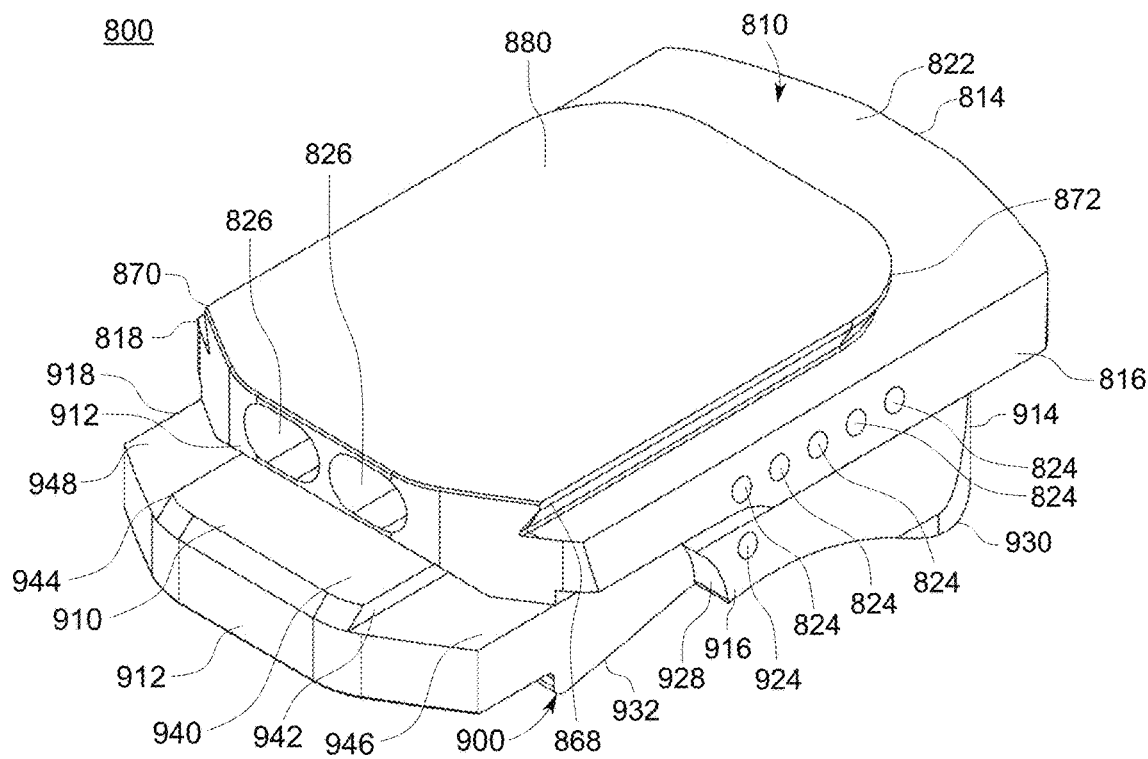
FIG. 59 is a first perspective view of another trial insert, in accordance with an aspect of the present disclosure.
Figure 60:
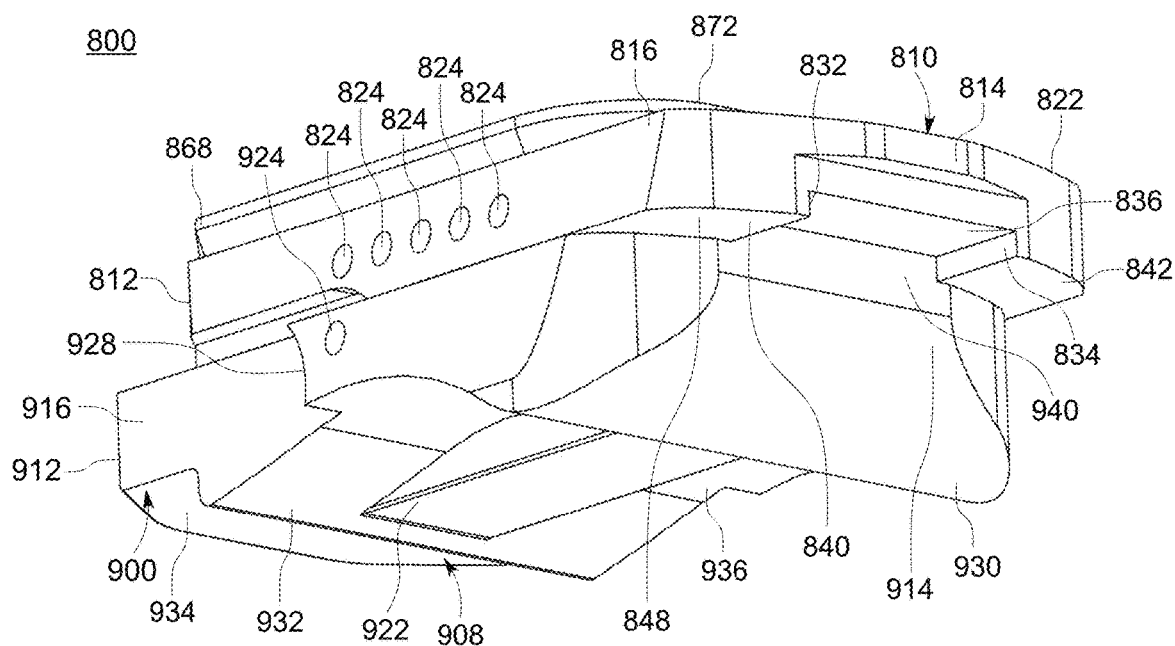
FIG. 60 is a second perspective view of the trial insert of FIG. 59, in accordance with an aspect of the present disclosure.
Figure 63:
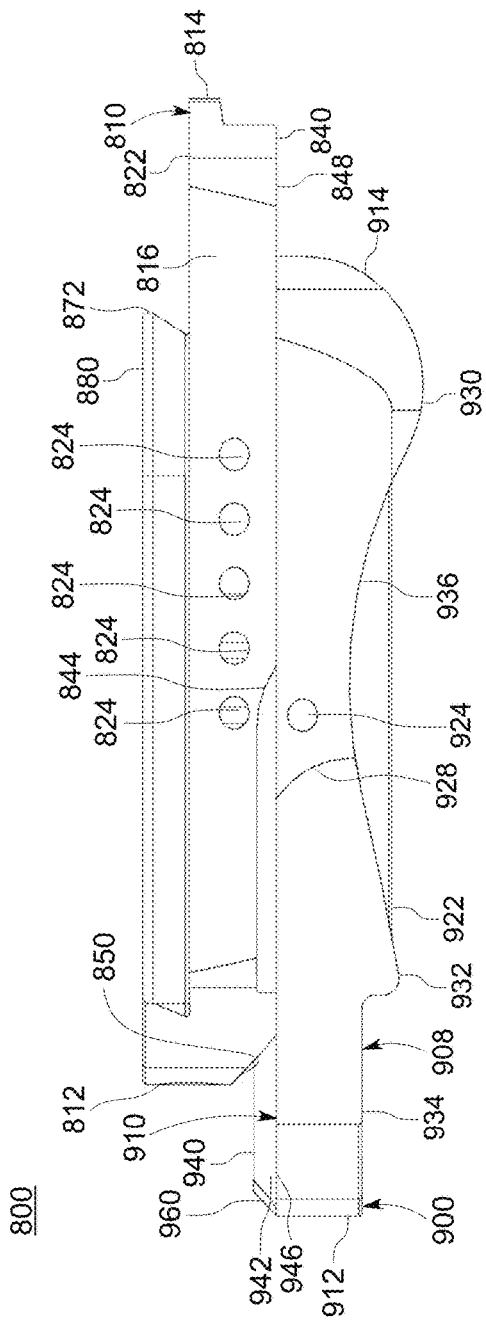
FIG. 63 is a first side view of the trial insert of FIG. 59, in accordance with an aspect of the present disclosure.
Figure 64:
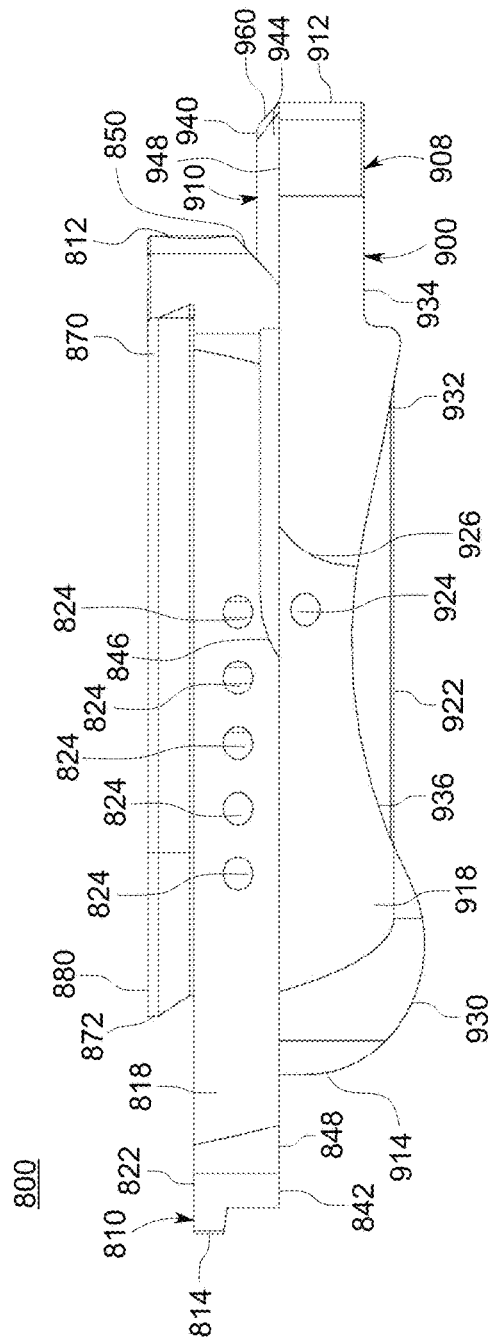
FIG. 64 is a second side view of the trial insert of FIG. 59, in accordance with an aspect of the present disclosure.
Figure 65:
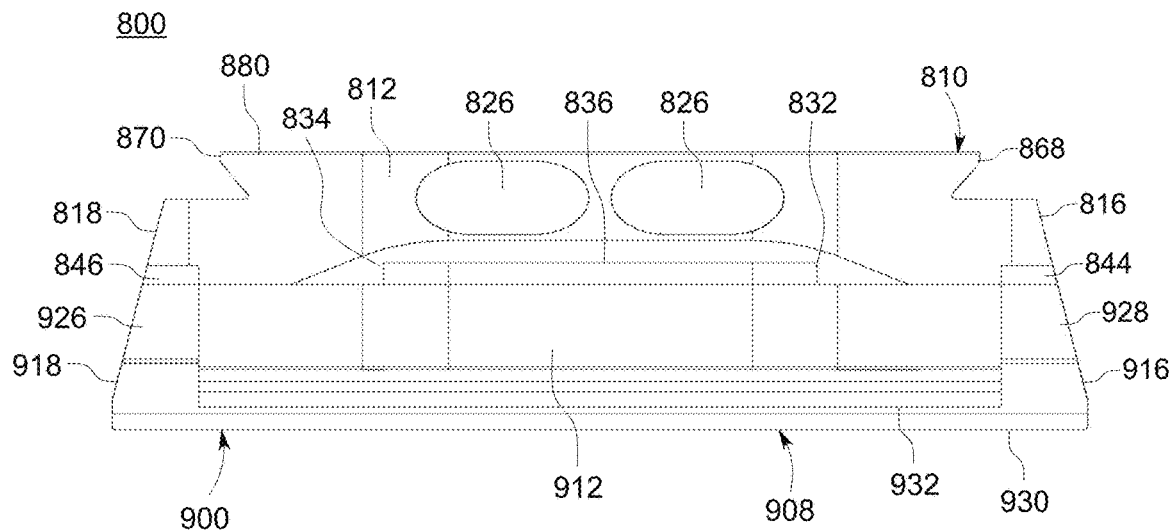
FIG. 65 is a first end view of the trial insert of FIG. 59, in accordance with an aspect of the present disclosure.
Figure 66:
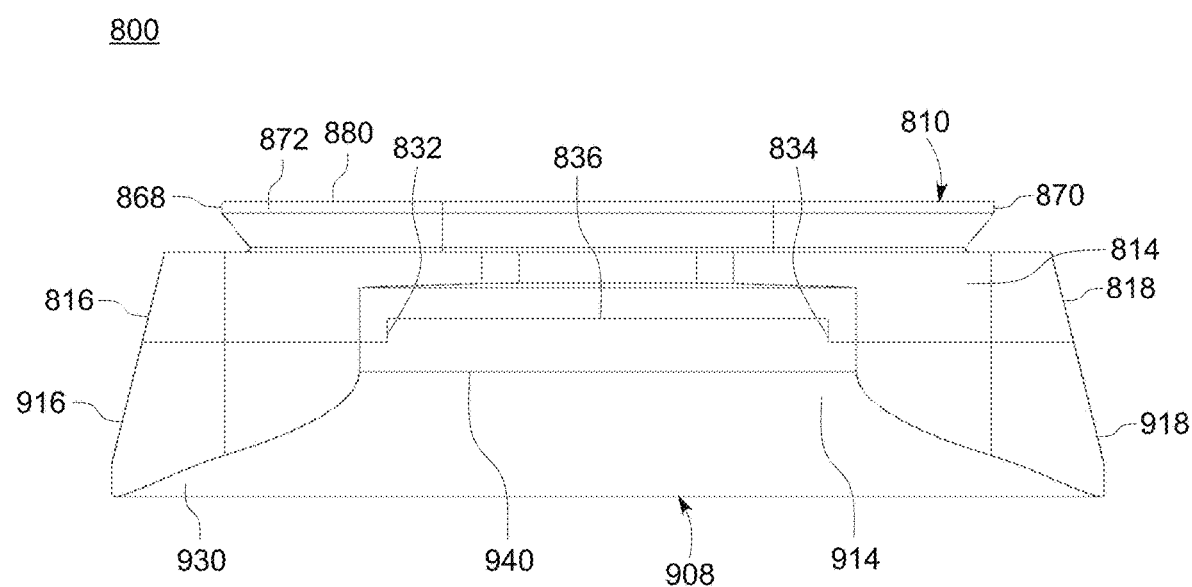
FIG. 66 is a second end view of the trial insert of FIG. 59, in accordance with an aspect of the present disclosure.
Figure 67:
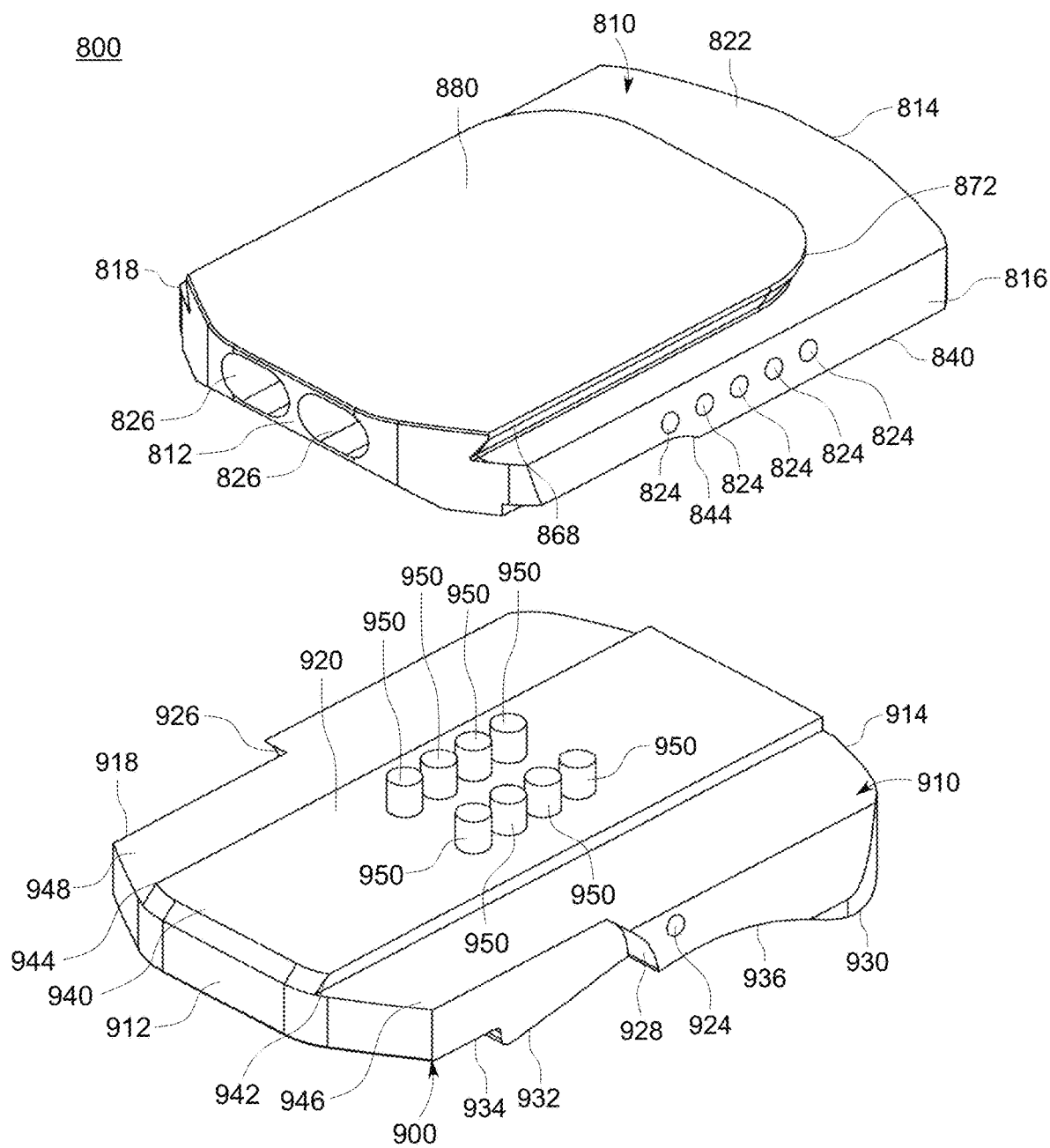
FIG. 67 is a first exploded, perspective view of the trial insert of FIG. 59, in accordance with an aspect of the present disclosure.

Referring to FIGS. 46, 52, and 58, a second member bore or second member cylinder 680 is shown extending from the engagement member top surface 620 toward the bottom surface 608. The second member bore 680 may, for example, have a diameter that ranges from approximately 5 mm to 15 mm and more specifically, may have a diameter of approximately 9.5 mm. The second member bore 680 may be positioned between the first engagement feature 642 and the second engagement feature 644 of the engagement member 640. The second member bore 680 may, for example, intersect the transverse bore 624.

Referring to FIGS. 46-51, and 58, the lock screw 550 is shown with a lock screw body or lock screw shaft 556, with the head 558 connected to one end and the locking foot 554 connected to an opposite end of the lock screw shaft 556. The lock screw body 556 is elongated and may be, for example, cylindrical. The lock screw body 556 may have, for example, threading extending along at least a portion of the length of the body 556 to engage an interior of the screw bore 552. Alternatively, the lock screw body 556 may be, for example, unthreaded or fully threaded. The lock screw body 556 may alternately have, for example, protrusions, spikes, barbs, or similar anchoring features extending outwards. The head 558 is shown with a circular or cylindrical shape and a hex or hexagonal drive type. However, other embodiments may include other head shapes or drive types. The head 558 may also have, for example, a protrusion 551 extending from the head 558 perpendicular to the shaft 556, and aligned with the foot 554, such that the protrusion 551 may be used to indicate an approximate rotational position of the foot 554. In other embodiments, protrusion 551 may be, for example, a notch, a marking, or an indicator aligned with the position of the foot 154. The foot 554 may have, for example, an ovular or elliptical plate, with a length and width larger than thickness, and one end of the foot being flared. The foot 554 is shown extending from the end in an approximately perpendicular direction to the lock screw shaft 556, with the flared end extending away from the lock screw shaft 556 and the narrower end connected to the lock screw shaft 556. In other embodiments, the foot may be, for example, any shape such that the length of the foot is larger than the width. The lock screw 550 may be, for example, a monolithic component.

With reference to FIGS. 46, 48, 49, and 52, a lock screw bore 552 extends from the first end 612 towards the second end 614 of the second member 600. The lock screw bore 552 is shown extending from the first end 612 to the second end 614 but in other embodiments, the lock screw bore 552 may extend towards but not entirely to the second end 614. The lock screw bore 552 is shown as being cylindrical although alternative shapes which receive the lock screw 550 are also contemplated. The second member bore 680 extends towards the bottom surface 648 such that the second member bore 680 intersects with the lock screw bore 552. The intersection between the second member bore 680 and the lock screw bore 552 may result in, for example, the intersecting portion of the lock screw bore 552 being a channel 560.

With reference to FIG. 58, the lock screw 550 is shown with the head at the first end 612, and the lock screw body 556 extending into the lock screw bore 552, into the intersection between the lock screw bore 552 and the second member bore 680, with the foot 554 protruding from the second member bore 680. The lock screw 550 may be, for example, rotatable about a screw shaft longitudinal axis and within the lock screw bore 552. The foot 554, being within the channel 560, may be, for example, able to rotate between a first or transverse position and a second or dorsal position about the screw shaft longitudinal axis, and protruding from the top of the second member bore 680 above the engagement member 620.

As shown in FIGS. 47-51, and 32, the articulated surface 608 of the second member 600 includes a first segment 634, a second segment 632, a third segment 636, a fourth segment 630, and a trial engagement member 622. The first segment extends from the first end 612 towards the second end 614, and may have, for example, a planar surface. The second segment 632 may extend, for example, from an end of the first segment 634, generally perpendicular to the articulated surface 608 forming a first portion of the second segment 632. The first portion of the second segment 632 may, for example, extend away from the articulated surface 608, for an exemplary embodiment of approximately 1 mm, although alternate distances are contemplated as would be known by one having ordinary skill in the art. From the free end of the first portion, the second segment 632 may, for example, curve or angle towards the top surface 610 and the second end 614 forming a second portion. The second portion of the second segment 632 may form, for example, a hypotenuse that connects to the third segment 636. The hypotenuse portion may be, for example, approximately 2.6 mm or greater, and more specifically have a linear distance of approximately 4.75 mm. The third segment 636 extends from an end of the second segment 632 towards the second end 614 of the second member 600 and connects with the fourth segment 630. The third segment 636 may, for example, be approximately parallel to the top surface 610 or may have a concave curvature between the second segment 632 and fourth segments 630. The third segment 636 may be, for example, curved in the direction of a longitudinal axis extending from the first end 612 to the second end 614. The fourth segment 630 may have, for example, a convex curvature extending from the third segment 636 and to the second end 614. The fourth segment 630 may be, for example, curved in the direction of the longitudinal axis.

As further shown in FIGS. 47-51, and 53, the trial engagement member 622 extends from the articulated surface 608 outwards, forming a raised structure extending from the second segment 632 to the third segment 636. The trial engagement member 622 further has a length which may be, for example, approximately perpendicular to the first end 612 and the second end 614. The trial engagement member has a width which may, for example, be approximately perpendicular to the first side 616 and the second side 618. The trial engagement member 622 may have, for example, a length larger than the width. The trial engagement member 622 may, for example, have an exemplary length of approximately 14 mm, although alternate distances are contemplated as would be known by one having ordinary skill in the art. The trial engagement member 622 may, for example, have an exemplary width of approximately 6 mm, although alternate distances are contemplated as would be known by one having ordinary skill in the art. The trial engagement member 622 further has a bottom surface which may, for example, be a planar surface which extends approximately parallel with the engagement member top surface 620.

With reference to FIGS. 38-58, the trial insert 500 is configured (e.g. shaped and dimensioned) for engagement with a tibial trial component or tibial implant at the trial engagement member 580, engagement between the first member 510, the shim 700, and the second member 600, and engagement between the second member 600 and a talar trial component or a talar implant (not shown). The first, second, and third engagement features 568, 570, 572, of the trial engagement member 580, engage with a tibial trial component (not shown), providing a fixed support for the first member 510 of the trial insert 500.

With continued reference to FIGS. 38-58, the engagement member 640 and the engagement slot 738 of the shim 700 are engaged at the first engagement features 642, 732 (e.g. female dovetail and male dovetail features) and at the second engagement features 644, 734 (e.g. female dovetail and male dovetail features), providing a linkage for movement of the shim 700 and the second member 600 relative to each other in an anterior/posterior direction along the engagement member 640 and the engagement slot 738. The engagement member 750 of the shim 700 is also engaged with the engagement slot 528 of the first member at the first engagement features 532, 732 (e.g. female dovetail and male dovetail features) and at the second engagement features 534, 734 (e.g. female dovetail and male dovetail features), providing a linkage for movement of the first member 510 and the shim 700 relative to each other, and providing for relative position translation along the interface between the engagement slot 528 and the shim engagement member 750 in an anterior/posterior direction. However, since the first member 510 may be, for example, connected to the tibial trial component (not shown), the first member 510 may remain fixed and the shim 700 moveable along the engagement member 750/engagement slot 528 interface. The second member 600 is moveable along the engagement member 640/shim engagement slot 738 interface in the anterior/posterior direction. Thus, the shim 700 may be, for example, translatable relative to the first member 510, and the second member 600 may be translatable relative to the shim 700 and the first member 510. The second member is further engaged with the talar trial component (not shown) along the articulated surface 608, such that plantar flexion, neutral, and dorsiflexion motions may be simulated, and the positions of the trial insert 500 refined by further positioning the first member 510 relative to the second member 600. After the second member 600 is placed in a desired anterior/posterior position, the at least one locking groove 538 of the first member 510 may be, for example, above the second member bore 680 and the lock screw 550 may be rotated about the lock screw longitudinal axis, such that the flared end of the foot 554 engages with one of the at least one locking openings 748 on the shim 700, passing through to engage one of the at least one locking groove 538 of the first member.

In another embodiment a plurality of shims (e.g. a plurality of the shim 700) may be used, such that an engagement slot of a bottom shim (e.g. the engagement slot 738) engages with engagement member 640 and an engagement member (e.g. the engagement member 750) engages with an engagement slot (e.g. the engagement slot 738) of a subsequent shim. The engagement member of the top shim (e.g. the engagement member 750) may be engaged with the engagement slot 528 of the first member 510. Additionally, shim 700 may be provided as a plurality of shims having a plurality of thicknesses, to accommodate surgical preferences, bone preparation, and bone and joint sizing.

Referring to FIGS. 59-74, a trial insert 800 is shown. The insert 800 includes a first member or movable member 810 and a second member or base member 900. The first member 810 includes a top surface 822 opposite a bottom surface 848. The second member 900 includes a top surface 910 opposite a bottom surface, or articulated surface 908. The top surface 910 of the second member 900 couples to the bottom surface 848 of the first member 810. The first member 810 and the second member 900 may come in multiple sizes for use with patients having different size tibia and talar bones and requiring different sizes of trials or implants.

As shown in FIGS. 67-74, the first member 810 includes a first end or anterior end 812 opposite a second end or posterior end 814. The first member 810 may have a length between the first end 812 and the second end 814 that ranges from, for example, 28 mm to 42 mm and more specifically, may be approximately 30 mm. The first member 810 also includes a first side or medial side 816 opposite a second side or lateral side 818. The width between the first side 816 and the second side 818 may range from, for example, 20 mm to 34 mm and more specifically, may be approximately 20 mm. The top surface 822 includes a bone trial connector, a trial engagement member, or a prosthetic engagement member 880, extending from the anterior end 812 towards the posterior end 814 and inset from the posterior end 814 as shown in FIGS. 61, 63, 64, and 71-73. The trial engagement member 880 may be inset from the second end 814, for example, approximately 4 mm to 8 mm, and more specifically approximately 7 mm. In addition, the trial engagement member 880 may be, for example, inset approximately 0 mm to 5 mm, more specifically, approximately 0 mm to 3 mm from the first side 816 and the second side 818 respectively, and, yet more specifically inset approximately 1.8 mm from the first side 816 and the second side 818, as shown in FIGS. 23, 24, 27 and 28. The insets from the first side 816 and the second side 818 of the trial engagement member 880 also may be, for example, approximately equidistant. In an alternative embodiment, the trial engagement member 880 may, for example, extend between the first side 816 and the second side 818 and from the anterior end 812 to the posterior end 814.

The trial engagement member 880 may have, for example, engagement features along sections of the perimeter such as a first engagement feature or first male dovetail 868, a second engagement feature or second male dovetail 870, and a third engagement feature or third male dovetail 872 as shown in FIGS. 59, 61, 67, and 73. The first engagement feature 868 and the second engagement feature 870 may, for example, extend from the anterior end 812 towards the posterior end 814, with the two engagement features, 868, 870 may extend, for example, approximately parallel. The male dovetail features may face in opposing directions towards the medial and lateral sides, 816 and 818, respectively, as shown in FIGS. 61 and 73. With continued reference to FIGS. 61 and 73, the third engagement feature 872 may be, for example, approximately perpendicular and extend between or connect to the first engagement feature 868 and the second engagement feature 870. The third male dovetail 872 may, for example, face the posterior end 814. The connection between the first engagement feature 868 and the third engagement feature 872 and the connection between the second engagement feature 870 and the third engagement feature 872 may, for example, be tapered, angled, squared, curved, or arced.

With reference to FIGS. 63-66 and 69-72, the trial engagement member 880 may, for example, extend away from the top surface 822 of the first member 810. The trial engagement member 880 may, for example, have an exemplary embodiment height of approximately 1.6 mm, although alternate heights are contemplated as would be used by one having ordinary skill in the art. The trial connection 880 may have, for example a planar top surface. In other embodiments, the trial engagement member 880 may have, for example, a vertical bore extending from the top surface of the trial engagement member 880 towards the bottom surface 848 of the first member 810.

With reference to FIGS. 65, 66, 69, and 70, the first side 816 and the second side 818 of the first member 810 may be, for example, sloped, tapered, or angled as the sides (e.g. the first side 816 and the second side 818) extend between the top surface 822 and the bottom surface 848 of the first member 810. The angle of the first side 816 and the second sides 818 extending from the top surface 822 to the bottom surface 848 may be, for example, approximately 30° to 60° extending outwards from vertical and more specifically approximately 45° outwards from vertical.

With reference to FIGS. 61, 62, 73, and 74, the first end 812 and second end 814 each have a surface that may, for example, be angled to approximately form an isosceles trapezoid or to have a convex curvature.

With continued reference to FIGS. 65, 66, 69, and 70, the first end 812 is shown with at least one front opening or front bore 826, having, for example, an ovular shape or elliptical shape. In other embodiments, the at least one bore 826 may be circular. The at least one front bore 826 may be, for example, two front bores. In other embodiments, there may be, for example, a single front bore 826 or more than two front bores 826. The two front bores 826 may be shaped and configured for use with an insertion instrument (not shown), more specifically, a forked insertion instrument (not shown).

Referring now to FIGS. 63, 64, 67, 68, 71, and 72, at least one transverse bore 824 is shown extending from the medial side 816 to the lateral side 818. The at least one transverse bore 824 may be, for example, five transverse bores. However, there may be embodiments with more or less than five transverse bores 824, for use with patients having different sizes of tibia and tibial trials. The transverse bores 824 may have diameters ranging from, for example, approximately 0.25 mm to 2.0 mm and more specifically, may be approximately 1 mm. The medial side 816 further has a medial notch or first notch 844 extending from the medial side 816, towards the lateral side 818. The lateral side 818 has a lateral notch or second notch 846, extending from the lateral side 818 towards the medial side 816. The first and second notches, 844, 846, also extend from the first end 812 towards the second end 814.

Referring now to FIGS. 68 and 74, the bottom surface 848 of the first member 810 is shown. The bottom surface 848 includes a recessed region or engagement region 836 extending into the first member 810 from the bottom surface 848 toward the top surface 822. The bottom surface 848 also includes an engagement slot or an engagement channel 828 extending from the first end 812 into the recessed region 836 to the second end 814 and bordered toward the first side 816 by a first engagement feature 832 and bordered toward the second side 818 by a second engagement 834. The engagement channel 828, first engagement feature 832, and second engagement feature 834 may have, for example, a tapered region 850 extending from the first side 812 towards the bottom surface 848 as shown in FIGS. 63, 64, 71, and 72. The recessed region 836 may have a width between the first and second engagement features 832, 834 and the width may be, for example, approximately 10 mm. In another embodiment, the recessed region may be positioned on the second member and the engagement region may be on the first member. The first member 810 may come in multiple sizes for use with patients requiring different sized trials and/or implants and the engagement channel 828 of each of the first members 810 may be, for example, sized and shaped the same to allow for replacement of the first member 810 as needed.

Referring to FIGS. 68-70 and 74, the width of the first member 810 between the first side 816 and the second side 818 at the top surface 822 may be, for example, approximately constant from the first end 812 to the second end 814. First side 816 and second side 818 may be, for example, sloped out form the first member between the top surface and the bottom surface 848. Thus, the width may increase between the top surface 822 and the bottom surface 848. At the bottom surface the width of the first member 810 from the first end to the notches 844, 846 is narrower than the width of the first member 810 from the notches 844, 846 to the second end 814. With additional reference to FIG. 10, the various insets (e.g. inset E, F, G, and H) are similarly described here. The first and second engagement features 832, 834 are inset from the sides (e.g. the first side 816 and the second side 818). The first engagement feature 832 may be, for example, inset from the first side 816 by approximately 1 mm to 5 mm, between the medial notch 844 and the first end 812 and by approximately 1 mm to 7 mm, between the medial notch 844 and the second end 814. The first engagement feature 832 may be, more specifically, inset from the first side 816 by approximately 4.3 mm from the medial notch 844 to the first end 812 and by approximately 5.5 mm from the medial notch 844 to the second end 814. The second engagement feature 834 may be, for example, inset from the second side 818 by approximately 1 mm to 5 mm between the lateral notch 846 and the first end 812 and by approximately 1 mm to 7 mm between the lateral notch 846 and the second end 814. The second engagement feature 834 may be, for example, inset from the second side 818 by approximately 4.3 mm between the lateral notch 846 and the first end 812 and by approximately 5.5 mm between the lateral notch 846 and the second end 814. The first engagement feature 832 and the second engagement feature 834 may be positioned, for example, approximately equidistant from the first side 816 and the second side 818, respectively. The first engagement feature 832 and the second engagement feature 834 may be, for example, perpendicular to the bottom surface medial side 840 and the bottom surface lateral side 842, respectively.

The portion of the bottom surface 848 between the medial side 816 and the recessed region 836 is the bottom surface medial side 840. The portion of the bottom surface 848 between the lateral side 818 and the recessed region 836 is the bottom surface lateral side 842.

The bottom surface 848 of the first member 810 also includes at least one engagement bore 838. The at least one engagement bore 838 may be, for example, positioned within the recessed region 836, between the anterior end 812 and the posterior end 814, and between the medial side 816 and the lateral side 818. The at least one engagement bore 838 may be, for example, circular or any other shape. In an exemplary embodiment, the at least one engagement bore 838 may also include, for example, a diameter of approximately 1.5 mm, although alternate diameters are contemplated as would be used by one having ordinary skill in the art. The at least one engagement bore 838 may be, for example, eight engagement bores with the engagement bores arranged as an approximately parallel set of four pairs. However, other embodiments may have more or less than eight bores 838, based on the size of the trial insert 300 and the corresponding size of the patient's tibia and talus. In addition, the bores 838 may be positioned along the entire length of the recessed region 836 or along only a portion of the recessed region 836. Additional embodiments may have, for example, a single line of bores rather than a parallel set of pairs, a grouping of non-parallel pairs of bores, or a plurality of parallel lines of bores.

With continued reference to FIGS. 68 and 74, the alignment of the engagement bores 838 with the transverse bores 824 provides a visual marker of the position of the interior engagement bores 838 on an exterior of the first member 810. The surgeon may use the exterior bores 824 to align engagement protrusions 950 with the interior engagement bores 838 during the surgical procedure to secure the first member 810 to the second member 900.

Referring now to FIGS. 59-74, the second member, base member, or articulating member 900 has a first end or anterior end 912 opposite a second end or posterior end 914. The second member 900 also has a first side or medial side 916 opposite a second side or lateral side 918. In addition, the second member 900 has the top surface 910 opposite the articulated surface 908. The first and second sides 916, 918 may have, for example, a first notch 928 in the first side 916, extending towards the second side 918, and a second notch 926 in the second side 918, extending towards the first side 916, with the notches 928, 926, extending from the first end 912 towards the second end 914, as shown in FIGS. 73 and 74. The first end 912 and second end 914 each have a surface that may, for example, be angled to approximately form an isosceles trapezoid or to have a convex curvature.

As shown in FIGS. 65, 66, 69, and 70, the sides (e.g. the first side 916 and the second side 918) may be angled, for example, approximately 30° to 60° outward from the vertical and more preferably, approximately 45°, as the first side 916 and the second side 918 extend between the top surface 910 and the articulated surface 908.

Referring to FIGS. 69, 70, 73, and 74, the medial side 916 and the lateral side 918 have notches 928, 926 extending from the anterior side 912 towards the posterior side 914. The notches 928, 926 further extend from the top surface 910 to the articulated surface 908 and maybe, for example, vertical between the top surface 910 and the bottom surface 908. The first notch 928 may, for example, have the same angle as the first side 916 between the top surface 910 and the articulated surface 908. The second notch 926 may, for example, have the same angle as the second side 918 between the top surface 910 and the articulated surface 908. However, the first notch 928 and the second notch 926 may have angles that differ from the first side 916 and second side 918, respectively, with angles ranging from vertical to 60° from the top surface 910 to the articulated surface 908. The sides further have a transverse bore 924, extending from the medial side 916 to the lateral side 918. The transverse bore 924 may have a diameter, for example, that range from approximately 0.25 mm to 2.0 mm, and more specifically, of approximately 1 mm.

As shown in FIGS. 67 and 69-73, the top surface 910 of the second member 900 includes a raised section or an engagement member 940, raised out from the top surface 910 and extending from the anterior end 912 to the second end or posterior end 914. With additional reference to FIG. 9, the various insets (e.g. inset A, B, C, and D) are similarly described here. For the sake of brevity, the inset measurements and dimensions are approximately the same. The engagement member 940 has a first engagement feature 942 inset from the medial side 916, and a second engagement feature 944 inset from the lateral side 918. The engagement member 940 is positioned between a medial surface 946 and a lateral surface 948. The first engagement feature 942 and the second engagement feature 944 may be, for example, perpendicular to the medial surface 916 and a lateral surface 918. The first engagement feature 942 and the second engagement feature extend from the first end 912 towards the second end 914. The engagement member 940, first engagement feature 942, and second engagement feature 944 may have, for example, a tapered region 960 extending from the first side 912 and towards the second side, sloping to meet the engagement member top surface 920, as shown in FIGS. 63, 64, 71, and 72.

Referring to FIGS. 67-73, the engagement member 940 is shown with at least one engagement protrusion 950 extending in an approximately perpendicular direction out from the top surface 910 of the engagement member 940. The at least one engagement protrusion 950 may be, for example, a set of eight cylindrical pairs, the pairs being arranged in an approximately parallel formation in the anterior/posterior direction. Alternative numbers of engagement protrusions 950 are also contemplated and may include both odd and even numbers of engagement protrusions 950. Additional embodiments may have, for example, a single line of protrusions (e.g. multiple instances of at least one engagement protrusion 950) rather than a parallel set of pairs, a grouping of non-parallel pairs of protrusions, or a plurality of parallel lines of protrusions. The engagement member 940 and the at least one engagement protrusion 950 are configured, shaped and dimensioned, for engagement with the at least one engagement bore 838 and the engagement slot 828 of the first member 810.

Referring to FIGS. 67-74, the number of the at least one engagement bore 838 is shown equal to the number of the at least one engagement protrusion 950. In other embodiments there may be, for example, fewer engagement protrusions (e.g. the at least one engagement protrusion 950) than engagement bores (e.g. the at least one engagement bore 838). In embodiments where the bores 838 and protrusions 950 are aligned in pairs, there may be, for example, fewer engagement protrusion 950 pairs than engagement bore 838 pairs. In embodiments with fewer engagement protrusions 950 than engagement bores 838 the relative position of the first member 810 to the base member 900 is adjustable in the anterior/posterior direction.

As shown in FIGS. 58-72, and 74, the articulated surface 908 of the second member 900 includes a first segment 934, a second segment 932, a third segment 936, a fourth segment 930, and a trial engagement member 922. The first segment extends from the first end 912 towards the second end 914, and may have, for example, a planar surface. The second segment 932 may have a triangular or wedge shape from a side view. The second segment 932 may extend, for example, from an end of the first segment 934, generally perpendicular to the articulated surface 908 forming a first portion of the second segment 932. The first portion of the second segment 932 may, for example, extend away from the articulated surface 908, for an exemplary embodiment of approximately 1 mm, although alternate distances are contemplated as would be known by one having ordinary skill in the art. From the free end of the first portion, the second segment 932 may, for example, curve or angle towards the top surface 910 and the second end 914 forming a second portion. The second portion of the second segment 932 may form, for example, a hypotenuse that connects to the third segment 936. The hypotenuse portion may be, for example, approximately 2.6 mm or greater, and more specifically have a linear distance of approximately 4.75 mm. The third segment 936 extends from an end of the second segment 932 towards the second end 914 of the second member 900 and connects with the fourth segment 930. The third segment 936 may, for example, be approximately parallel to the top surface 910 or may have a concave curvature between the second segment 932 and fourth segments 930. The third segment 936 may be, for example, curved in the direction of a longitudinal axis extending from the first end 912 to the second end 914. The fourth segment 930 may have, for example, a convex curvature extending from the third segment 936 and to the second end 914. The fourth segment 930 may be, for example, curved in the direction of the longitudinal axis.

As further shown in FIGS. 68-72, and 74, the trial engagement member 922 extends from the articulated surface 908 outwards, forming a raised structure extending from the second segment 932 to the third segment 936. The trial engagement member 922 further has a length which may be, for example, approximately perpendicular to the first end 912 and the second end 914. The trial engagement member 922 has a width which may be, for example, approximately perpendicular to the first side 916 and the second side 918. The trial engagement member 922 may have, for example, a length larger than the width. The trial engagement member 922 may, for example, have an exemplary length of approximately 14 mm, although alternate distances are contemplated as would be known by one having ordinary skill in the art. The trial engagement member 922 may, for example, have an exemplary width of approximately 6 mm, although alternate distances are contemplated as would be known by one having ordinary skill in the art. The trial engagement member 922 further has a bottom surface which may, for example, be a planar surface which extends parallel with the engagement member top surface 920.

The trial insert 800 is configured (e.g. shaped and dimensioned) for engagement with a tibial trial component or tibial implant at the trial engagement member 880, engagement between the first member 810 and the second member 900, and engagement between the second member 900 and a talar trial component or talar implant (not shown). The first, second, and third engagement features 868, 870, 872 of the trial engagement member 880 engage with a tibial trial component (not shown), providing a fixed support for the first member 810 of the trial insert 800. The at least one protrusion 950 is inserted into the at least one engagement bore 838 and the engagement member 940 and the engagement slot 828 are engaged at the first engagement features 832, 942 and at the second engagement features 834, 944, providing a linkage. The second member 900 engages with the talar trial component (not shown) along the articulated surface 908, such that plantar flexion, neutral, and dorsiflexion motions may be simulated. In embodiments with fewer engagement protrusions than engagement bores, the positions of the trial insert 800 may be refined by positioning the first member 810 relative to the second member 900 in the anterior/posterior direction.

The surgical method may be as described in greater detail in U.S. Provisional Application No. 62/899,460, entitled Total Ankle Replacement Surgical Method, which is hereby incorporated by reference in its entirety. The various embodiments of the trial insert 100, 300, 500, and 800 may be used in methods to determine the correctness of the cut and position of a tibia and talus (potentially at least partially resected) of a patient, in conjunction with a total ankle replacement (TAR) guide. The TAR guide has a tibial trial component and a talar trial component. The various embodiments of the trial insert 100, 300, 500, and 800 may be used, for example, with a tibial trial component and a talar trial component to determine a stable replacement ankle joint that provides for a full articulation/motion of the joint.

The articulated surface 408 of base member 400, the articulated surface 208 of base member 200, the articulated surface 608 of base member 600, the articulated surface 908 of base member 900, and the interaction of trial inserts 100, 300, 500, 800 with tibial trial components and talar trial components may also be as described in greater detail in U.S. Provisional Application No. 62/779,092, filed Dec. 13, 2018, entitled Instruments, Guides and Related Methods for Total Ankle Replacement, which is hereby incorporated by reference in its entirety.

For example, a plurality of tibial trial components, talar trial components, and trial inserts (e.g. a plurality of trial inserts 100, 300, 500, 800) may be configured or provided with differing anterior/posterior lengths, medial/lateral widths, anterior/posterior positional offsets, and/or proximal/distal thicknesses thereof. Based on the trialing of one or more tibial trial component, one or more talar trial component and one or more tibial trial insert (e.g. one or more of trial inserts 100, 300, 500, 800), a particular size of the tibial trial component, talar trial component and/or tibial trial insert (and thereby corresponding tibial component, talar component, and tibial trial insert) may be selected based on the particular patient/ankle that best suits the patient/ankle (and utilized to prepare the tibia and/or talus for implantation of the tibial trial component, and talar trial component, respectively, therein/thereon).

The method for connecting the first member 310 to the base member 400 includes, for example, inserting the engagement member 440 into the engagement slot 328 such that the first female dovetail 332 engages with the first male dovetail 442 and at the second female dovetail 334 engages with the second male dovetail 444 of the base member 400, providing a linkage for movement of the engagement member 440 into and within engagement slot 328. Moving the first member 310 and the second member 400 relative to each other, provides for relative position translation along the interface between the engagement slot 328 and the engagement member 400, in the anterior/posterior direction.

For trial insert 300, the method of using the trial insert 300 with a TAR guide include, for example, inserting the engagement member 380 of the first member 310 into an engagement slot within the tibial trial component. Positioning the base member 400 on the talar trial component, such that the trial engagement member 422 and the articulated surface 408 engage with the talar trial component. Inserting engagement member 440 into engagement slot 328 such that the engagement member 380 of first member 310 connects to the tibial trial component and the engagement member 440 of the base member 400 connects to the engagement slot 328 of the first member 310. Placing the engagement member 422 and the articulated surface 408 of base member 400 onto and engaging with the talar trial component. Positioning the base member 400 in the anterior/posterior direction relative to the first member 310 and to the talar trial component.

The relative anterior/posterior positions of the first member 310 to the base member 400 may be done before, during, or after engagement of trial insert 300 with a TAR guide. The method noted above may also be repeated as the plurality of base members and first members are sized and positioned with the TAR guide until the desired base member 400 and first member 310 are selected.

The method for connecting the first member 110 to the base member 200 includes, for example, inserting the engagement member 240 into the engagement slot 128 such that the first female dovetail 132 engages with the first male dovetail 242 and at the second female dovetail 134 engages with the second male dovetail 244, providing a linkage for movement of the engagement member 240 into and within engagement slot 128. Moving the first member 110 and the second member 200 relative to each other, providing for relative position translation along the interface between the engagement slot 128 and the engagement member 200, in the anterior/posterior direction. Positioning the first member 110 relative to the second member 200 at a desired anterior/posterior offset, with at least one locking groove 138 positioned above the second member bore 280. Rotating the lock screw 150 about the lock screw longitudinal axis, such that the foot 154 engages with one of the at least one locking groove 138, and thereby preventing further anterior/posterior movement between the first member 110 and the base member 200.

For trial insert 100, the method of using the trial insert 100 with a TAR guide includes, for example, inserting the engagement member 180 of the first member 110 into an engagement slot within the tibial trial component. Positioning the base member 200 on the talar trial component, such that the trial engagement member 222 and the articulated surface 208 engage with the talar trial component. Inserting engagement member 240 into engagement slot 128 such that the engagement member 180 of first member 110 connects to the tibial trial component and the engagement member 240 of the base member 200 connects to the engagement slot 128 of the first member 110. Placing the engagement member 222 and the articulated surface 208 of base member 200 onto and engaging with the talar trial component. Positioning the base member 200 in the anterior/posterior direction relative to the first member 110 and to the talar trial component.

The relative anterior/posterior positions of the first member 110 to the base member 200 may be done before, during, or after engagement of trial insert 100 with a TAR guide. The method noted above may also be repeated as the plurality of base members and first members are sized and positioned with the TAR guide until the desired base member 200 and first member 110 are selected.

The method for connecting the first member 510 to the base member 600 using the shim 700 includes, for example, connecting the shim 700 to base member 600 by inserting the engagement member 640 into the engagement slot 738, such that the first female dovetail 732 engages with the first male dovetail 642 and the second female dovetail 734 engages with the second male dovetail 644, and providing a linkage for movement of the engagement member 640 into and within engagement slot 738. Connecting the base member 600 and the shim 700 to the first member 510 by inserting the engagement member 750 into the engagement slot 528 such that the first female dovetail 532 engages with the first male dovetail 752 and the second female dovetail 534 engages with the second male dovetail 754, providing a linkage for movement of the engagement member 750 into and within engagement slot 528. Moving the first member 510, the shim 700, and the second member 600 relative to each other, providing for relative position translation along the interface between the engagement slot 528 and the engagement member 750, and the engagement slot 738 and the engagement member 600, in the anterior/posterior direction. Positioning the first member 510, the shim 700, and the second member 600 relative to each other and at a desired anterior/posterior offset, with the at least one locking groove 538 and the at least one locking opening 748 aligned and positioned above the second member bore 680. Rotating the lock screw 550 about the lock screw longitudinal axis, such that the foot 554 engages with one of the at least one locking opening 748 and the at least one locking groove 538, and thereby preventing further anterior/posterior movement between the first member 510, the shim 700, and the base member 600. The method may be adjusted to accommodate the use of a plurality of shims (e.g. multiples of shim 700), where a first shim connects to a subsequent shim and a bottom shim connects to the base member 600 and a top shim connects to the first member 510. In other embodiments, shim 700 may be provided as a plurality of shims having a plurality of thicknesses to accommodate spacing between the first member 510 and the second member 600, due to patients having different size tibia and talar bones.

For trial insert 500, a method of using the trial insert 500 includes, for example, inserting the engagement member 580 of the first member 510 into an engagement slot within a tibial trial component. Positioning the base member 600 on the talar trial component, such that the trial engagement member 622 and the articulated surface 608 engage with the talar trial component. Inserting engagement member 640 into engagement slot 738 and engagement member 750 into engagement slot 528, such that the engagement member 580 of first member 510 connects to the tibial trial component and the shim 700 connects the first member 510 and the base member 600. Placing the engagement member 622 and the articulated surface 608 of base member 600 onto and engaging with the talar trial component. Positioning the base member 600 and the shim 700 in the anterior/posterior direction relative to the first member 510 and to the talar trial component. The method may be adjusted to accommodate the use of a plurality of shims (e.g. multiples of shim 700), where a first shim connects to a subsequent shim and a bottom shim connects to the base member 600 and a top shim connects to the first member 510. In certain embodiments, the first member 510 and the second member 600 may engage without the need of a shim, if surgically desired.

The relative anterior/posterior positions of the first member 510 and the shim 700 to the base member 600 may be done before, during, or after engagement of trial insert 500 with a TAR guide. The method may also be repeated as the plurality of base members 600 and first members 510 are sized and positioned with the TAR guide until the desired base member 600 and first member 510 are selected.

A method for connecting the first member 810 to the base member 900 includes, for example, aligning the at least one protrusion 950 with the at least one engagement bore 838 and aligning the engagement member 940 with the engagement slot 828, such that the first engagement features 832, 942 and at the second engagement features 834, 944 are aligned. Inserting the at least one protrusion 950 into the at least one engagement bore 838 such that first engagement features 832, 942 and the second engagement features 834, 944 are aligned and engaged. Provided there are more bores than protrusions, the protrusions may be removed from the current bores, the relative position of the first member 810 and the second member 900 may be adjusted, and the protrusions inserted into a different set of bores. The second member 900 engages with the talar trial component (not shown) along the articulated surface 908, such that plantar flexion, neutral, and dorsiflexion motions may be simulated, and the positions of the trial insert 800 refined by further positioning the first member 810 relative to the second member 900.

For trial insert 800, a method of using the trail insert 800 with a TAR guide includes, for example, inserting the engagement member 880 of the first member 810 into an engagement slot within the tibial trial component. Positioning the base member 900 on the talar trial component, such that the trial engagement member 922 and the articulated surface 908 engage with the talar trial component. Determining the relative anterior/posterior position for the first member 810 relative to the second member 900. Removing the first member 810 from the tibial trial component and removing the base member 900 from the talar trial component. Inserting the at least one protrusion 950 into the at least one engagement bore 838 and engaging the engagement member 940 with the engagement slot 828 at the first engagement features 832, 942 and at the second engagement features 834, 944. Inserting trial insert 800 into the TAR guide by inserting the engagement member 880 into an engagement slot within the tibial trial component and engaging the trial engagement member 922 and the articulated surface 908 with the talar trial component.

The relative anterior/posterior positions of the first member 810 to the base member 900 may be done before or after engagement of trial insert 800 with a TAR guide. The method may also be repeated as the plurality of base members and first members are sized and positioned with the TAR guide until the desired base member 900 and first member 810 are selected.

Throughout the various embodiments, transverse bores (124, 324, 524, and 824) and the transverse bore (224, 424, 624, and 924) may be, for example, used to measure the relative anterior/posterior position of the first member (110, 310, 510, and 810) to the second member (200, 400, 600, and 800) and to measure positional adjustments. As the first member (110, 310, 510, and 810) is moved relative to the second member (200, 400, 600, and 800), the distance of the transverse bore (224, 424, 624, and 924) relative to an individual transverse bore of transverse bores (124, 324, 524, and 824) may be determined to select a desired final position.

Throughout the various embodiments, the vertical bores may be used to store magnets to encourage the first members (110, 310, 510, and 810) to remain in close proximity to the second members first members (110, 310, 510, and 810).

The first members (110, 310, 510, and 810) and the second members, first members (110, 310, 510, and 810) may be made from, for example, polyethylene, including Ultem, Radel, or a Delrin copoly.

The notches in the various embodiments (100, 300, 500, and 800) may be for clearance when used with other equipment, and when the first members and second members slide relative to each other.

For various embodiments (100 and 500) the screw (150, 550) may be locked into the grooves. However, any similar mechanism to lock the sliding surfaces may be used.

As may be recognized by those of ordinary skill in the art based on the teachings herein, numerous changes and modifications may be made to the above-described and other embodiments of the present disclosure without departing from the scope of the disclosure. The components of the implants as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the implants may include more or fewer components or features than the embodiments as described and illustrated herein. For example, the components and features of FIGS. 1-16, FIGS. 17-37, FIGS. 38-58, and FIGS. 59-71 may be used interchangeably and in alternative combinations as would be modified or altered by one of skill in the art. Specifically, the first members 110, 310, 510, 810, the second members 200, 400, 600, 900, the screws 150, 550, and the shim 700 may be used in alternative combinations as would be modified or altered by one of skill in the art. Accordingly, this detailed description of the currently-preferred embodiments is to be taken in an illustrative, as opposed to limiting of the disclosure.

The above disclosure describes a portion of a total ankle replacement (TAR) procedure and the devices used in that procedure. Additional understanding of the TAR procedure may be found in International Application No. PCT/US2019/029009 filed Apr. 24, 2019 and entitled Implants and Methods of Use and Assembly, International Application No. PCT/US2019/066404 filed on Dec. 13, 2019 and entitled Instruments, Guides and Related Methods for Total Ankle Replacement, U.S. Provisional Application No. 62/890,611 filed Aug. 22, 2019 and entitled Patient Specific Instruments and Methods of Use, International Application No. PCT/US2019/066336 filed on Dec. 13, 2019 and entitled Patient Specific Instruments and Methods of Use, U.S. Provisional Application No. 62/899,703 filed Sep. 12, 2019 and entitled Joint Replacement Alignment Guides, Systems and Methods of Use and Assembly, International Application No. PCT/US2019/066408 filed on Dec. 13, 2019 and entitled Joint Replacement Alignment Guides, Systems and Methods of Use and Assembly, U.S. Provisional Application No. 62/899,655 filed Sep. 12, 2019 and entitled Alignment Instruments and Methods for Use in Total Ankle Replacement, International Application No. PCT/US2019/066149 filed on Dec. 13, 2019 and entitled Alignment Instruments and Methods for Use in Total Ankle Replacement, U.S. Provisional Application No. 62/899,740 filed Sep. 12, 2019 and entitled Joint Replacement Alignment Guides, Systems and Methods of Use and Assembly, International Application No. PCT/US2019/066393 filed on Dec. 13, 2019 and entitled Joint Replacement Alignment Guides, Systems and Methods of Use and Assembly, U.S. Provisional Application No. 62/898,615 filed Sep. 11, 2019 and entitled Resection Guides, Sweeping Reamers, and Methods for Use in Total Ankle Replacement, International Application No. PCT/US2019/064948 filed on Dec. 6, 2019 and entitled Resection Guides, Sweeping Reamers, and Methods for Use in Total Ankle Replacement, U.S. Provisional Application No. 62/898,854 filed Sep. 11, 2019 and entitled Distractors Having Attachable Paddles, Impaction Devices, and Methods for Use in Total Ankle Replacement, International Application No. PCT/US2019/066398 filed on Dec. 13, 2019 and entitled Distractors Having Attachable Paddles, Impaction Devices, and Methods for Use in Total Ankle Replacement, International Application No. PCT/US2019/066409 filed on Dec. 13, 2019 and entitled Total Ankle Replacement Surgical Method, which are each hereby incorporated herein in their entireties.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. A trial insert comprising:
   a first member comprising:
      an engagement channel extending from a bottom surface towards a top surface and along a first direction that extends from a first end to a second end;
      at least one transverse bore extending into the first member from at least one of a first side and a second side of the first member; and
      at least one front opening; and
      wherein the engagement channel comprises:
         a plurality of locking grooves recessed into the engagement channel, and wherein at least a portion of the plurality of locking grooves intersects with the at least one transverse bore of the first member; and
   a second member comprising:
      an engagement member extending away from a top surface and along a second direction that extends from a first end to a second end, wherein said engagement member is received within the engagement channel;
      at least one transverse bore extending into the second member from at least one of a first side and a second side of the second member; and
   wherein the first member is translatable relative to the second member along a longitudinal axis of the trial insert.

2. The trial insert of claim 1, further comprising:
   a lock screw, said lock screw comprising:
      a shaft;
      a head positioned at a first end of the shaft; and
      a foot positioned at a second end of the shaft and said foot positioned perpendicular to the shaft;
   wherein the second member further comprises:
      a screw bore extending through the second member along the second direction; and
      a second member bore extending from the engagement member towards the bottom surface;
      wherein the screw bore intersects with the second member bore; and
   wherein the shaft extends through the screw bore and into the second member bore and the foot is positioned within the second member bore.

3. The trial insert of claim 2, wherein the foot rotatably engages a locking groove of the plurality of locking grooves.

4. The trial insert of claim 3, wherein the head comprises:
   an indicator positioned on the head, and wherein the indicator extends in a direction aligned with the foot.

5. The trial insert of claim 1, further comprising:
   a shim comprising:
      an engagement member extending away from a top surface of the shim; and
      an engagement channel extending from a bottom surface of the shim towards the top surface;
   wherein the top surface of the shim engages the first member, wherein the bottom surface of the shim engages the second member, wherein the engagement member of the second member movably couples with the engagement channel of the shim, and wherein the engagement member of the shim movably couples with the engagement channel of the first member.

6. The trial insert of claim 5, wherein the shim comprises:
   a plurality of locking openings extending through the shim.

7. The trial insert of claim 6, wherein at least one of the plurality of locking openings aligns with at least one of the plurality of locking grooves of the first member, and
   wherein at least a portion of the foot is received within the at least one locking opening and the at least one locking groove.

8. The trial insert of claim 7, wherein the shim further comprises:
   a transverse hole recessed into a bottom surface of the shim, and
   wherein the transverse hole aligns with a locking opening of the plurality of locking openings.

9. The trial insert of claim 1, wherein the first member further comprises:
   a first bone trial connector positioned on the top surface of the first member.

10. The trial insert of claim 9, wherein the first bone trial connector includes:
    a top surface; and
    a bore, wherein the bore is recessed into the top surface of the first member.

11. The trial insert of claim 9, wherein the second member further comprises:
    a second bone trial connector positioned on a bottom surface of the second member.

12. A trial insert comprising:
    a first member comprising:
       an engagement channel extending from a bottom surface towards a top surface and along a first direction that extends from a first end to a second end;
       at least one transverse bore extending into the first member from at least one of a first side and a second side of the first member;
       at least one front opening; and
       a first bone trial connector positioned on the top surface of the first member, wherein the first bone trial connector comprises:
          a first male dovetail positioned towards the first side of the first member;
          a second male dovetail positioned towards the second side of the first member; and
          a third male dovetail;
          wherein the first male dovetail and the second male dovetail extend from the third male dovetail towards the first end; and
    a second member comprising:
       an engagement member extending away from a top surface and along a second direction that extends from a first end to a second end, wherein said engagement member is received within the engagement channel; and
       at least one transverse bore extending into the second member from at least one of a first side and a second side of the second member; and wherein the first member is translatable relative to the second member along a longitudinal axis of the trial insert.

\* \* \* \* \*